United States Patent
Kobayashi

(10) Patent No.: US 10,047,293 B2
(45) Date of Patent: *Aug. 14, 2018

(54) LIQUID CRYSTAL COMPOUND HAVING BUTENE-BONDING GROUP, LIQUID CRYSTAL COMPOSITION AND LIQUID CRYSTAL DISPLAY DEVICE

(71) Applicants: JNC CORPORATION, Tokyo (JP);
JNC PETROCHEMICAL CORPORATION, Tokyo (JP)

(72) Inventor: Masahide Kobayashi, Ichihara (JP)

(73) Assignees: JNC CORPORATION, Tokyo (JP);
JNC PETROCHEMICAL CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/821,175

(22) Filed: Aug. 7, 2015

(65) Prior Publication Data
US 2016/0040067 A1    Feb. 11, 2016

(30) Foreign Application Priority Data
Aug. 8, 2014 (JP) .................. 2014-162548

(51) Int. Cl.
| | | |
|---|---|---|
| G02F 1/1333 | (2006.01) | |
| C09K 19/34 | (2006.01) | |
| C09K 19/30 | (2006.01) | |
| C07C 43/29 | (2006.01) | |
| C07C 25/24 | (2006.01) | |
| C07D 309/06 | (2006.01) | |
| C07D 319/06 | (2006.01) | |
| C07D 213/30 | (2006.01) | |
| C07D 239/26 | (2006.01) | |
| C09K 19/32 | (2006.01) | |
| C09K 19/04 | (2006.01) | |

(52) U.S. Cl.
CPC .......... *C09K 19/3402* (2013.01); *C07C 25/24* (2013.01); *C07C 43/29* (2013.01); *C07D 213/30* (2013.01); *C07D 239/26* (2013.01); *C07D 309/06* (2013.01); *C07D 319/06* (2013.01); *C09K 19/3048* (2013.01); *C09K 19/3066* (2013.01); *C09K 19/3068* (2013.01); *C09K 19/322* (2013.01); *C09K 19/3458* (2013.01); *C09K 2019/0466* (2013.01); *C09K 2019/308* (2013.01); *C09K 2019/3019* (2013.01); *C09K 2019/3071* (2013.01); *C09K 2019/3077* (2013.01); *C09K 2019/325* (2013.01); *C09K 2019/326* (2013.01); *C09K 2019/3422* (2013.01)

(58) Field of Classification Search
CPC ............ C09K 19/3402; C09K 19/3458; C09K 19/3068; C09K 19/3048; C09K 19/3066; C09K 19/322; C09K 2019/3077; C09K 2019/3422; C09K 2019/3071; C09K 2019/0466; C09K 2019/3019; C09K 2019/308; C09K 2019/325; C09K 2019/326; G02F 1/1333; C07C 43/29; C07C 25/24; C07D 309/06; C07D 319/06; C07D 213/30; C07D 239/26

USPC .................................. 252/299.63; 428/1.1
See application file for complete search history.

(56) References Cited

U.S. PATENT DOCUMENTS

| | | | |
|---|---|---|---|
| 5,204,018 A | 4/1993 | Kelly | |
| 5,204,019 A | 4/1993 | Reiffenrath et al. | |
| 5,236,620 A | 8/1993 | Reiffenrath et al. | |
| 8,398,887 B2 * | 3/2013 | Hu ................... | C09K 19/3048 252/299.63 |

(Continued)

FOREIGN PATENT DOCUMENTS

| | | |
|---|---|---|
| DE | 3906058 A1 | 7/2015 |
| JP | H02503441 A | 10/1990 |

(Continued)

*Primary Examiner* — Geraldina Visconti
(74) *Attorney, Agent, or Firm* — Hogan Lovells US LLP

(57) ABSTRACT

To provide a liquid crystal compound satisfying at least one of high stability to heat, light and so forth, a high clearing point, low minimum temperature of a liquid-crystal phase, small viscosity, suitable optical anisotropy, large dielectric anisotropy, a suitable elastic constant and excellent compatibility with other liquid-crystal compounds, a liquid crystal composition containing the compound and a liquid crystal display device including the composition.

A compound is represented by formula (1-1).

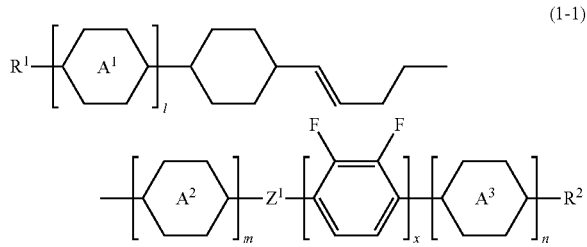

(1-1)

For example, $R^1$ and $R^2$ are independently hydrogen, alkyl having 1 to 10 carbons, alkenyl having 3 to 10 carbons and alkoxy having 1 to 9 carbons; ring $A^1$ is 1,4-cyclohexylene; ring $A^2$ and ring $A^3$ are independently 1,4-cyclohexylene or 1,4-phenylene; $Z^1$ is a single bond or $-(CH_2)_2$-; l is 0 or 1, m and n are 0, 1 or 2, a sum: $l+m+n$ is 0, 1 or 2; x is 0 or 1.

9 Claims, No Drawings

(56) References Cited

U.S. PATENT DOCUMENTS 8,580,146 B2 * 11/2013 Kobayashi ......... C09K 19/3048
                                                  252/299.01
2004/0065866 A1    4/2004 Kato et al.

FOREIGN PATENT DOCUMENTS

| JP | H04330019 A | 11/1992 |
| JP | 200053602 A | 2/2000 |
| WO | 89-08633 A1 | 9/1989 |
| WO | 89-08687 A1 | 9/1989 |
| WO | 89-08689 A1 | 9/1989 |

* cited by examiner

LIQUID CRYSTAL COMPOUND HAVING BUTENE-BONDING GROUP, LIQUID CRYSTAL COMPOSITION AND LIQUID CRYSTAL DISPLAY DEVICE

TECHNICAL FIELD

The invention relates to a liquid crystal compound, a liquid crystal composition and a liquid crystal display device. More specifically, the invention relates to a 2,3-difluorobenzene derivative having a butene-bonding group, a liquid crystal composition that contains the compound and has a nematic phase, and a liquid crystal display device including the composition.

BACKGROUND ART

A liquid crystal display device has been widely used for a display of a personal computer, a television or the like. The device utilizes optical anisotropy, dielectric anisotropy and so forth of a liquid crystal compound. As an operating mode of the liquid crystal display device, such a mode is known as a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode, a fringe field switching (FFS) mode and a polymer sustained alignment (PSA) mode.

Among the modes, the IPS mode, the FFS mode and the VA mode are known to improve narrowness of a viewing angle, being a disadvantage of the operating mode such as the TN mode and the STN mode. In the liquid crystal display device having the mode of the kind, a liquid crystal composition having a negative dielectric anisotropy is mainly used. In order to further improve characteristics of the liquid crystal display device, a liquid crystal compound contained in the composition preferably has physical properties described in (1) to (8) below.

(1) High stability to heat, light and so forth,
(2) a high clearing point,
(3) low minimum temperature of a liquid crystal phase,
(4) small viscosity ($\eta$),
(5) suitable optical anisotropy ($\Delta n$),
(6) large negative dielectric anisotropy ($\Delta \varepsilon$),
(7) a suitable elastic constant ($K_{33}$: bend elastic constant) and
(8) excellent compatibility with other liquid crystal compounds.

An effect of physical properties of the liquid crystal compound on the characteristics of the device is as described below. A compound having the high stability to heat, light and so forth as described in (1) increases a voltage holding ratio of the device. Thus, a service life of the device becomes longer. A compound having the high clearing point as described in (2) extends a temperature range in which the device can be used. A compound having the low minimum temperature of the liquid crystal phase such as a nematic phase and a smectic phase as described in (3), in particular, a compound having the low minimum temperature of the nematic phase, also extends the temperature range in which the device can be used. A compound having the small viscosity as described in (4) decreases a response time of the device.

A compound having the suitable optical anisotropy as described in (5) improves contrast of the device. According to a design of the device, a compound having a large optical anisotropy or a small optical anisotropy, more specifically, a compound having the suitable optical anisotropy is required. When the response time is shortened by decreasing a cell gap of the device, a compound having the large optical anisotropy is suitable. A compound having the large negative dielectric anisotropy as described in (6) decreases a threshold voltage of the device. Thus, an electric power consumption of the device is reduced.

With regard to (7), a compound having a large elastic constant decreases the response time of the device. A compound having a small elastic constant decreases the threshold voltage of the device. Therefore, the suitable elastic constant is required according to the characteristics that are desirably improved. A compound having the excellent compatibility with other liquid crystal compounds as described in (8) is preferred. The reason is because the physical properties of the composition are adjusted by mixing liquid crystal compounds having different physical properties.

As a component of a liquid crystal composition that has a negative dielectric anisotropy and can be used for the liquid crystal display device of the operating mode described above, a number of liquid crystal compounds in which hydrogen on a benzene ring is replaced by fluorine have been studied so far.

For example, compound (A) in which hydrogen on a benzene ring is replaced by fluorine has been studied (see patent literature No. 1). However, the compound has a small optical anisotropy. In addition thereto, compound (B) having alkenyl in which hydrogen on a benzene ring is replaced by fluorine and has been studied (see patent literature No. 2). However, the optical anisotropy of the compound is far from sufficiently large.

Tricyclic compound (C) having an ether-bonding group has been shown (see patent literature No. 3 and Non-patent literature No. 1). In the compound, a range (mesophase range) in which the liquid crystal phase is exhibited is narrow, and the clearing point when the compound is formed into the liquid crystal composition is low.

Tetracyclic compound (D) having an ethylene-bonding group has been shown (see patent literature No. 4). However, in the compound, the dielectric anisotropy is far from sufficiently negatively large and the clearing point when the compound is formed into the liquid crystal composition is low.

Tetracyclic compound (E) having an ether-bonding group and an ethylene-bonding group has been shown (see patent literature No. 5). However, in the compound, the clearing point when the compound is formed into the liquid crystal composition is low.

Tricyclic compound (F) having a butenyl group and an ester-bonding group has been shown (see patent literature No. 6). However, in the compound, the dielectric anisotropy is far from sufficiently negatively large negative dielectric anisotropy, the viscosity is also high, and the clearing point when the composition is formed into the liquid crystal composition is also low.

Thus, the compounds are far from sufficiently suitable for the mode of the liquid crystal display device in recent years.

In a new compound, excellent physical properties that are not found in a conventional compound can be expected. The new compound is expected to have a suitable balance between two physical properties required upon preparing the liquid crystal composition. In view of such a situation, development has been desired for a compound having excellent physical properties and a suitable balance regarding the physical properties with regard to (1) to (8) as described above.

CITATION LIST

Patent Literature

Patent literature No. 1: JP H02-503441 A.
Patent literature No. 2: JP 2000-53602 A.
Patent literature No. 3: DE 3906058 A.
Patent literature No. 4: WO 1989/08687 A.
Patent literature No. 5: WO 1989/08689 A.
Patent literature No. 6: JP H04-330019 A.
Non-patent literature No. 1: Liquid Crystals (1994), 16(4), 625-641.

SUMMARY OF INVENTION

Technical Problem

Accordingly, even a liquid crystal display device having an operating mode such as an IPS mode and a VA mode still has a problem to be solved as the display device if the device is compared with a CRT. For example, an improvement in response speed, an improvement in contrast, and a decrease of driving voltage have been desired.

The display device that operates in the IPS mode or the VA mode is mainly composed of a liquid crystal composition having a negative dielectric anisotropy. In order to further improve characteristics, the liquid crystal compound contained in the liquid crystal composition is required to have the characteristics described in items (1) to (8) below. More specifically, the compound should:

(1) be chemically stable and physically stable;
(2) have a high clearing point (a transition temperature between a liquid crystal phase and an isotropic phase);
(3) have a low minimum temperature of the liquid crystal phase (a nematic phase, a smectic phase or the like), in particular, a low minimum temperature of the nematic phase;
(4) have a small viscosity;
(5) have a suitable optical anisotropy;
(6) have a negatively high dielectric anisotropy;
(7) have a suitable elastic constant $K_{33}$ ($K_{33}$: bend elastic constant), and
(8) have an excellent compatibility with other liquid crystal compounds.

If a composition containing the liquid crystal compound being chemically and physically stable as described in (1) is used for the display device, a voltage holding ratio can be increased. In a composition containing the liquid crystal compound having the high clearing point or the low minimum temperature of the liquid crystal phase as described in (2) and (3), a temperature range of the nematic phase can be extended, and the composition can be used in a wide temperature range in the form of the display device.

If a composition containing the compound having the small viscosity as described in (4) and a compound having the large elastic constant $K_{33}$ as described in (7) are used for the display device, the response speed can be improved. In the case of the display device in which a composition containing the compound having the suitable optical anisotropy as described in (5) is used, contrast in the display device can be increased. Depending on device design, the display device requires a composition having a small optical anisotropy to a composition having a large optical anisotropy. Study has been recently conducted on a technique for improving the response speed by decreasing a cell thickness, and in connection therewith, a liquid crystal composition having the large optical anisotropy has been required.

When the liquid crystal compound has a negatively high dielectric anisotropy, threshold voltage of a liquid crystal composition containing the compound can be decreased. Thus, in the case of the display device in which the composition containing the compound having the negatively high dielectric anisotropy as described in (6) is used, drive voltage of the display device can be decreased and electric power consumption can also be reduced. The drive voltage of the display device can be decreased and the electric power consumption can also be reduced by using a composition containing the compound having the small elastic constant $K_{33}$ as described in (7) in the form of the display device.

In order to develop the characteristics that are difficult to be exhibited by a single compound, the liquid crystal compound is generally used in the form of a composition prepared by mixing the compound with a number of other liquid crystal compounds. Accordingly, the liquid crystal compound to be used for the display device has preferably a good compatibility with other liquid crystal compounds and so forth as described in (8). The display device is used in the wide temperature range including temperature below a freezing point in several cases, and therefore the compound preferably has a good compatibility from the low temperature.

A first aim of the invention is to provide a liquid crystal compound having a high stability to heat, light and so forth, forming a nematic phase in a wide temperature range, having a small viscosity, a large optical anisotropy and a large elastic constant $K_{33}$, and further having a large negative dielectric anisotropy and an excellent compatibility with other liquid crystal compounds.

A second aim of the invention is to provide a liquid crystal composition that contains the compound, and has a high stability to heat, light and so forth, a low viscosity, a suitable optical anisotropy, a negatively high dielectric anisotropy, a large elastic constant $K_{33}$, a low threshold voltage, a high maximum temperature of a nematic phase and a low minimum temperature of the nematic phase.

A third aim of the invention is to provide a liquid crystal display device that includes the composition, has a short response time, a small electric power consumption, a small drive voltage and a large contrast, and can be used in a wide temperature range.

Solution to Problem

In view of the problems described above, the present inventors have diligently continued to conduct research, as a result, have found that a 2,3-difluorobenzene derivative having a cyclohexene ring or a phenyl ring and a butene-bonding group has a high stability to heat, light and so forth, forms a nematic phase in a wide temperature range, has a small viscosity, a suitable optical anisotropy and a large elastic constant $K_{33}$, and further has a negatively high dielectric anisotropy and an excellent compatibility with other liquid crystal compound. The present inventors have found that a liquid crystal composition containing the compound has a high stability to heat, light and so forth, a small viscosity, a suitable optical anisotropy, a large elastic constant $K_{33}$ and a suitable negative dielectric anisotropy, and has a low threshold voltage, a high maximum temperature of a nematic phase, and a low minimum temperature of the nematic phase. Moreover, the present inventors have found that a liquid crystal display device including the composition has a short response time, a small electric power consumption and drive voltage and a large contrast ratio, and can be used in a wide temperature range, and thus have completed the invention.

The invention includes items as described in items 1 to 14 as described below and so forth.

The invention concerns a compound represented by formula (1-1), a liquid crystal composition containing the compound, and a liquid crystal display device including the composition.

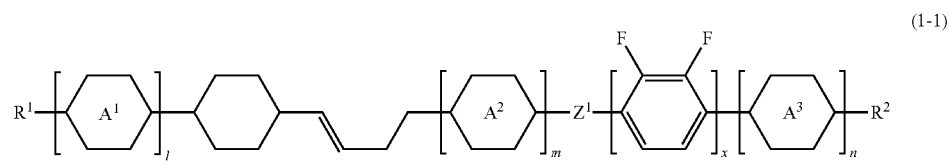

(1-1)

In formula (1-1), $R^1$ and $R^2$ are independently hydrogen, alkyl having 1 to 10 carbons, alkenyl having 3 to 10 carbons, alkoxy having 1 to 9 carbons, alkoxyalkyl having 2 to 9 carbons or alkenyloxy having 2 to 9 carbons;

ring $A^1$ is 1,4-cyclohexylene, tetrahydropyran-2,5-diyl, 1,3-dioxane-2,5-diyl, pyrimidine-2,5-diyl, pyridine-2,5-diyl, naphthalene-2,6-diyl, decahydronaphthalene-2,6-diyl, 1,2,3,4-tetrahydronaphthalene-2,6-diyl or 2,3-difluoro-1,4-phenylene;

ring $A^2$ and ring $A^3$ are independently 1,4-cycloxylene, tetrahydropyran-2,5-diyl, 1,3-dioxane-2,5-diyl, pyrimidine-2,5-diyl, pyridine-2,5-diyl, naphthalene-2,6-diyl, decahydronaphthalene-2,6-diyl, 1,2,3,4-tetrahydronaphthalene-2,6-diyl, 1,4-phenylene, 2-fluoro-1,4-phenylene or 2,3-difluoro-1,4-phenylene;

$Z^1$ is a single bond, —$(CH_2)_2$—, —$CH_2O$—, —$OCH_2$—, —$CF_2O$— or —$OCF_2$—;

l is 0 or 1, m and n are 0, 1 or 2, and a sum: l+m+n is 0, 1 or 2;

x is 0 or 1; and when l is 1 and ring $A^1$ is 2,3-difluoro-1,4-phenylene, x is 0, and ring $A^2$ and ring $A^3$ are independently 1,4-cyclohexylene, tetrahydropyran-2,5-diyl, 1,3-dioxane-2,5-diyl, pyrimidine-2,5-diyl, pyridine-2,5-diyl, naphthalene-2,6-diyl, decahydronaphthalene-2,6-diyl, 1,2,3,4-tetrahydronaphthalene-2,6-diyl or 2-fluoro-1,4-phenylene; and when l is 1 and ring $A^1$ is 1,4-cycloxylene, x is 1 and a sum: m+n is 1.

The invention also concerns use of the compound as a component of a liquid crystal composition.

Advantageous Effects of Invention

A first advantage of the invention is to provide a liquid crystal compound having a high stability to heat, light and so forth, a high clearing point, a low minimum temperature of a liquid crystal phase, a small viscosity, a suitable optical anisotropy, a large negative dielectric anisotropy, a suitable elastic constant and an excellent compatibility with other liquid crystal compounds. The advantage is to provide a compound having a particularly large negative dielectric anisotropy. The advantage is to provide a compound having a particularly excellent compatibility. A second advantage is to provide a liquid crystal composition that contains the compound and has a high maximum temperature of a nematic phase, a low minimum temperature of the nematic phase, a small viscosity, a suitable optical anisotropy, a large negative dielectric anisotropy and a suitable elastic constant. The advantage is a liquid crystal composition having a suitable balance regarding at least two of physical properties. A third advantage is to provide a liquid crystal display device that includes the composition and has a wide temperature range in which the device can be used, a short response time, a large voltage holding ratio, a low threshold voltage, a large contrast ratio and a long service life.

DESCRIPTION OF EMBODIMENTS

Usage of terms herein is as described below. A liquid crystal compound is a generic term for a compound having a liquid crystal phase such as a nematic phase or a smectic phase, and also a compound having no liquid crystal phase but being useful as a component of the liquid crystal composition. The liquid crystal compound, the liquid crystal composition and a liquid crystal display device may be occasionally abbreviated as "compound," "composition" and "device," respectively. The liquid crystal display device is a generic term for a liquid crystal display panel and a liquid crystal display module. A clearing point is a transition temperature between the liquid crystal phase and an isotropic phase in the liquid crystal compound. A minimum temperature of the liquid crystal phase is a transition temperature between a solid and the liquid crystal phase (the smectic phase, the nematic phase or the like) in the liquid crystal compound. A maximum temperature of the nematic phase is a transition temperature between the nematic phase and the isotropic phase in the liquid crystal composition, and may be occasionally abbreviated as "maximum temperature." A minimum temperature of the nematic phase may be occasionally abbreviated as "minimum temperature." The compound represented by formula (1) may be occasionally abbreviated as "compound (1)." The abbreviation may apply occasionally also to a compound represented by formula (2) or the like. In formula (1), formula (2) or the like, a symbol $A^1$, $D^1$ or the like surrounded by a hexagonal shape corresponds to ring $A^1$, ring $D^1$ or the like, respectively. A plurality of rings $A^1$ are described in one formula or in different formulas. In the compounds, two groups represented by two of arbitrary ring $A^1$ may be identical or different. A same rule also applies to a symbol ring $A^2$, $Z^2$ or the like. Moreover, the same rule also applies to two of ring $A^1$ when l is 2. An amount of a compound expressed in terms of "percent" is expressed in terms of "weight percent (% by weight)" based on the total amount of the composition.

An expression "at least one of "A" may be replaced by "B"" means that a position of "A" when the number of "A" is 1 is arbitrary, and the positions thereof also when the number of "A" is 2 or more can be selected without limitation. An expression "at least one of A may be replaced by B, C or D" means inclusion of a case where arbitrary A is replaced by B, a case where arbitrary A is replaced by C, a case where arbitrary A is replaced by D, and further a case where a plurality of A are replaced by at least two of B, C and D. For example, alkyl in which at least one of —$CH_2$— may be replaced by —O— or —CH=CH— includes alkyl, alkenyl, alkoxy, alkoxyalkyl, alkoxyalkenyl and alkenyloxyalkyl. In addition, a case where replacement of two successive —$CH_2$— by —O— results in forming —O—O— is not preferred. In alkyl or the like, a case where replacement of —$CH_2$— of a methyl part (—$CH_2$—H) by —O— results in forming —O—H is not preferred, either.

Then, 2-fluoro-1,4-phenylene means two divalent groups described below. Fluorine may be leftward or rightward. A same rule also applies to an asymmetrical divalent group, such as tetrahydropyran-2,5-diyl.

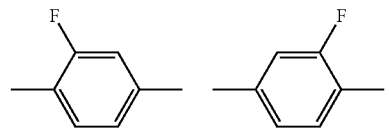

The invention includes the content as described in items 1 to 12 as described below.

Item 1. A compound represented by formula (1-1):

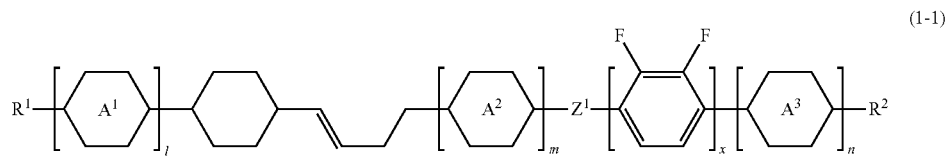

wherein, in formula (1-1), $R^1$ and $R^2$ are independently hydrogen, alkyl having 1 to 10 carbons, alkenyl having 3 to 10 carbons, alkoxy having 1 to 9 carbons, alkoxyalkyl having 2 to 9 carbons, or alkenyloxy having 2 to 9 carbons;

ring $A^1$ is 1,4-cyclohexylene, tetrahydropyran-2,5-diyl, 1,3-dioxane-2,5-diyl, pyrimidine-2,5-diyl, pyridine-2,5-diyl, naphthalene-2,6-diyl, decahydronaphthalene-2,6-diyl, 1,2,3,4-tetrahydronaphthalene-2,6-diyl or 2,3-difluoro-1,4-phenylene;

ring $A^2$ and ring $A^3$ are independently 1,4-cyclohexylene, tetrahydropyran-2,5-diyl, 1,3-dioxane-2,5-diyl, pyrimidine-2,5-diyl, pyridine-2,5-diyl, naphthalene-2,6-diyl, decahydronaphthalene-2,6-diyl, 1,2,3,4-tetrahydronaphthalene-2,6-diyl, 1,4-phenylene, 2-fluoro-1,4-phenylene or 2,3-difluoro-1,4-phenylene;

$Z^1$ is a single bond, —(CH$_2$)$_2$—, —CH$_2$O—, —OCH$_2$—, —CF$_2$O— or —OCF$_2$—;

l is 0 or 1, m and n are 0, 1 or 2, and a sum: l+m+n is 0, 1 or 2;

x is 0 or 1; and when l is 1 and ring $A^1$ is 2,3-difluoro-1,4-phenylene, x is 0, and ring $A^2$ and ring $A^3$ are independently 1,4-cyclohexylene, tetrahydropyran-2,5-diyl, 1,3-dioxane-2,5-diyl, pyrimidine-2,5-diyl, pyridine-2,5-diyl, naphthalene-2,6-diyl, decahydronaphthalene-2,6-diyl, 1,2,3,4-tetrahydronaphthalene-2,6-diyl or 2-fluoro-1,4-phenylene; and when l is 1 and ring $A^1$ is 1,4-cyclohexylene, x is 1 and a sum: m+n is 1.

Item 2. The compound according to item 1, represented by formula (1-2):

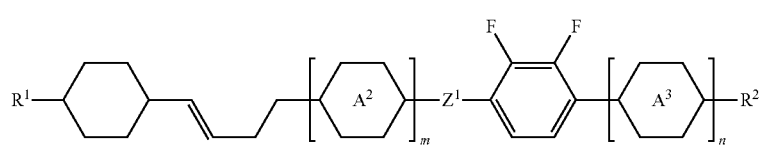

(1-2)

wherein, in formula (1-2), $R^1$ and $R^2$ are independently hydrogen, alkyl having 1 to 10 carbons, alkenyl having 3 to 10 carbons, alkoxy having 1 to 9 carbons, alkoxyalkyl having 2 to 9 carbons or alkenyloxy having 2 to 9 carbons;

ring $A^2$ and ring $A^3$ are independently 1,4-cyclohexylene, 1,4-cyclohexenylene, tetrahydropyran-2,5-diyl, 1,4-phenylene, 2-fluoro-1,4-phenylene, 3-fluoro-1,4-phenylene or 2,3-difluoro-1,4-phenylene;

$Z^1$ is a single bond, —(CH$_2$)$_2$—, —CH$_2$O—, —OCH$_2$— —CF$_2$O— or —OCF$_2$—;

m and n are 0, 1 or 2, and a sum: m+n is 0, 1 or 2.

Item 3. The compound according to item 1, represented by formula (1-3):

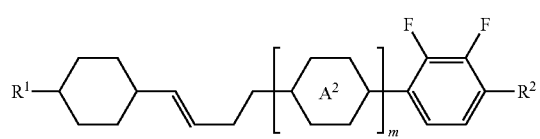

(1-3)

wherein, in formula (1-3), $R^1$ and $R^2$ are independently hydrogen, alkyl having 1 to 10 carbons, alkenyl having 3 to 10 carbons, alkoxy having 1 to 9 carbons, alkoxyalkyl having 2 to 9 carbons, or alkenyloxy having 2 to 9 carbons;

ring $A^2$ is 1,4-cyclohexylene, 1,4-cyclohexenylene, tetrahydropyran-2,5-diyl, 1,4-phenylene, 2-fluoro-1,4-phenylene, 3-fluoro-1,4-phenylene or 2,3-difluoro-1,4-phenylene; and m is 0 or 1.

Item 4. The compound according to item 1, represented by any one of formulas (1-4-1) to (1-4-6):

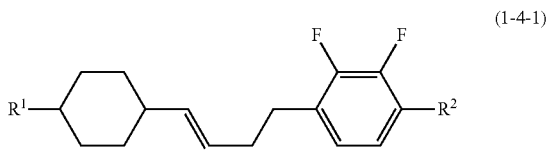

(1-4-1)

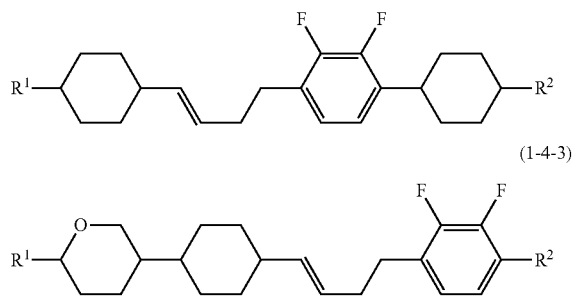

(1-4-2)

(1-4-3)

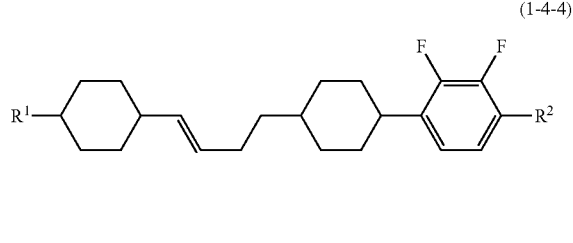

(1-4-4)

(1-4-5)

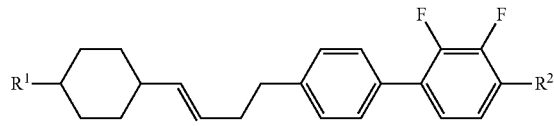

(1-4-6)

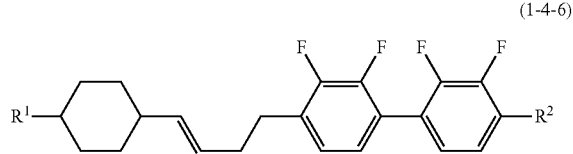

wherein, in formulas (1-4-1) to (1-4-6), $R^1$ and $R^2$ are independently hydrogen, alkyl having 1 to 10 carbons, alkenyl having 3 to 10 carbons, alkoxy having 1 to 9 carbons, alkoxyalkyl having 2 to 9 carbons or alkenyloxy having 2 to 9 carbons.

Item 5. Use of at least one of the compounds according to any one of items 1 to 4 as a component of a liquid crystal composition.

Item 6. A liquid crystal composition, containing at least one compound according to any one of items 1 to 4.

Item 7. The liquid crystal composition according to item 6, further containing at least one compound selected from the group of compounds represented by each of formulas (2), (3) and (4):

(2)

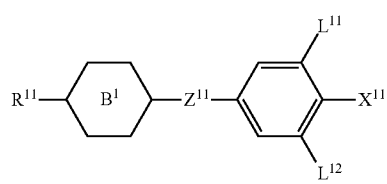

(3)

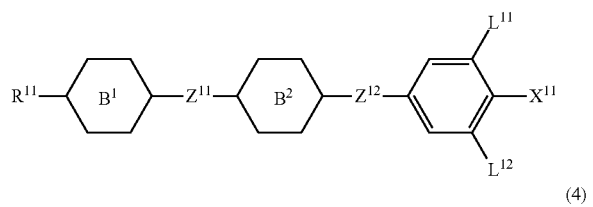

(4)

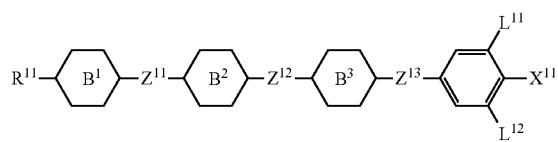

wherein, in formulas (2) to (4), $R^{11}$ is alkyl having 1 to 10 carbons or alkenyl having 2 to 10 carbons, and in the alkyl and alkenyl, at least one of hydrogen may be replaced by fluorine, and at least one of —$CH_2$— may be replaced by —O—;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $B^1$, ring $B^2$ and ring $B^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{11}$, $Z^{12}$, and $Z^{13}$ are independently a single bond, —$CH_2CH_2$—, —CH=CH—, —C≡C—, —COO—, —$CF_2O$—, —$OCF_2$—, —$CH_2O$— or —$(CH_2)_4$—; and $L^{11}$ and $L^{12}$ are independently hydrogen or fluorine.

Item 8. The liquid crystal composition according to item 6 or 7, further containing at least one compound selected from the group of compounds represented by formula (5):

(5)

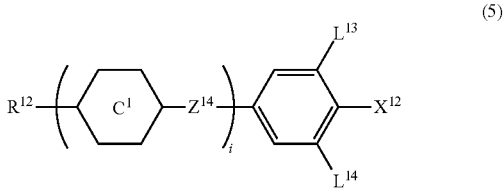

wherein, in formula (5), $R^{12}$ is alkyl having 1 to 10 carbons or alkenyl having 2 to 10 carbons, and in the alkyl and alkenyl, at least one of hydrogen may be replaced by fluorine and at least one of —$CH_2$— may be replaced by —O—;

$X^{12}$ is —C≡N or —C≡C—C≡N;

ring $C^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{14}$ is a single bond, —$CH_2CH_2$—, —C≡C—, —COO—, —$CF_2O$—, —$OCF_2$— or —$CH_2O$—;

$L^{13}$ and $L^{14}$ are independently hydrogen or fluorine; and i is 1, 2, 3 or 4.

Item 9. The liquid crystal composition according to any one of items 6 to 8, further containing at least one compound selected from the group of compounds represented by formulas (6) to (12):

(6)

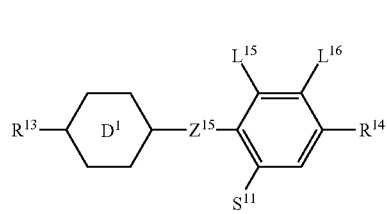

(7)

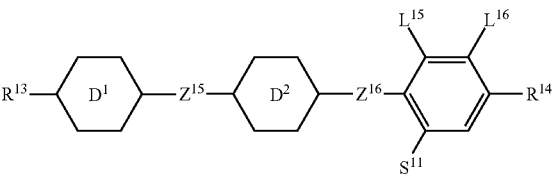

(8)

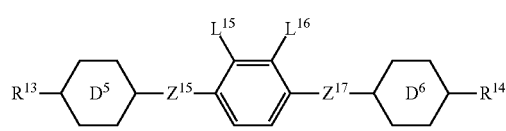

(9)

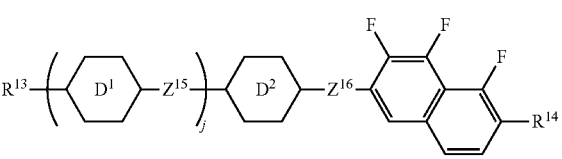

(10)

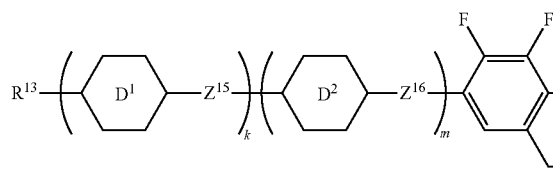

(11)

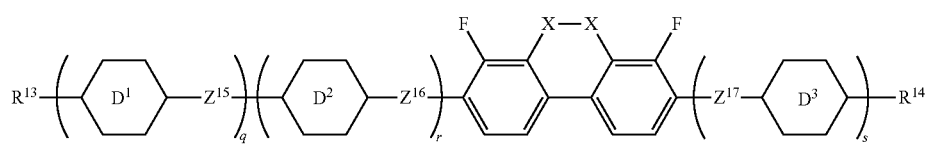

-continued (12)

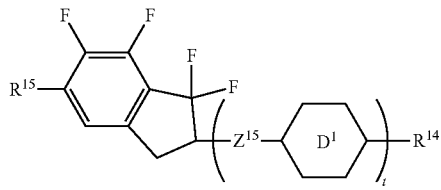

wherein, in formulas (6) to (12),
$R^{13}$ and $R^{14}$ are independently alkyl having 1 to 10 carbons or alkenyl having 2 to 10 carbons, and in the alkyl or the alkenyl, at least one of —$CH_2$— may be replaced by —O— and at least one of hydrogen may be replaced by fluorine;
$R^{15}$ is hydrogen, fluorine, alkyl having 1 to 10 carbons or alkenyl having 2 to 10 carbons, and in the alkyl and the alkenyl, at least one of —$CH_2$— may be replaced by —O— and at least one of hydrogen may be replaced by fluorine;
$S^{11}$ is hydrogen or methyl;
X is —$CF_2$—, —O— or —CHF—;
ring $D^1$, ring $D^2$, ring $D^3$ and ring $D^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;
ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;
$Z^{15}$, $Z^{16}$, $Z^{17}$ and $Z^{18}$ are independently a single bond, —$CH_2CH_2$—, —COO—, —$CH_2O$—, —$OCF_2$— or —$OCF_2CH_2CH_2$—;
$L^{15}$ and $L^{16}$ are independently fluorine or chlorine; and
j, k, m, n, p, q, r and s are independently 0 or 1, a sum of k, m, n and p is 1 or 2, a sum of q, r and s is 0, 1, 2 or 3, and t is 1, 2 or 3.

Item 10. The liquid crystal composition according to any one of items 6 to 9, further containing at least one compound selected from the group of compounds represented by formulas (13) to (15):

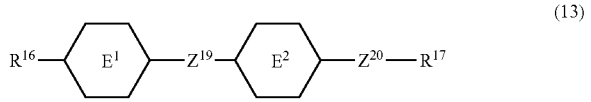

(13)

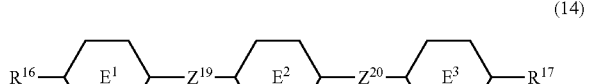

(14)

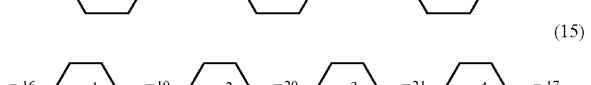

(15)

wherein, in formulas (13) to (15),
$R^{16}$ and $R^{17}$ are independently alkyl having 1 to 10 carbons or alkenyl having 2 to 10 carbons, and in the alkyl and the alkenyl, at least one of —$CH_2$— may be replaced by —O— and at least one of hydrogen may be replaced by fluorine;
ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene or pyrimidine-2,5-diyl; and
$Z^{19}$, $Z^{20}$ and $Z^{21}$ are independently a single bond, —$CH_2CH_2$—, —CH=CH—, —C≡C— or —COO—.

(13)

(14)

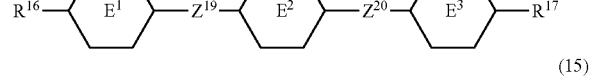

(15)

Item 11. The liquid crystal composition according to any one of items 6 to 10, further containing at least one optically active compound and/or at least one polymerizable compound.

Item 12. The liquid crystal composition according to any one of items 6 to 11, further containing at least one antioxidant and/or at least one ultraviolet light absorbent.

Item 13. A liquid crystal display device, including the liquid crystal composition according to any one of items 6 to 12.

The compound, the liquid crystal composition and the liquid crystal display device of the invention are described in the order.

1-1. Compound (1-1)
Compound (1-1) of the invention will be described. Preferred examples of a terminal group, a ring structure and a bonding group in compound (1-1), and an effect of the groups on physical properties also applies to a compound represented by a subordinate formula of formula (1-1) for compound (1-1):

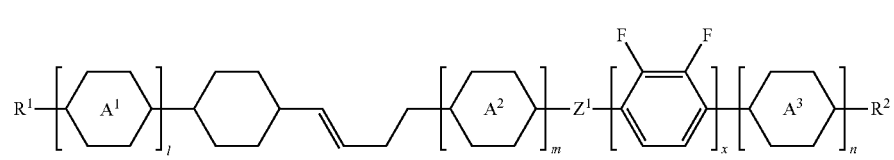

(1-1)

In formula (1-1), $R^1$ and $R^2$ are independently hydrogen, alkyl having 1 to 10 carbons, alkenyl having 3 to 10 carbons, alkoxy having 1 to 9 carbons, alkoxyalkyl having 2 to 9 carbons or alkenyloxy having 2 to 9 carbons. The groups have a straight chain or a branched chain, and include no cyclic group such as cyclohexyl. In the groups, the straight chain is preferred to the branched chain.

Preferred examples of $R^1$ or $R^2$ include alkyl, alkoxy, alkoxyalkyl and alkenyl. Further preferred examples of $R^1$ or $R^2$ include alkyl, alkoxy and alkenyl.

Specific examples of alkyl include —$CH_3$, —$C_2H_5$, —$C_3H_7$, —$C_4H_9$, —$C_5H_{11}$, —$C_6H_{13}$ and —$C_7H_{15}$. Specific examples of alkoxy include —$OCH_3$, —$OC_2H_5$, —$OC_3H_7$, —$OC_4H_9$, —$OC_5H_{11}$ and —$OC_6H_{13}$. Specific examples of alkoxyalkyl include —$CH_2OCH_3$, —$CH_2OC_2H_5$, —$CH_2OC_3H_7$, —$(CH_2)_2OCH_3$, —$(CH_2)_2OC_2H_5$, —$(CH_2)_2OC_3H_7$, —$(CH_2)_3OCH_3$, —$(CH_2)_4OCH_3$, and —$(CH_2)_5OCH_3$. Specific examples of alkenyl include —CH=$CHCH_3$, —$CH_2$CH=$CH_2$, —CH=$CHC_2H_5$, —$CH_2$CH=$CHCH_3$, —$(CH_2)_2$CH=$CH_2$, —CH=$CHC_3H_7$, —$CH_2$CH=$CHC_2H_5$, —$(CH_2)_2$CH=$CHCH_3$ and —$(CH_2)_3$CH=$CH_2$. Specific examples of alkenyloxy include —$OCH_2$CH=$CH_2$, —$OCH_2$CH=$CHCH_3$ and —$OCH_2$CH=$CHC_2H_5$.

Preferred examples of $R^1$ or $R^2$ include —$CH_3$, —$C_2H_5$, —$C_3H_7$, —$C_4H_9$, —$C_5H_{11}$, —$OCH_3$, —$OC_2H_5$, —$OC_3H_7$, —$OC_4H_9$, —$OC_5H_{11}$, —$CH_2OCH_3$, —$(CH_2)_2OCH_3$, —$(CH_2)_3OCH_3$, —$CH_2$CH=$CH_2$, —$CH_2$CH=$CHCH_3$, —$(CH_2)_2$CH=$CH_2$, —$CH_2$CH=$CHC_2H_5$, —$(CH_2)_2$CH=$CHCH_3$, —$(CH_2)_3$CH=$CH_2$, —$(CH_2)_3$CH=$CHCH_3$, —$(CH_2)_3$CH=$CHC_2H_5$, —$(CH_2)_3$CH=$CHC_3H_7$, —$OCH_2$CH=$CH_2$, —$OCH_2$CH=$CHCH_3$ and —$OCH_2$CH=$CHC_2H_5$. Further preferred examples of $R^1$ or $R^2$ include —$CH_3$, —$C_2H_5$, —$C_3H_7$, —$OCH_3$, —$OC_2H_5$, —$OC_3H_7$, —$OC_4H_9$, —$(CH_2)_2$CH=$CH_2$, —$(CH_2)_2$CH=$CHCH_3$ and —$(CH_2)_2$CH=$CHC_3H_7$.

When $R^1$ or $R^2$ has the straight chain, a temperature range of the liquid crystal phase is wide and the viscosity is small. When $R^1$ or $R^2$ has the branched chain, compatibility with other liquid crystal compounds is good. A compound in which $R^1$ or $R^2$ is optically active is useful as a chiral dopant. A reverse twisted domain that is generated in the liquid crystal display device can be prevented by adding the compound to the composition. A compound in which $R^1$ or $R^2$ is not optically active is useful as a component of the composition.

A preferred configuration of —CH=CH— in alkenyl depends on a position of a double bond. A trans configuration is preferred in alkenyl having the double bond in an odd-numbered position, such as —CH=$CHCH_3$, —CH=$CHC_2H_5$, —CH=$CHC_3H_7$, —CH=$CHC_4H_9$, —$C_2H_4$CH=$CHCH_3$ and —$C_2H_4$CH=$CHC_2H_5$. A cis configuration is preferred in alkenyl having the double bond on an even-numbered position, such as —$CH_2$CH=$CHCH_3$, —$CH_2$CH=$CHC_2H_5$ and —$CH_2$CH=$CHC_3H_7$. The alkenyl compound having a preferred configuration has a wide temperature range of the liquid crystal phase, a small viscosity and a large elastic constant.

However, if stability of the compound is taken into consideration, a group in which oxygen and oxygen are adjacent, such as $CH_3$—O—O—$CH_2$—, or a group in which double bond sites are adjacent, such as $CH_3$—CH=CH—CH=CH—, are not preferred.

In formula (1-1), ring $A^1$ is 1,4-cyclohexylene, tetrahydropyran-2,5-diyl, 1,3-dioxane 2,5-diyl, pyrimidine-2,5-diyl, pyridine-2,5-diyl, naphthalene-2,6-diyl, decahydronaphthalene-2,6-diyl, 1,2,3,4-tetrahydronaphthalene-2,6-diyl or 2,3-difluoro-1,4-phenylene;

ring $A^2$ and ring $A^3$ are independently 1,4-cyclohexylene, 1,4-cyclohexenylene, tetrahydropyran-2,5-diyl, 1,3-dioxane 2,5-diyl, pyrimidine-2,5-diyl, pyridine-2,5-diyl, naphthalene-2,6-diyl, decahydronaphthalene-2,6-diyl, 1,2,3,4-tetrahydronaphthalene-2,6-diyl, 1,4-phenylene, 2-fluoro-1,4-phenylene or 2,3-difluoro-1,4-phenylene; and when l is 1 and ring $A^1$ is 2,3-difluoro-1,4-phenylene, x is 0, and ring $A^2$ and ring $A^3$ are independently 1,4-cyclohexylene, tetrahydropyran-2,5-diyl, 1,3-dioxane 2,5-diyl, pyrimidine-2,5-diyl, pyridine-2,5-diyl, naphthalene-2,6-diyl, decahydronaphthalene-2,6-diyl, 1,2,3,4-tetrahydronaphthalene-2,6-diyl and 2-fluoro-1,4-phenylene.

Preferred examples of ring $A^1$ include tetrahydropyran-2,5-diyl, naphthalene-2,6-diyl, decahydronaphthalene-2,6-diyl or 1,2,3,4-tetrahydronaphthalene-2,6-diyl. Preferred examples of ring $A^2$ or ring $A^3$ include 1,4-cyclohexylene, tetrahydropyran-2,5-diyl, 1,4-phenylene, 2-fluoro-1,4-phenylene or 2,3-difluoro-1,4-phenylene. Preferred examples of ring $A^1$ include tetrahydropyran-2,5-diyl, and preferred examples of ring $A^2$ or ring $A^3$ include 1,4-cyclohexylene or 1,4-phenylene. Then, 1,4-cyclohexylene has cis and trans configurations. From a viewpoint of a high maximum temperature, the trans configuration is preferred.

When ring $A^1$ is tetrahydropyran-2,5-diyl, an excellent compatibility with other liquid crystal compounds and a large negative dielectric anisotropy are exhibited. When the compound is added, compatibility of the composition can be increased, and the dielectric anisotropy can be negatively increased. When ring $A^1$ is naphthalene-2,6-diyl, refractive index anisotropy is large. When the compound is added, the refractive index anisotropy of the composition can be increased. Further, when ring $A^1$ is decahydronaphthalene-2,6-diyl or 1,2,3,4-tetrahydronaphthalene-2,6-diyl, the maximum temperature of the compound is large. When the compound is added, the maximum temperature of the composition can be increased.

When at least one of ring $A^2$ or ring $A^3$ is 1,4-cyclohexylene, the viscosity is small. When the compound is added, the viscosity of the composition can be decreased. When at least one of ring $A^2$ or ring $A^3$ is tetrahydropyran-2,5-diyl, the compound has the excellent compatibility with other liquid crystal compounds to exhibit a negatively large dielectric anisotropy. When the compound is added, the compatibility of the composition can be increased, and the dielectric anisotropy can be negatively increased. Further, when at least one of ring $A^2$ or ring $A^3$ is 1,4-phenylene, the maximum temperature and the refractive index anisotropy of the compound are large. When the compound is added, the maximum temperature and the refractive anisotropy of the composition can be increased. When at least one of ring $A^2$ and ring $A^3$ is 2,3-difluoro-1,4-phenylene, the dielectric anisotropy is negatively large. When the compound is added, the dielectric anisotropy of the composition can be negatively increased.

In formula (1-1), $Z^1$ is independently a single bond, —$(CH_2)_2$—, —$CH_2O$—, —$OCH_2$—, —$CF_2O$— or —$OCF_2$—.

A compound in which $Z^1$ is a single bond has a large maximum temperature, and therefore such a compound is preferred. A compound in which $Z^1$ is —$CH_2O$— or —$OCH_2$— has the large negative dielectric anisotropy, and therefore such a compound is preferred. A compound in which $Z^1$ is a single bond or —$(CH_2)_2$—, —$CF_2O$— or —$OCF_2$ has the small viscosity, and therefore such a compound is preferred.

If the stability of the compound is taken into consideration, a single bond, —(CH$_2$)$_2$—, —CH$_2$O— or —OCH$_2$— is preferred, and a single bond or —(CH$_2$)$_2$— is further preferred. When an increase of the clearing point of the compound is taken into consideration, a case where Z$^1$ is a single bond is most preferred.

In formula (1-1), l is 0 or 1, m and n are 0, 1 or 2, and a sum: l+m+n is 0, 1 or 2.

When the sum: l+m+n is 0, the viscosity is small. When the sum: l+m+n is 1, a balance between the viscosity and the maximum temperature is excellent. When the sum: l+m+n is 2, the maximum temperature is high.

In formula (1-1), x is 0 or 1. When x is 0, the maximum temperature is high. When x is 1, the dielectric anisotropy is negatively large.

Compound (1-1) has a butene-bonding group and 2,3-difluoro-1,4-phenylene. Due to an effect of such structure, the compound has a suitable optical anisotropy, a large negative dielectric anisotropy and a suitable elastic constant. The compound has the large negative dielectric anisotropy due to an effect of a fluorine-substituted alkenyl group. The compound is particularly excellent from viewpoints of the high maximum temperature and the large negative dielectric anisotropy.

As described above, a compound having objective physical properties can be obtained by suitably selecting types of the terminal groups, the ring structures, the bonding groups and so forth. Compound (1-1) may contain an isotope such as $^2$H (deuterium) and $^{13}$C in an amount larger than an amount of natural abundance because no significant difference is caused in physical properties of the compound.

1-2. Preferred Compound

Specific examples of preferred compound (1-1) include compound (1-2) described in item 2, compound (1-3) described in item 3 and compounds (1-4-1) to (1-4-6) described in item 4.

Compounds (1-1) to (1-3) have the butene-bonding group and 2,3-difluoro-1,4-phenylene, and are asymmetrical in the structure. Accordingly, the compounds are preferred from viewpoints of a high stability to heat or light, a low minimum temperature of the liquid crystal phase, the high maximum temperature of the liquid crystal phase, a large negative dielectric anisotropy and a suitable elastic constant. Compound (1-1) in which Z$^1$ is a single bond is further preferred from a viewpoint of the high maximum temperature. When Z$^1$ is —(CH$_2$)$_2$—, the compound is further preferred from a viewpoint of the small viscosity. When Z$^1$ is —CH$_2$O— or —OCH$_2$—, the compound is further preferred from a viewpoint of the large negative dielectric anisotropy.

Compounds (1-4-1) to (1-4-6) have the butene-bonding group and 2,3-difluoro-1,4-phenylene, and are asymmetrical in the structure. Accordingly, the compounds are preferred from viewpoints of the high stability to heat or light, the high maximum temperature of the liquid crystal phase, the low minimum temperature of the liquid crystal phase, the suitable optical anisotropy, the large negative dielectric anisotropy, the low viscosity, the high compatibility and the suitable elastic constant. Compound (1-4-1) is further preferred from viewpoints of the low viscosity and the high compatibility, compound (1-4-2) is further preferred from viewpoints of the high compatibility, compound (1-4-3) and (1-4-6) are further preferred from a viewpoint of the large negative dielectric anisotropy, compound (1-4-4) is further preferred from a viewpoint of the high maximum temperature, and compound (1-4-5) is further preferred from a viewpoint of the suitable optical anisotropy and the high compatibility.

A composition containing compound (1-1), in particular compounds (1-2) and (1-3) or compounds (1-4-1) to (1-4-6) has the high maximum temperature, the low minimum temperature, the small viscosity, the suitable optical anisotropy, the large negative dielectric anisotropy and the suitable elastic constant. The composition is stable under conditions in which the liquid crystal display device is ordinarily used, and even if the composition is kept at a low temperature, the compounds causes no precipitation as crystals (or the smectic phase). Accordingly, compound (1-1) can be preferably applied to the liquid crystal composition used for the liquid crystal display device having an operating mode such as IPS, VA or PSA.

1-3. Synthesis of Compound (1-1)

A method for synthesizing compound (1-1) will be described. Compound (1-1) can be prepared by suitably combining techniques in synthetic organic chemistry. A method for introducing an objective terminal group, ring and bonding group into a starting material is described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza, in Japanese) (Maruzen Co., Ltd.).

1-3-1. Formation of a Bonding Group

An example of a method for forming a bonding group in compound (1-1) is as described in a scheme below. In the scheme, MSG$^1$ (or MSG$^2$) is a monovalent organic group having at least one ring. Monovalent organic groups represented by a plurality of MSG$^1$ (or MSG$^2$) may be identical or different. Compounds (1A) to (1D) correspond to compound (1-1).

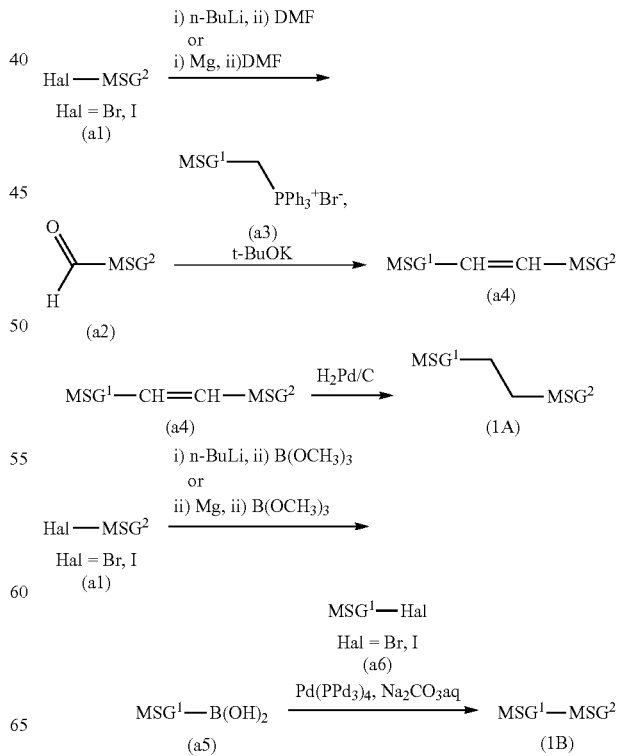

-continued

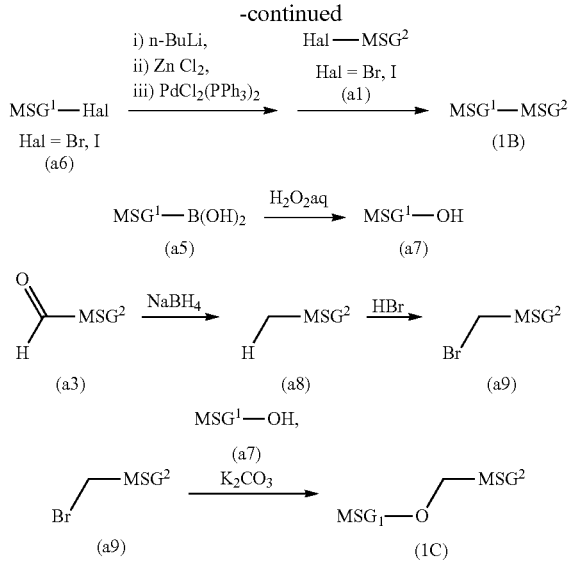

(1) Formation of —(CH$_2$)$_2$—

An intermediate, which is obtained from organohalogen compound (a1) by allowing with butyllithium (or magnesium), is reacted with formamide such as N,N-dimethylformamide (DMF), and aldehyde (a2) is obtained. The aldehyde (a2) is reacted with, phosphorus ylide obtained by treating phosphonium salt (a3) with a base such as potassium t-butoxide, and Compound (a4) having a double bond is obtained. Compound (1A) is prepared by hydrogenating compound (a4) in the presence of a catalyst such as palladium on carbon (Pd/C).

(2) Formation of a Single Bond

A Grignard reagent (or lithium salt) is prepared by allowing organohalogen compound (a1) to react with magnesium (or butyllithium). Dihydroxyborane (a5) is obtained, by allowing the Grignard reagent (or lithium salt) to react with a boric acid ester such as trimethyl borate and subsequently by hydrolyzing the resulting product in the presence of acid such as hydrochloric acid. Compound (1B) is prepared by allowing compound (a5) to react with organohalogen compound (a6) in an aqueous carbonate solution in the presence of a tetrakis(triphenylphosphine)palladium (Pd(PPh$_3$)$_4$) catalyst.

A method as described below is also available. Organohalogen compound (a6) is allowed to react with butyl lithium and additionally to react with zinc chloride. Compound (1B) is prepared by allowing the resulting intermediate to react with compound (a1) in the presence of bistriphenylphosphine dichloropalladium (Pd(PPh$_3$)$_2$Cl$_2$).

(3) Formation of —CH$_2$O— or —OCH$_2$—

Alcohol (a7) is obtained by oxidizing dihydroxyborane (a5) with an oxidizing agent such as hydrogen peroxide. Separately, alcohol (a8) is obtained by reducing aldehyde (a3) with a reducing agent such as sodium borohydride. Halogen compound (a9) is obtained by halogenating the alcohol (a8) with hydrobromic acid or the like. Compound (1C) is prepared by allowing the halide (a9) to react, in the presence of potassium carbonate or the like, with the alcohol (a7) previously obtained.

1-3-2. Preparation Example

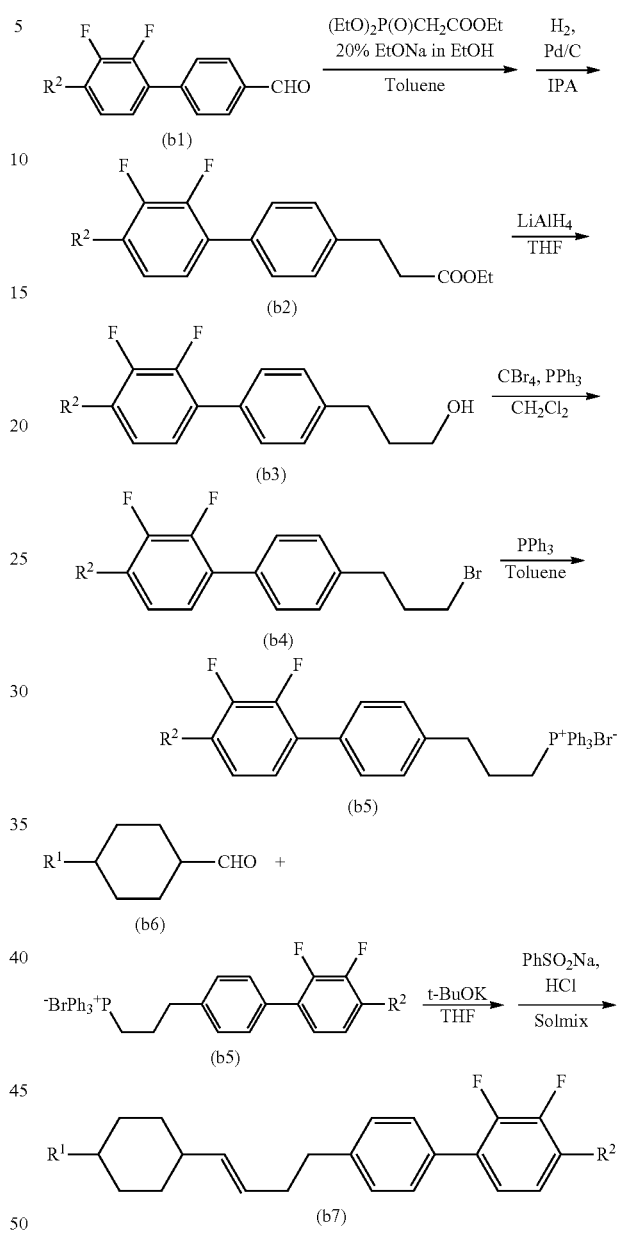

An example of a method for preparing compound (1-1) is described below. First, compound (b2) is obtained by allowing a benzaldehyde (b1) to react with ethyl diethylphosphonoacetate in the presence of sodium ethoxide and performing a hydrogenation reaction in the presence of a catalyst such as Pd/C. Subsequently, compound (b3) is obtained by reducing compound (b2) with lithium aluminum hydride or the like. Subsequently, compound (b4) is obtained by brominating by allowing compound (b3) to react with carbon tetrabromide and triphenylphosphine. Subsequently, compound (b5) is obtained by allowing compound (b4) to react with triphenylphosphine.

Mixture of a compound (b5) obtained by a process described above and an aldehyde derivative (b6) is reacted by witting reaction via phosphorus ylide in the presence of a base such as potassium t-butoxide (t-BuOK), and then isomerized in the presence of both sodium benzenesulfonate and hydrochloric acid, and finally, compound (b7), which is one of the example of compound (1-1) of the present invention, is synthesized.

2. Composition

A liquid crystal composition of the invention will be described below. The composition contains at least one compound (1) as component A. The composition may contain two or more kinds of compound (1). A component of the liquid crystal composition may be compound (1) only. The composition preferably contains at least one of compounds (1) in the range of approximately 1 to approximately 99% by weight in order to develop excellent physical properties. In a composition having a positive dielectric anisotropy, a preferred content of compound (1) is in the range of approximately 5 to approximately 60% by weight. In a composition having a negative dielectric anisotropy, a preferred content of compound (1) is approximately 30% or less by weight. The composition may also contain compound (1) and various kinds of liquid crystal compounds that are not described herein.

A preferred composition contains a compound selected from components B, C, D and E shown below. When the composition is prepared, a component thereof can be selected, for example, by taking dielectric anisotropy of compound (1) into consideration. A composition prepared by suitably selecting the components has the high maximum temperature of the nematic phase, the low minimum temperature of the nematic phase, the small viscosity, the suitable optical anisotropy, the large dielectric anisotropy and the suitable elastic constant.

Component B includes compounds (2) to (4). Component C is compound (5). Component D includes compounds (6) to (12). Component E includes compounds (13) to (15). The components will be described in the order.

Component B is a compound having a halogen-containing group or a fluorine-containing group at a right terminal. Preferred examples of component B include compounds (2-1) to (2-16), compounds (3-1) to (3-113) and compounds (4-1) to (4-57).

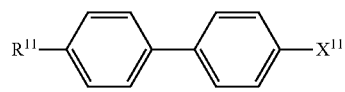
(2-1)

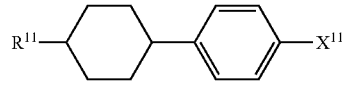
(2-2)

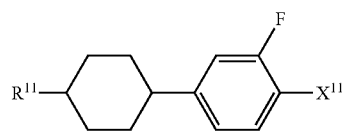
(2-3)

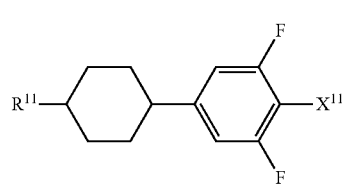
(2-4)

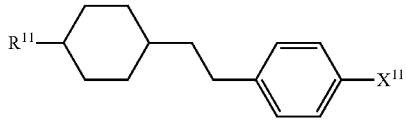
(2-5)

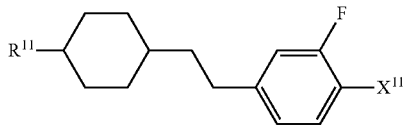
(2-6)

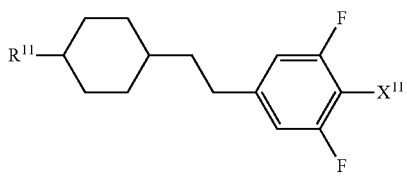
(2-7)

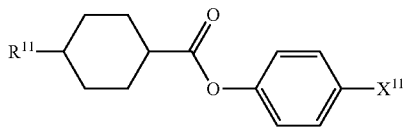
(2-8)

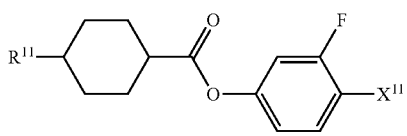
(2-9)

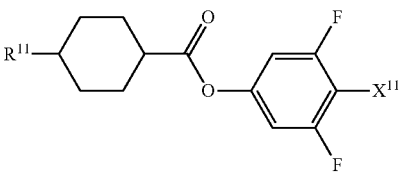
(2-10)

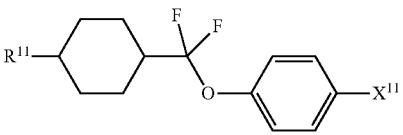
(2-11)

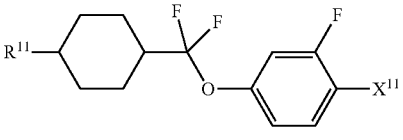
(2-12)

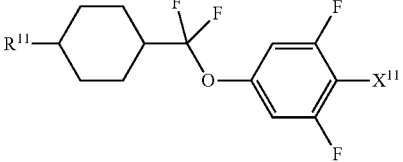
(2-13)

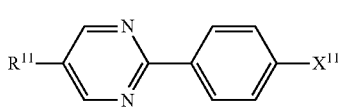
(2-14)

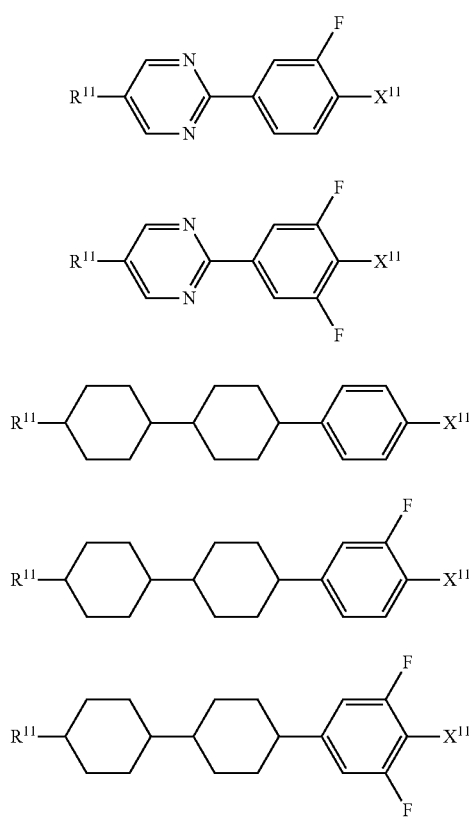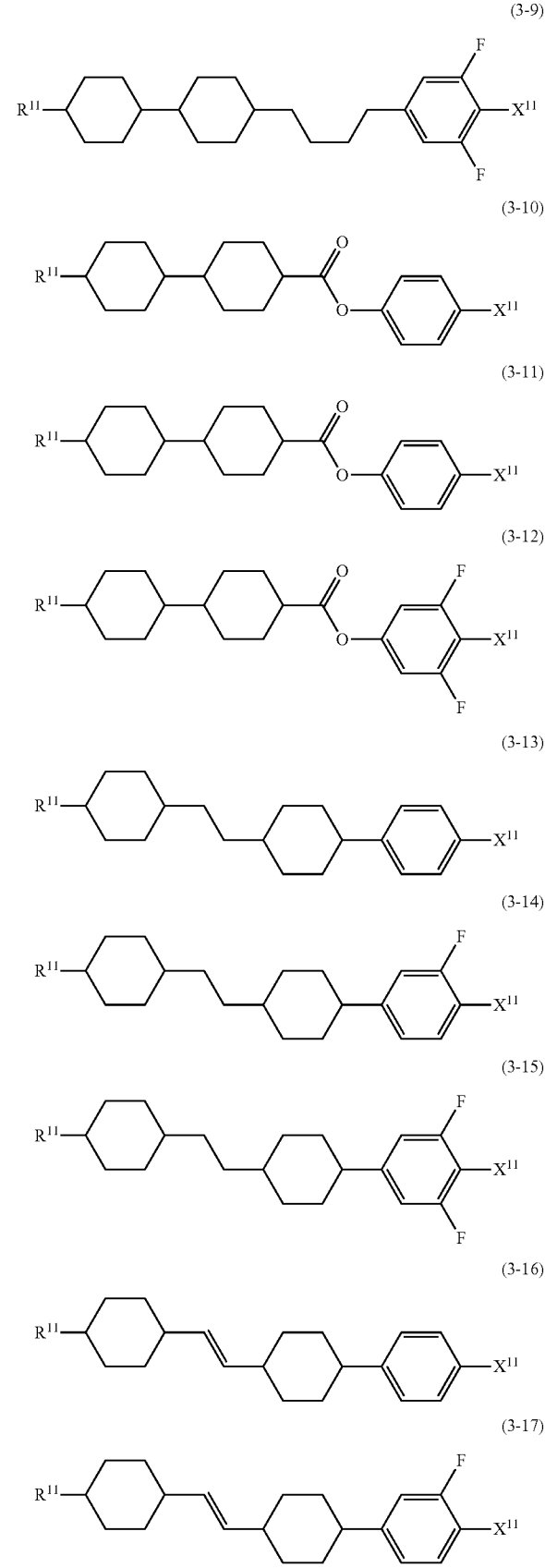

(3-18)
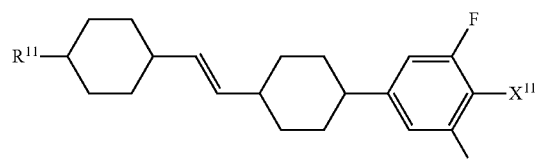
(3-19)
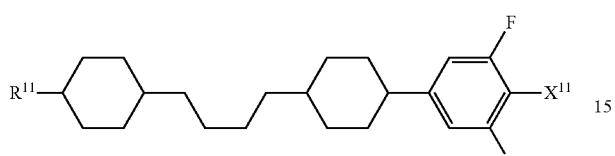
(3-20)
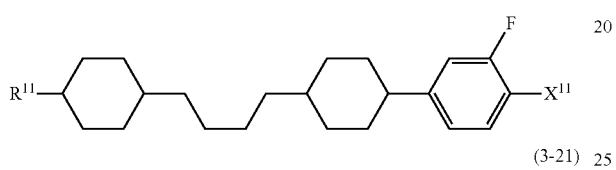
(3-21)
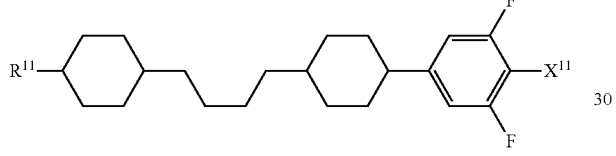
(3-22)
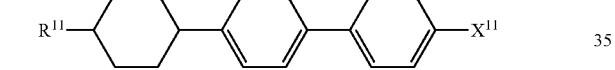
(3-23)
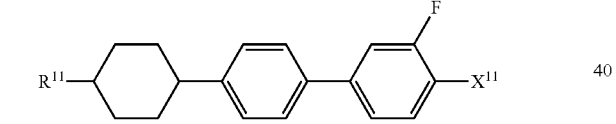
(3-24)
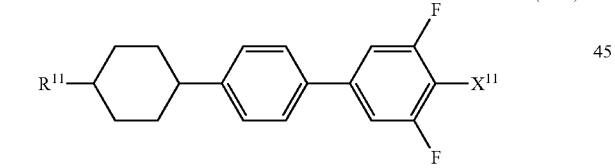
(3-25)
(3-26)
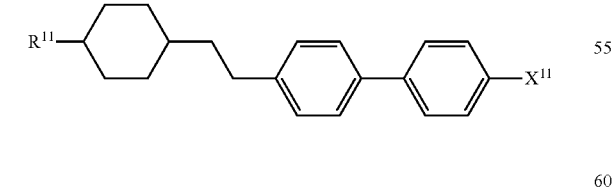
(3-27)
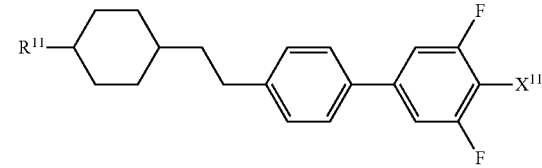
(3-28)
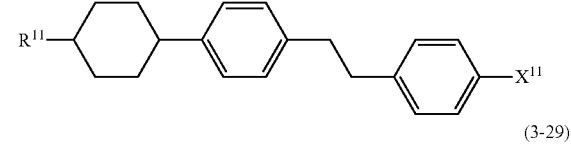
(3-29)
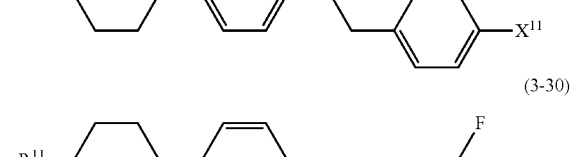
(3-30)
(3-31)
(3-32)
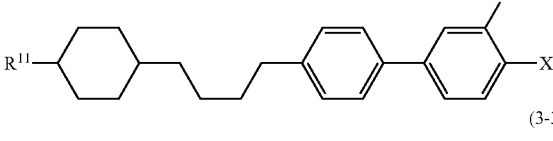
(3-33)
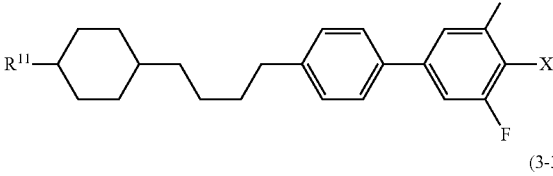
(3-34)
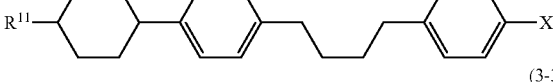
(3-35)
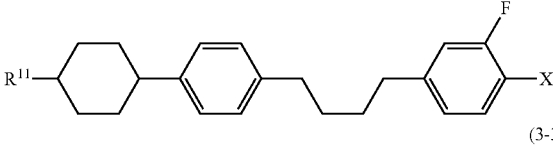
(3-36)
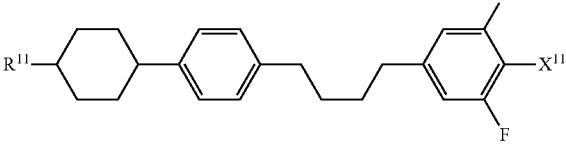

(3-37) 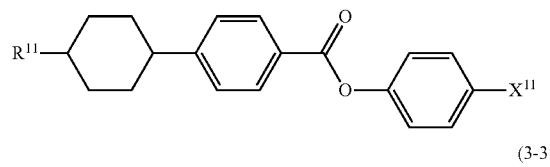
(3-38) 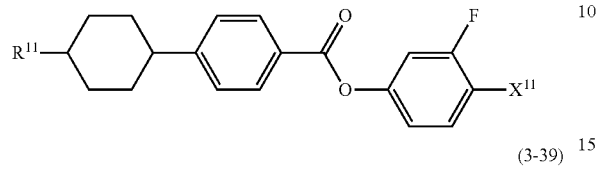
(3-39) 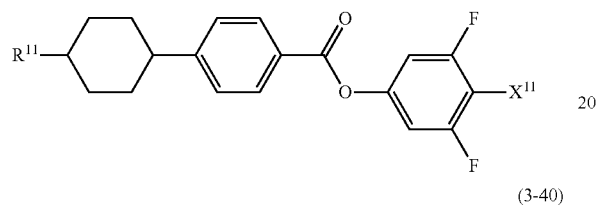
(3-40) 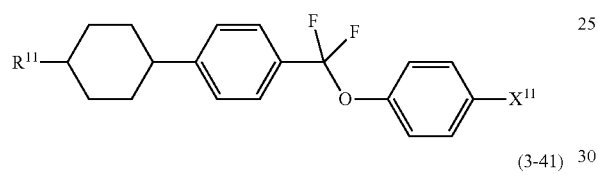
(3-41) 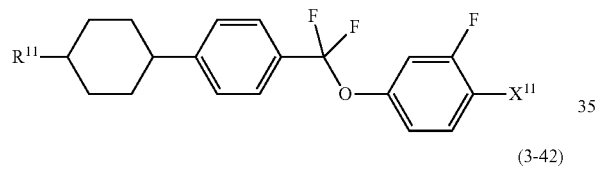
(3-42) 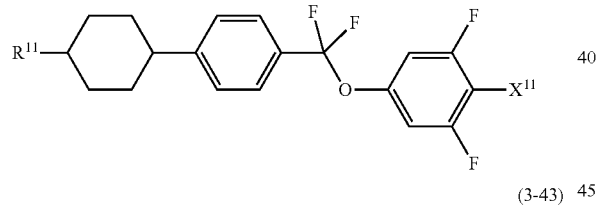
(3-43) 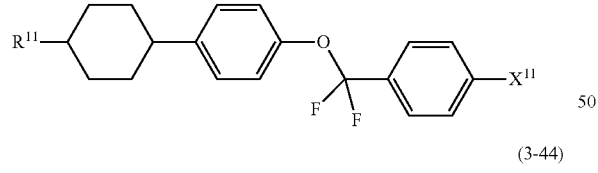
(3-44) 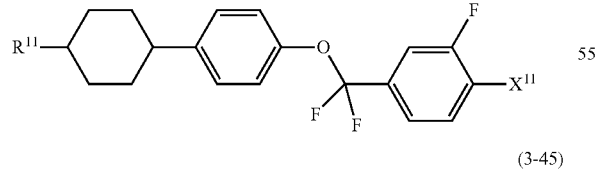
(3-45) 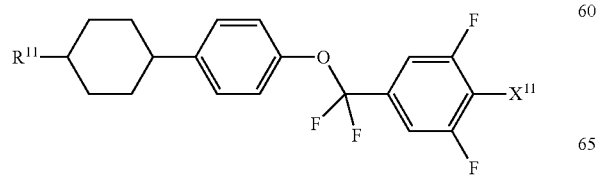
(3-46) 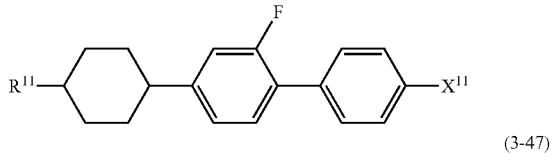
(3-47) 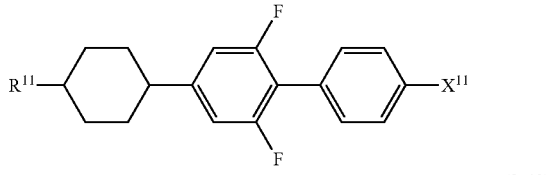
(3-48) 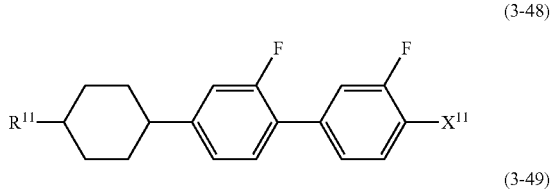
(3-49) 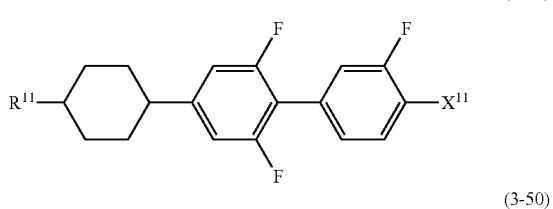
(3-50) 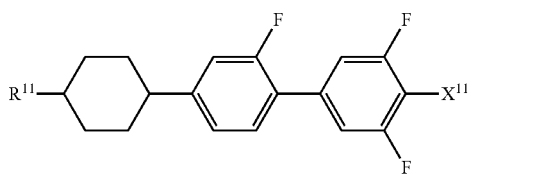
(3-51) 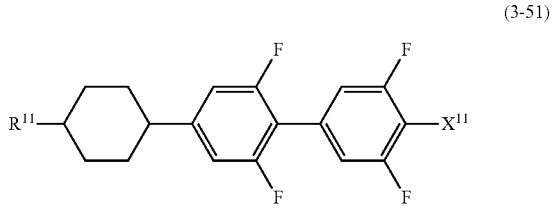
(3-52) 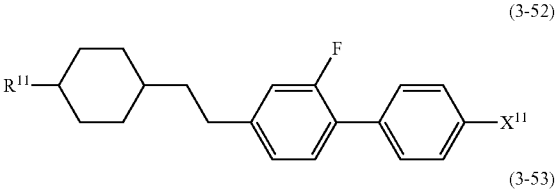
(3-53) 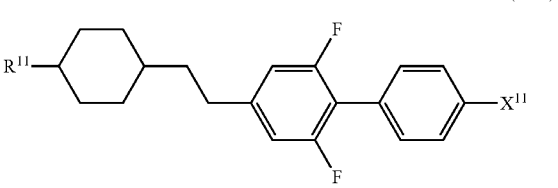
(3-54) 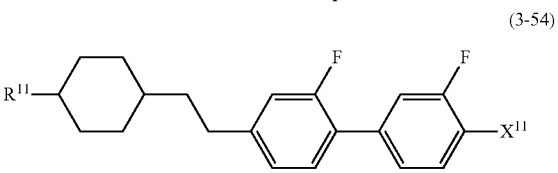

(3-55)
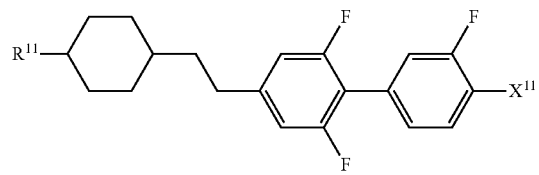
(3-56)
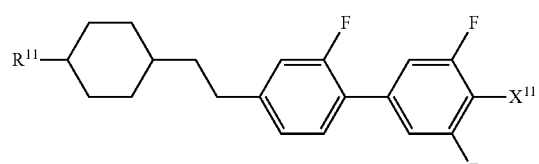
(3-57)
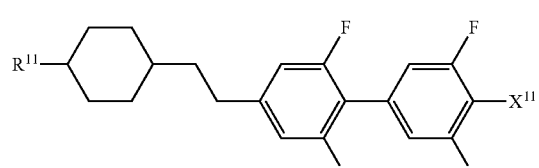
(3-58)
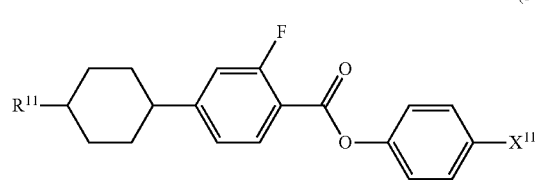
(3-59)
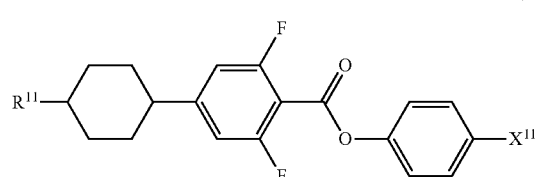
(3-60)
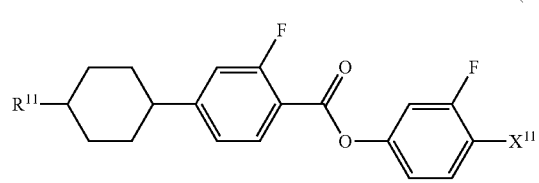
(3-61)
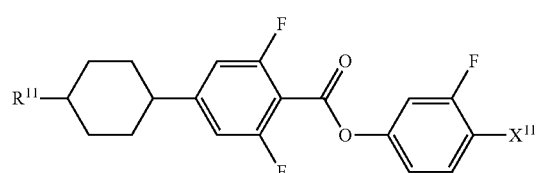
(3-62)
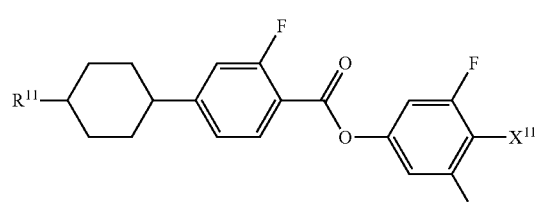
(3-63)
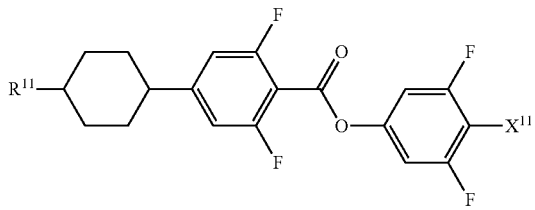
(3-64)
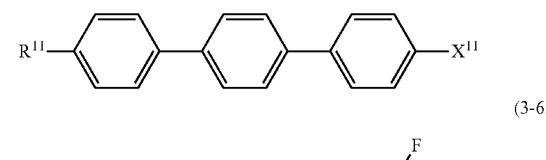
(3-65)
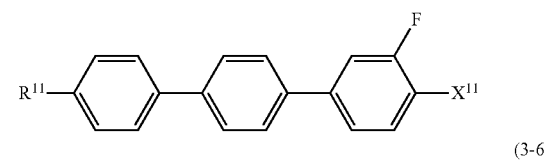
(3-66)
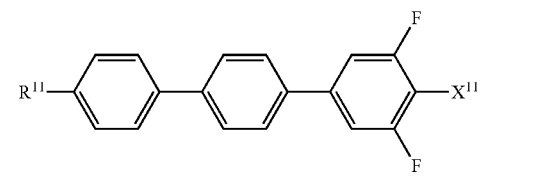
(3-67)
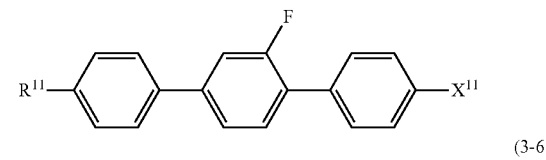
(3-68)
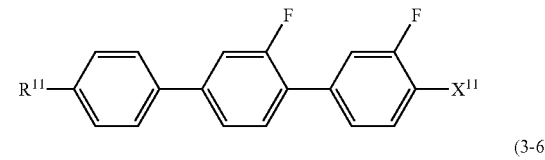
(3-69)
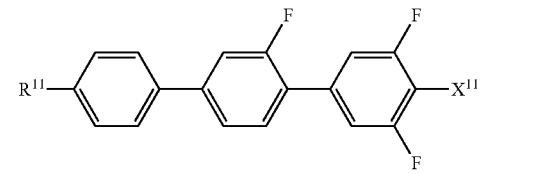
(3-70)
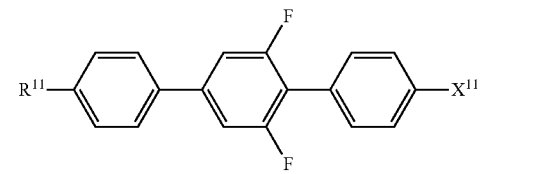
(3-71)

(3-72)
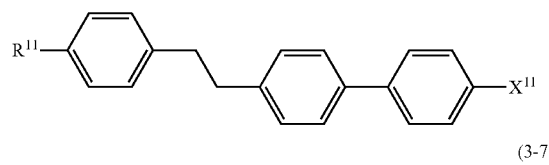
(3-73)
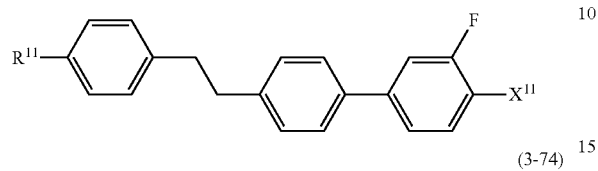
(3-74)
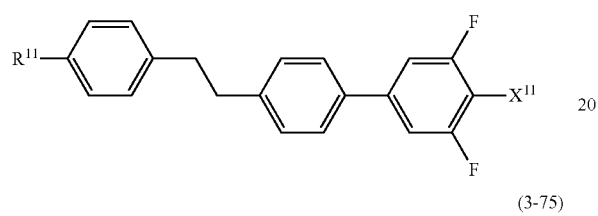
(3-75)
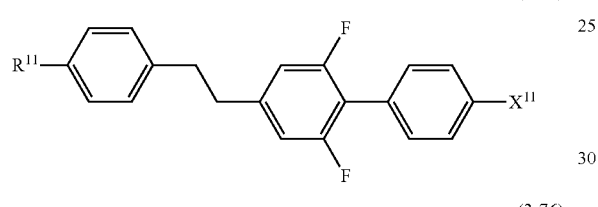
(3-76)
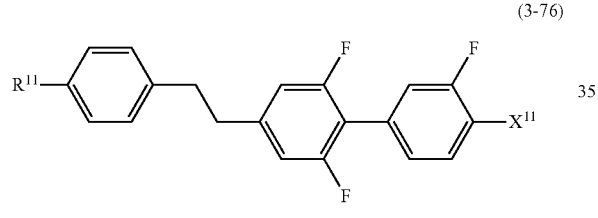
(3-77)
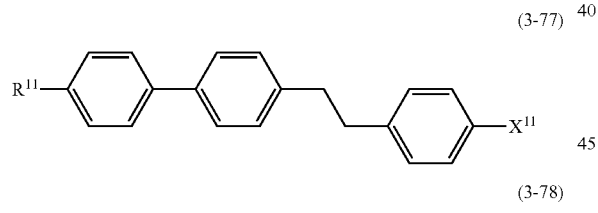
(3-78)
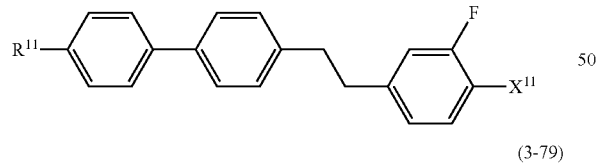
(3-79)
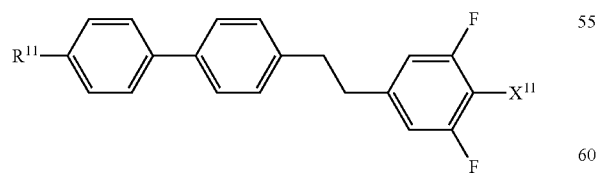
(3-80)
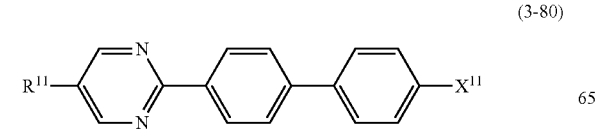
(3-81)
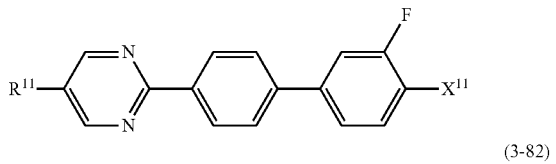
(3-82)
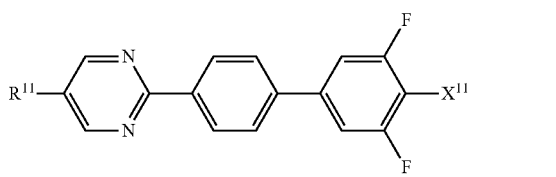
(3-83)
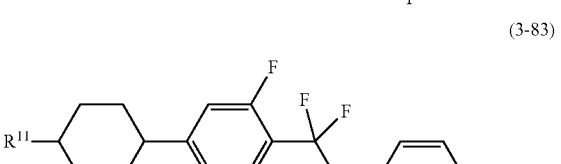
(3-84)
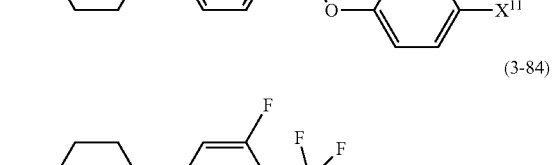
(3-85)
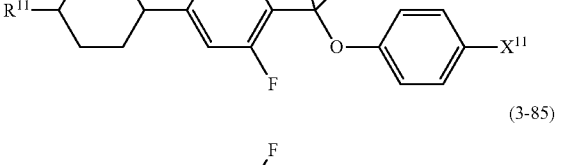
(3-86)
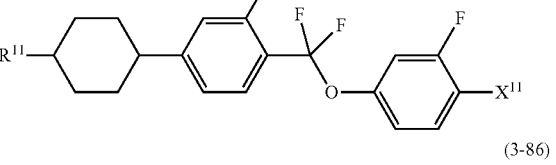
(3-87)
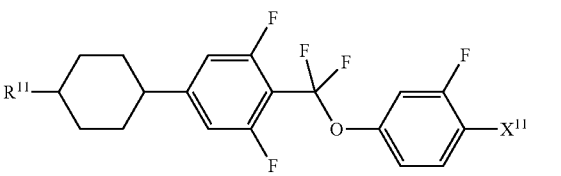
(3-88)
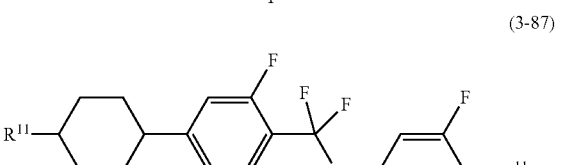

(3-89)
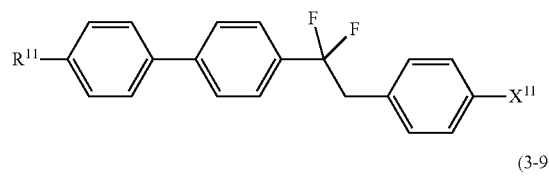
(3-90)
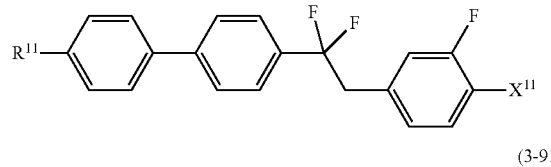
(3-91)
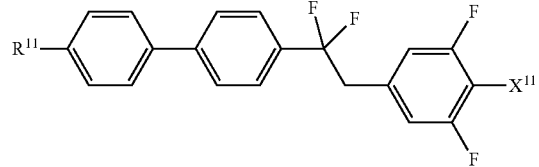
(3-92)
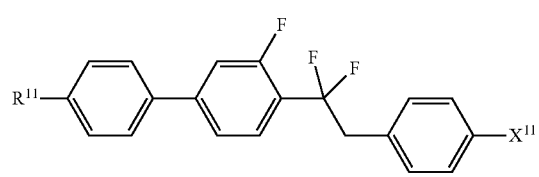
(3-93)
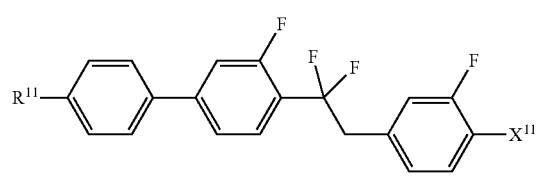
(3-94)
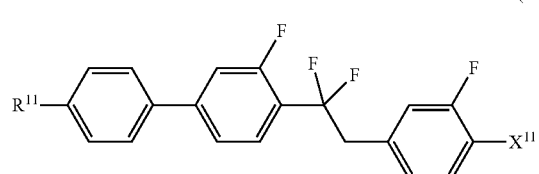
(3-95)
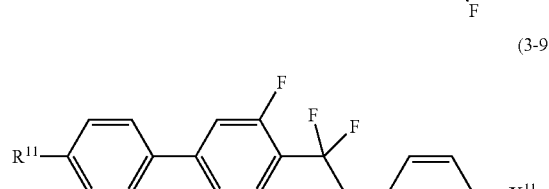
(3-96)
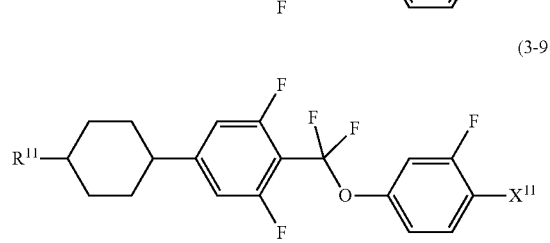
(3-97)
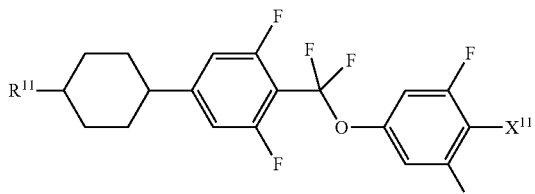
(3-98)
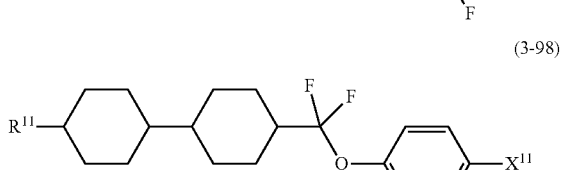
(3-99)
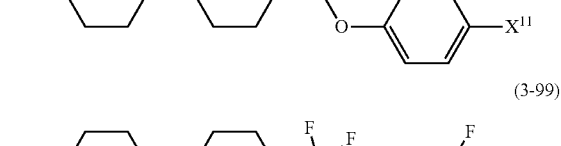
(3-100)
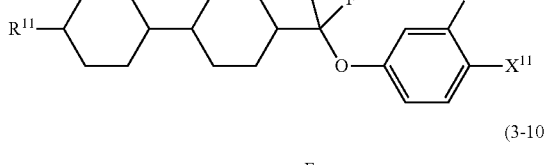
(3-101)
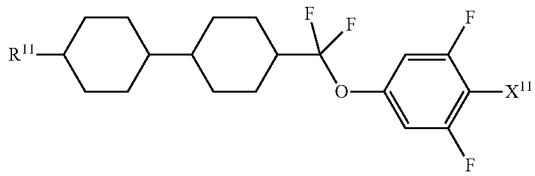
(3-102)
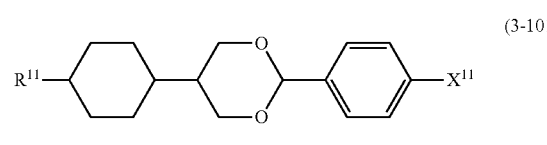
(3-103)
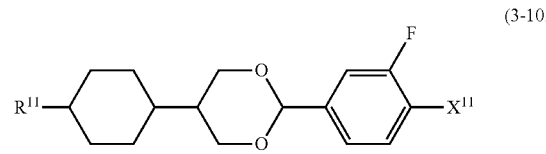
(3-104)
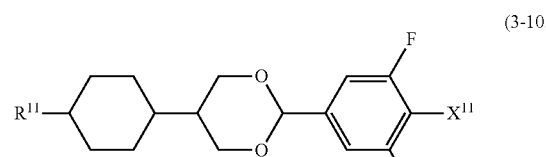
(3-105)
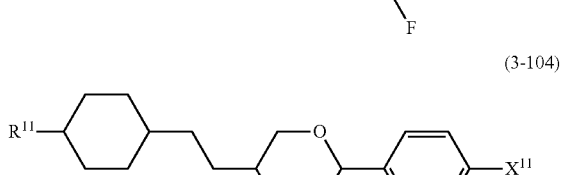

(3-106)
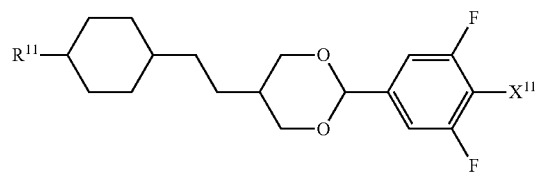
(3-107)
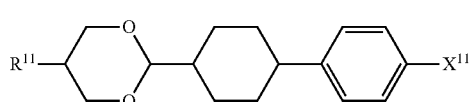
(3-108)
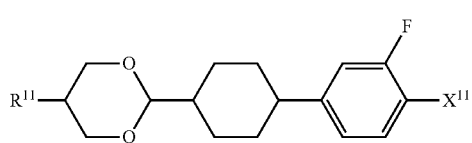
(3-109)
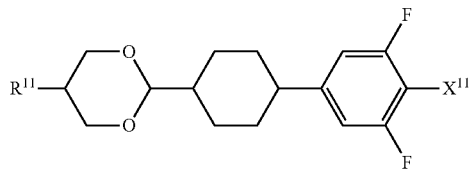
(3-110)
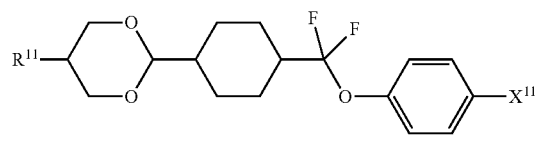
(3-111)
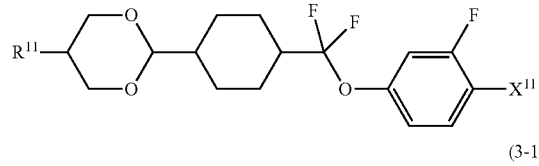
(3-112)
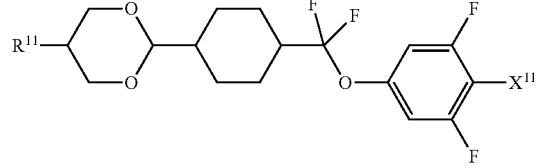
(3-113)
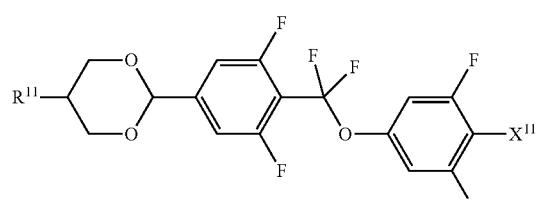
(4-1)
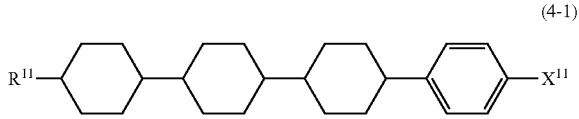
(4-2)
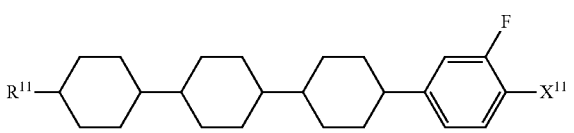
(4-3)
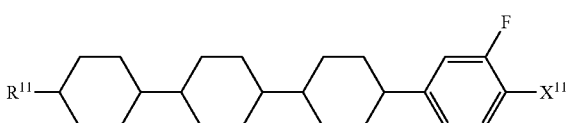
(4-4)
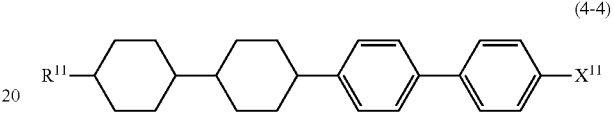
(4-5)
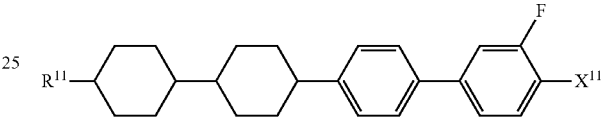
(4-6)
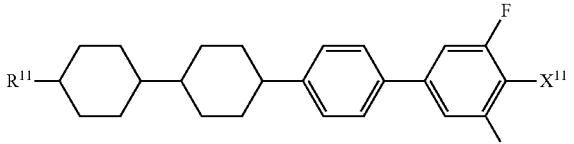
(4-7)
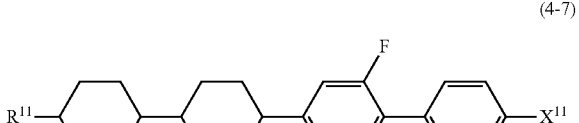
(4-8)
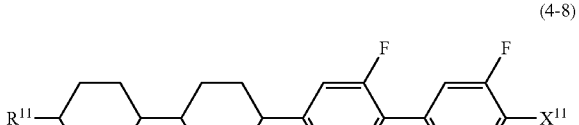
(4-9)
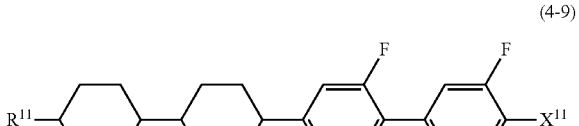
(4-10)
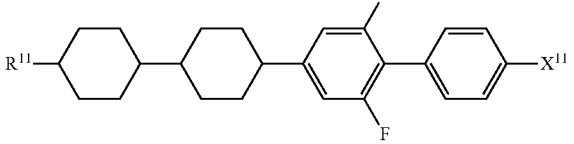

(4-11) through (4-28): chemical structure formulas

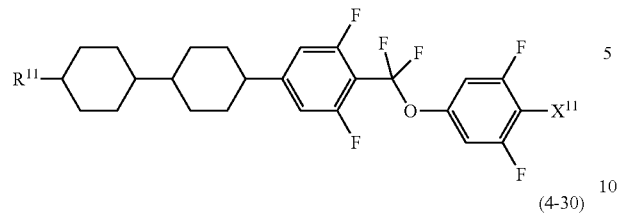
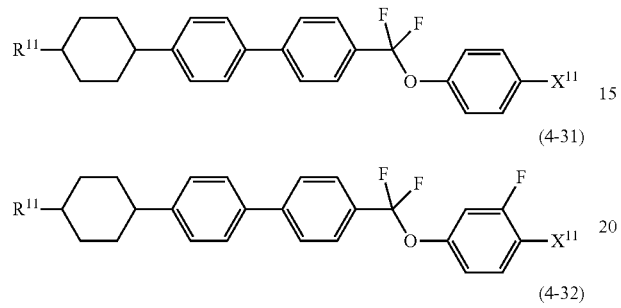
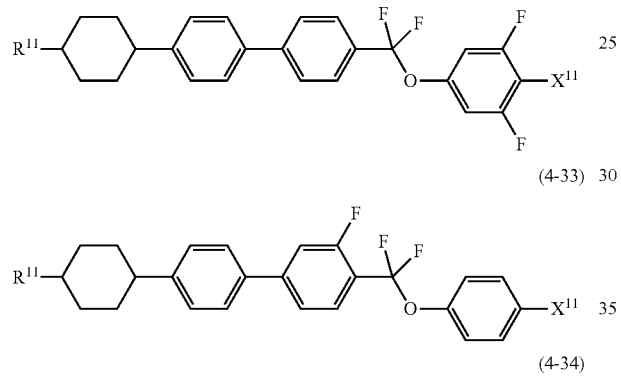
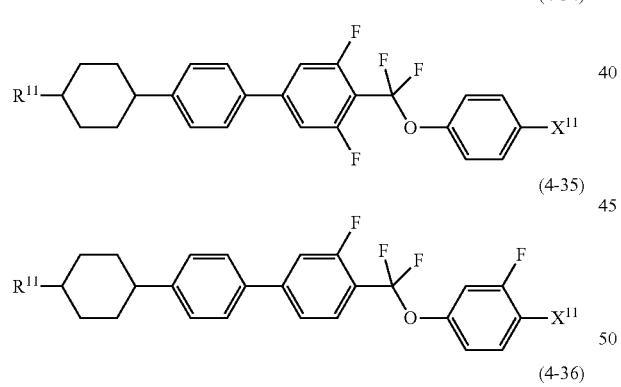

(4-46)
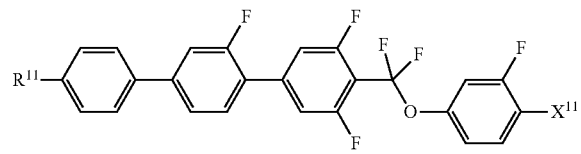

(4-47)
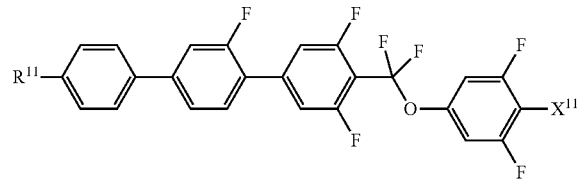

(4-48)

(4-49)
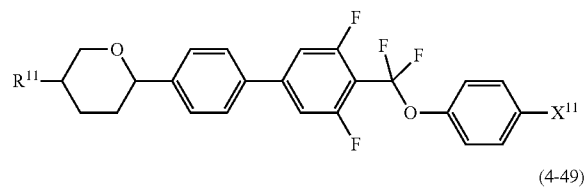

(4-50)
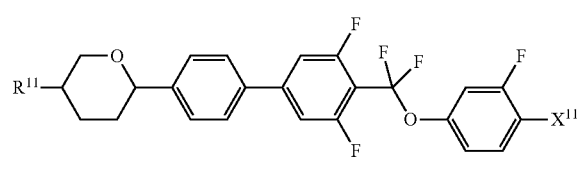

(4-51)
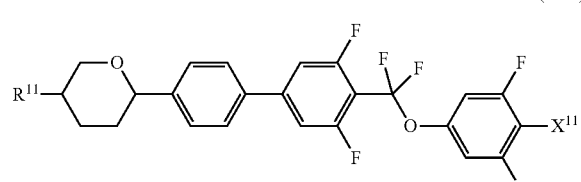

(4-52)
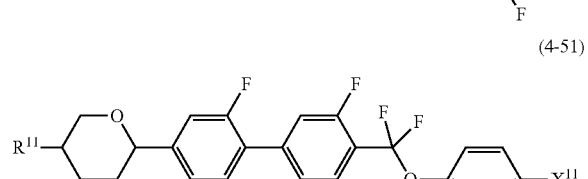

(4-53)
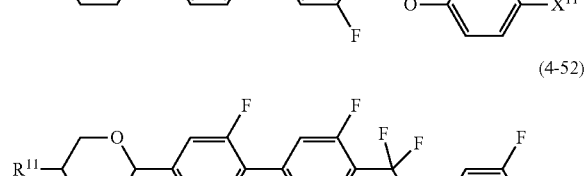

(4-54)
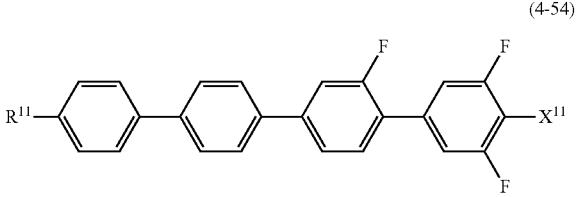

(4-55)
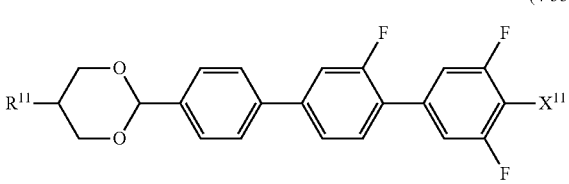

(4-56)
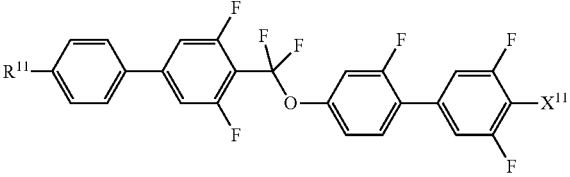

(4-57)
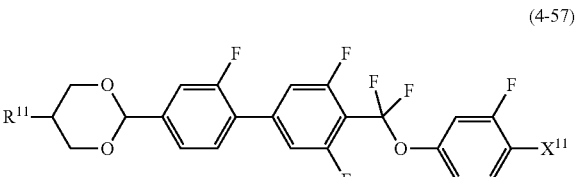

In the compounds (component B), $R^{11}$ and $X^{11}$ are defined in a manner identical with the definitions in the formulas (2) to (4).

Component B has a positive dielectric anisotropy and a superb stability to heat, light and so forth, and therefore is used when a composition for the TFT mode or the PSA mode is prepared. A content of component B is suitably in the range of approximately 1 to approximately 99% by weight, preferably in the range of approximately 10 to approximately 97% by weight, and further preferably in the range of approximately 40 to approximately 95% by weight, based on the total weight of the composition. Viscosity of the composition can be adjusted by further adding compounds (12) to (14) (component E) thereto.

Component C is compound (5) having —C≡N or —C≡C—C≡N at a right terminal group. Preferred examples of component C include compounds (5-1) to (5-64).

(5-1)
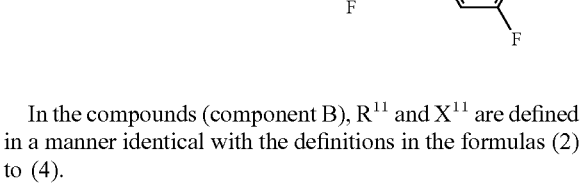

(5-2)

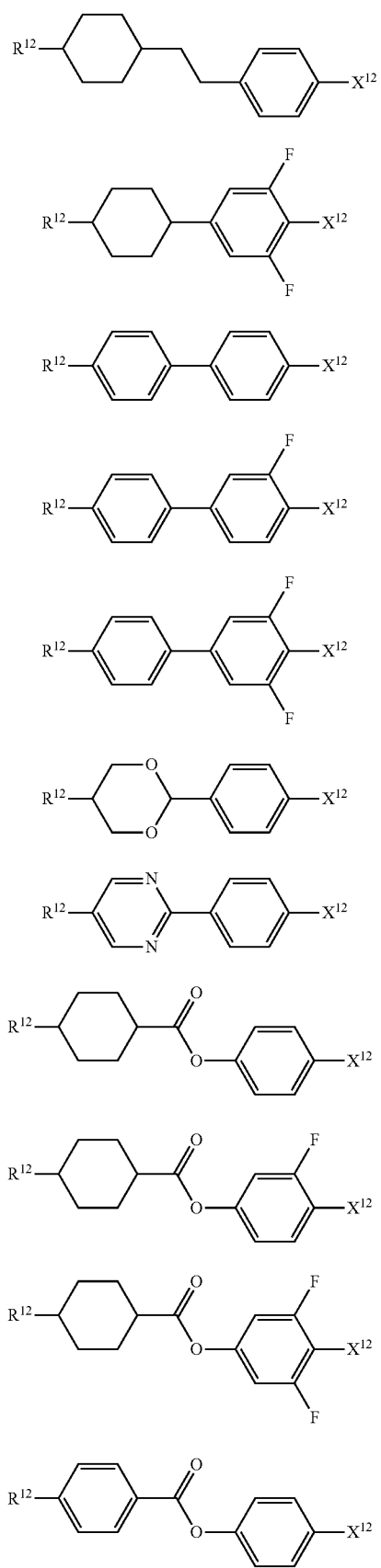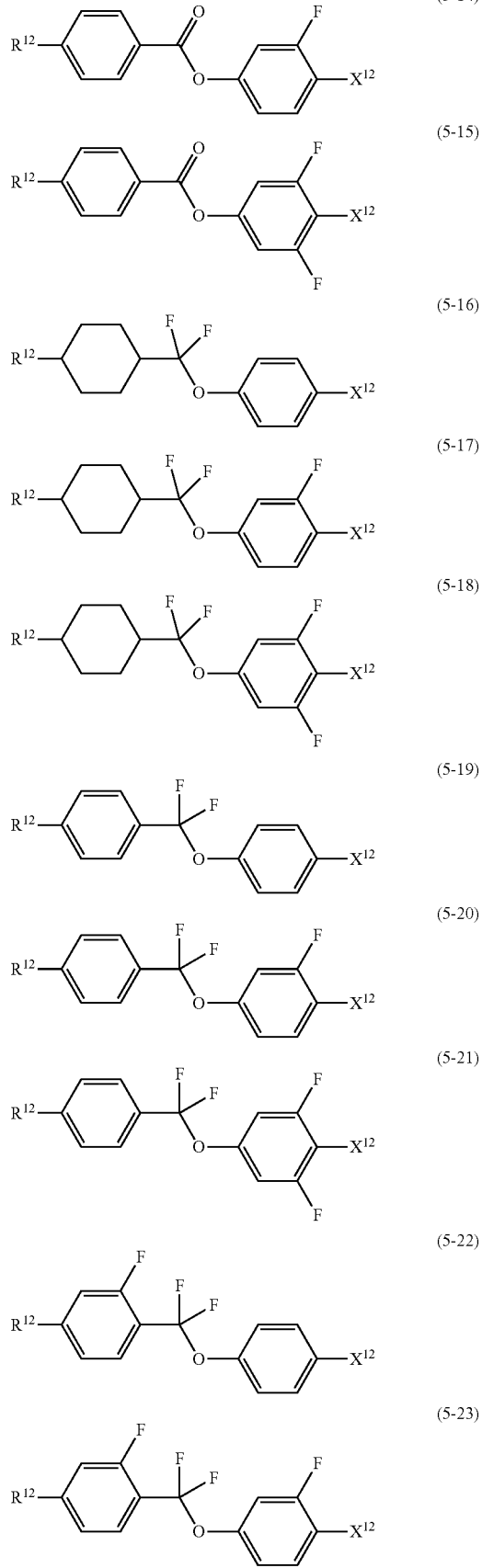

(5-24) 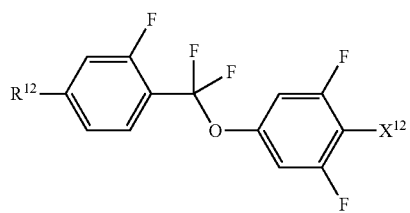
(5-25) 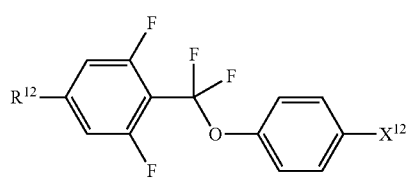
(5-26) 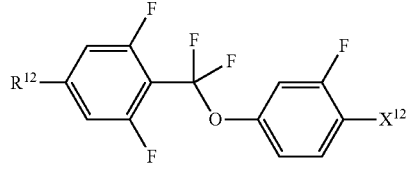
(5-27) 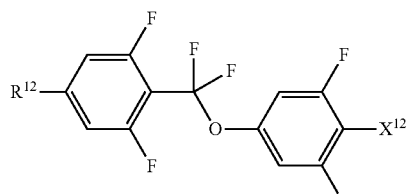
(5-28) 
(5-29)
(5-30) 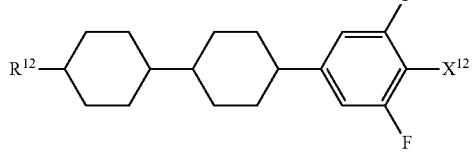
(5-31) 
(5-32) 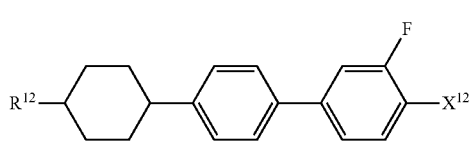
(5-33) 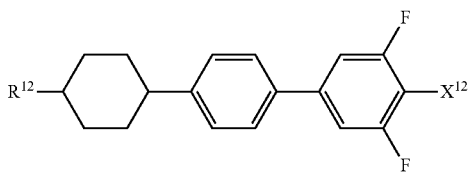
(5-34) 
(5-35) 
(5-36) 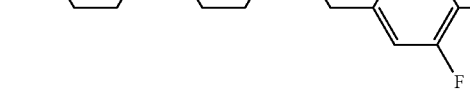
(5-37) 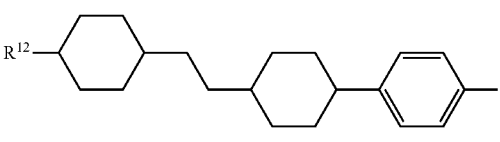
(5-38) 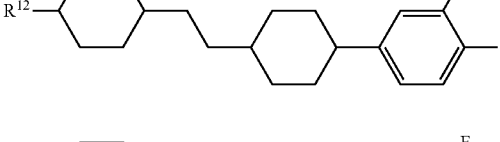
(5-39) 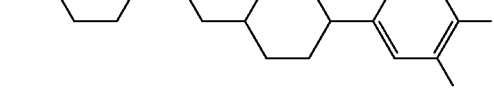
(5-40) 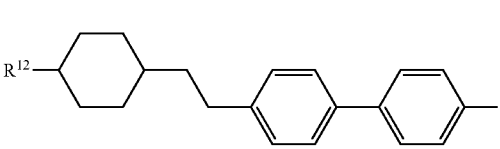
(5-41)
(5-42)

(5-43) 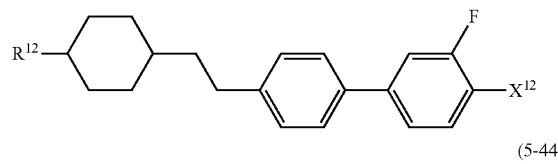
(5-44) 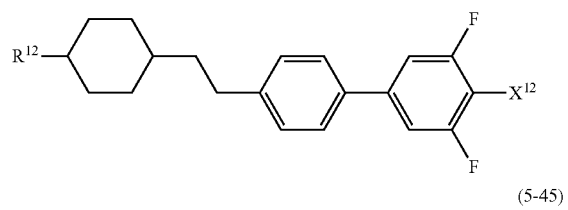
(5-45) 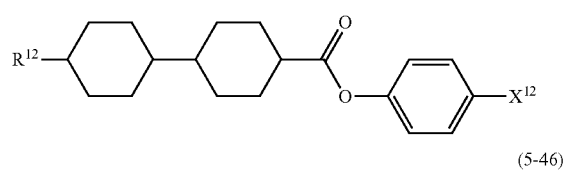
(5-46) 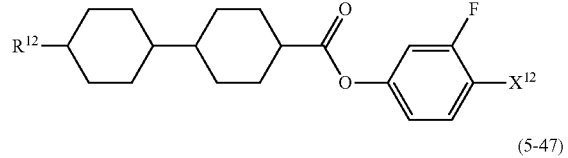
(5-47) 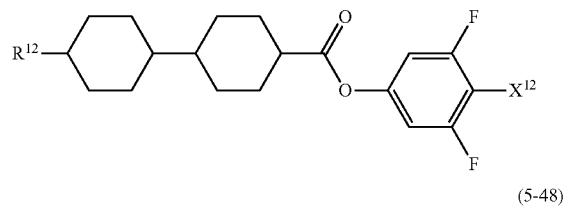
(5-48) 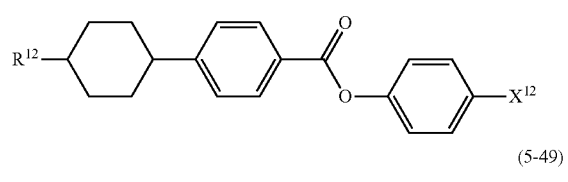
(5-49) 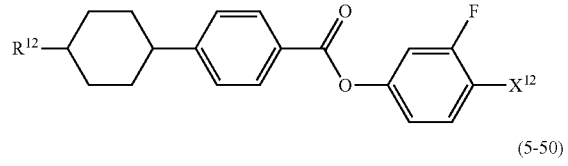
(5-50) 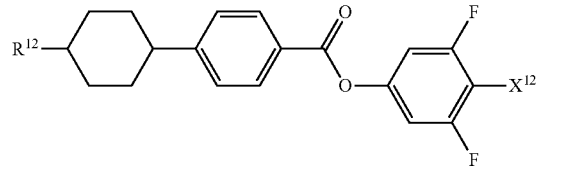
(5-51) 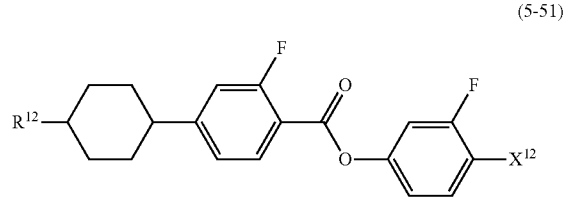
(5-52) 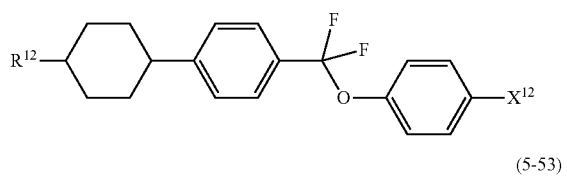
(5-53) 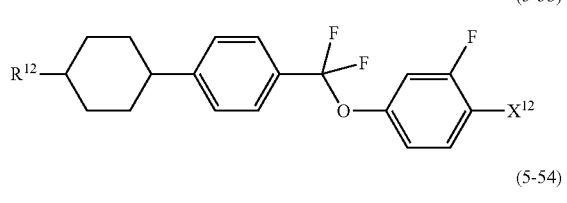
(5-54) 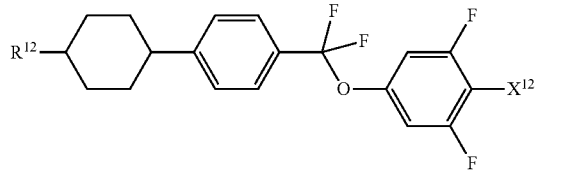
(5-55) 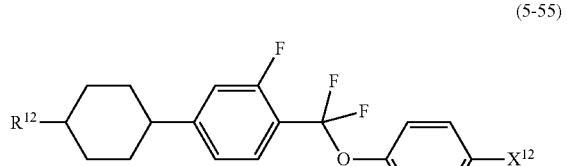
(5-56) 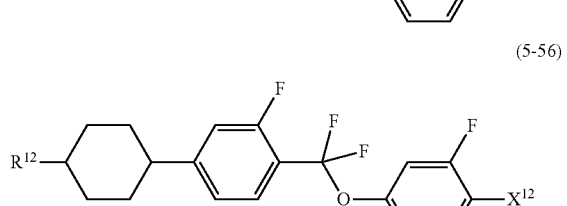
(5-57) 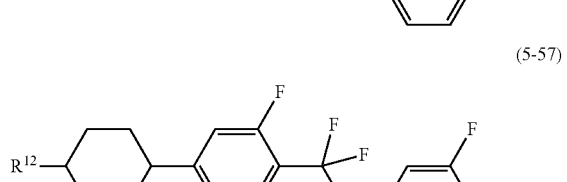
(5-58) 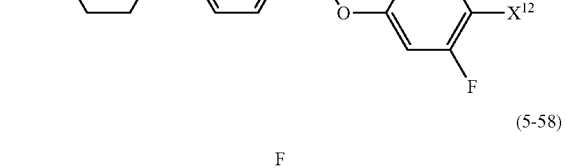
(5-59) 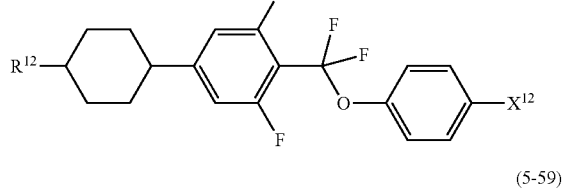
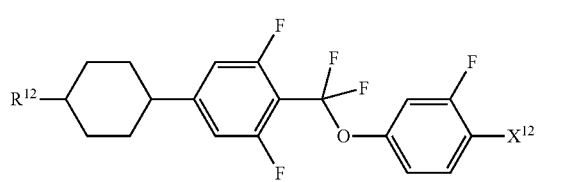

(5-60)

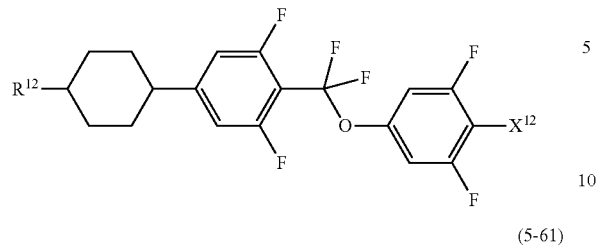

(5-61)

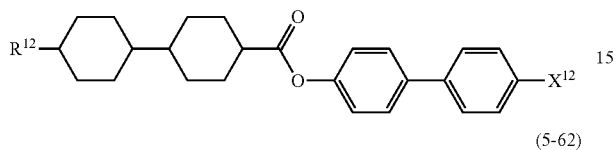

(5-62)

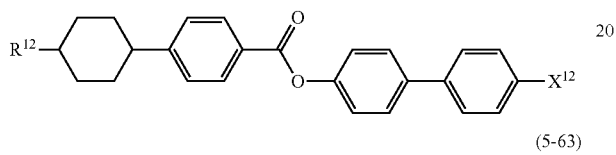

(5-63)

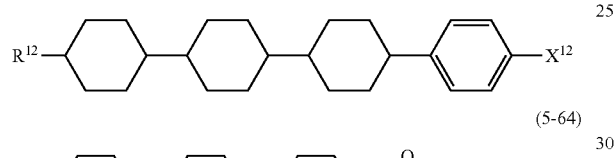

(5-64)

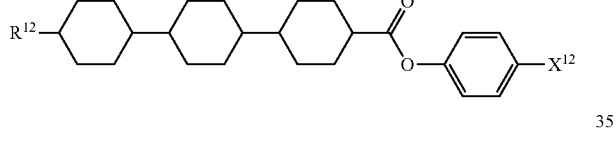

In the compounds (component C), $R^{12}$ and $X^{12}$ are defined in a manner identical with the definitions in the formula (5).

Component C has a positive dielectric anisotropy, and a large value thereof, and therefore is mainly used when a composition for the STN mode, the TN mode or the PSA mode is prepared. The dielectric anisotropy of the composition can be increased by adding the component C thereto. Component C is effective in extending the temperature range of the liquid crystal phase, adjusting the viscosity or adjusting the optical anisotropy. Component C is useful also for adjustment of a voltage-transmittance curve of the device.

When a composition for the STN mode or the TN mode is prepared, a content of component C is preferably in the range of approximately 1 to approximately 99% by weight, preferably in the range of approximately 10 to approximately 97% by weight, and further preferably in the range of approximately 40 to approximately 95% by weight, based on the total weight of the composition. The temperature range of the liquid crystal phase, the viscosity, the optical anisotropy, the dielectric anisotropy or the like of the composition can be adjusted by adding component E thereto.

Component D includes compounds (6) to (12). The compounds have a benzene ring in which hydrogen in lateral positions are replaced by two halogen atoms, such as 2,3-difluoro-1,4-phenylene. Preferred examples of component D include compounds (6-1) to (6-8), compounds (7-1) to (7-17), compound (8-1), compounds (9-1) to (9-3), compounds (10-1) to (10-12), compounds (11-1) to (11-3) and compounds (12-1) to (12-3).

(6-1)

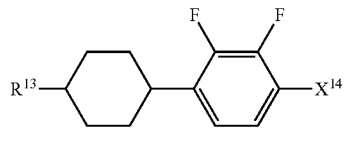

(6-2)

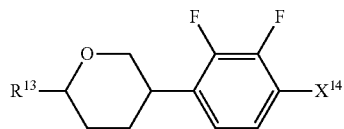

(6-3)

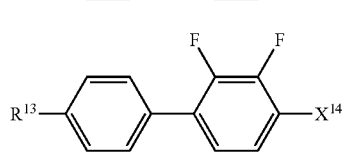

(6-4)

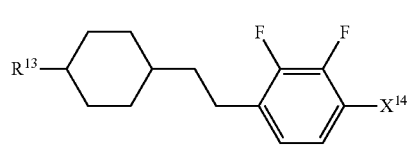

(6-5)

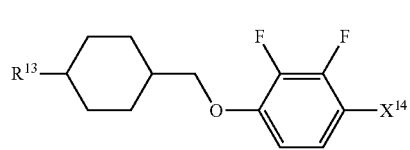

(6-6)

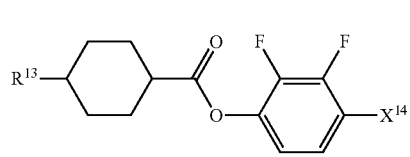

(6-7)

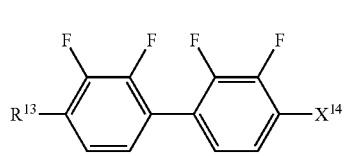

(6-8)

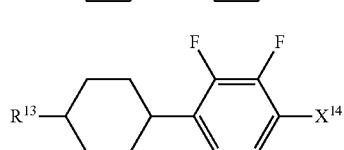

(7-1)

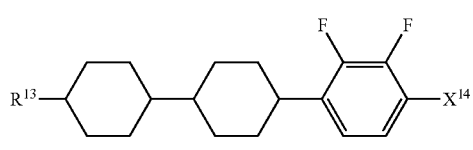

(7-2)

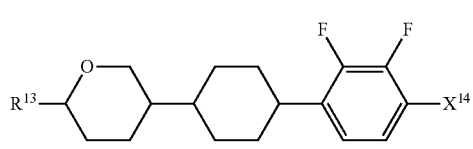

(7-3)

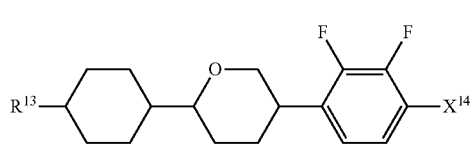

(7-4) 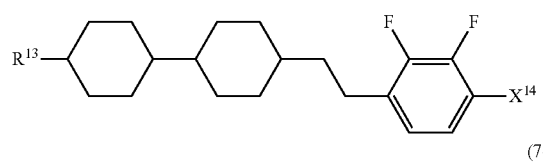
(7-5) 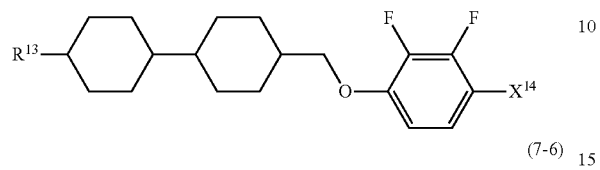
(7-6) 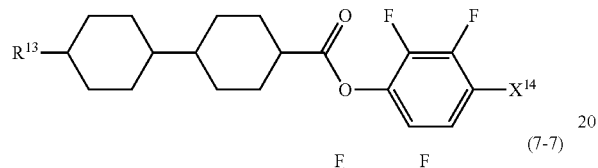
(7-7) 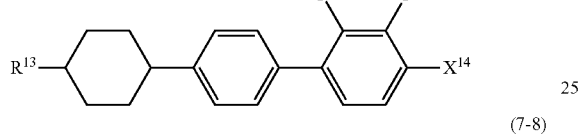
(7-8) 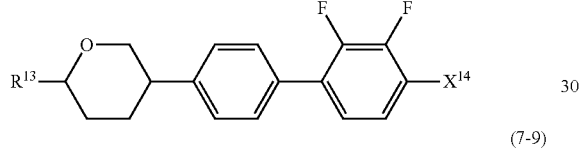
(7-9) 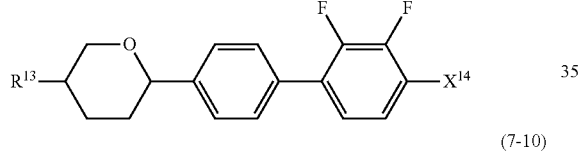
(7-10) 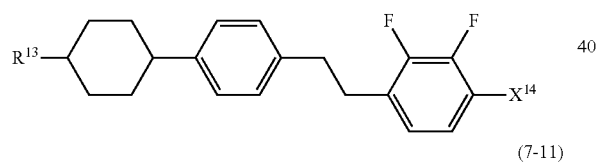
(7-11) 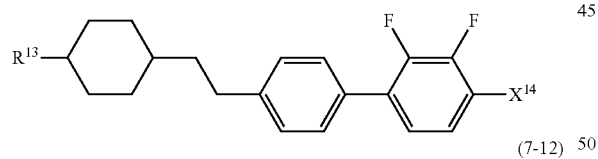
(7-12) 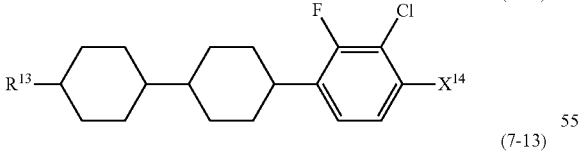
(7-13) 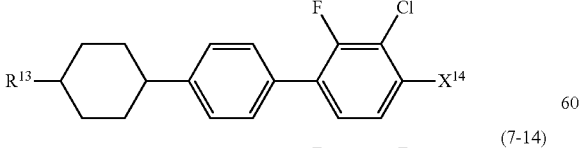
(7-14) 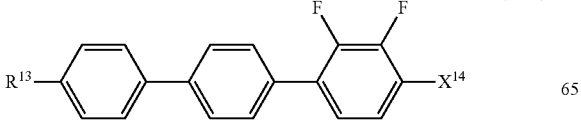
(7-15) 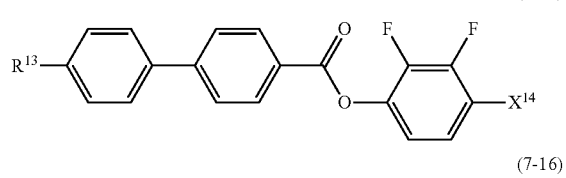
(7-16) 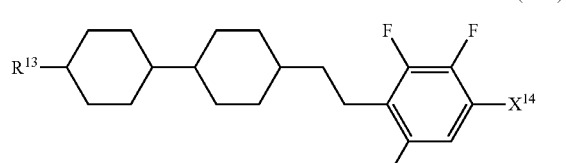
(7-17) 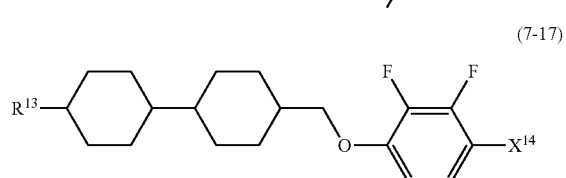
(8-1) 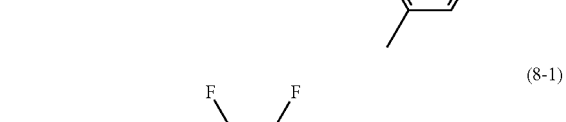
(9-1) 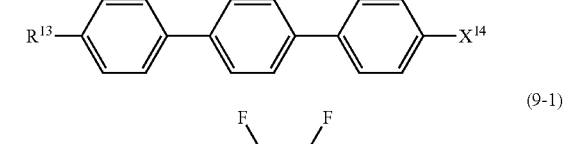
(9-2) 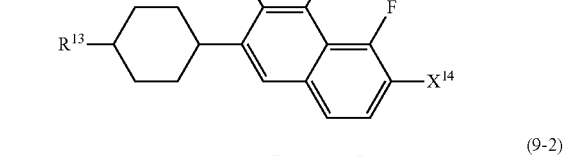
(9-3) 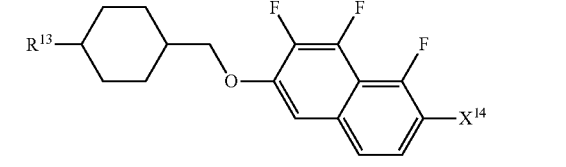
(10-1) 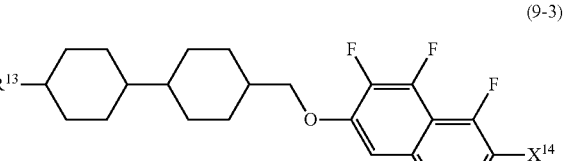
(10-2) 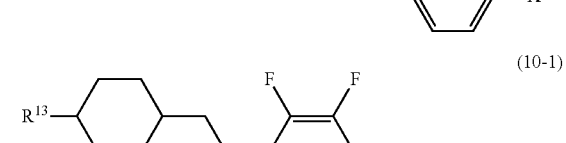

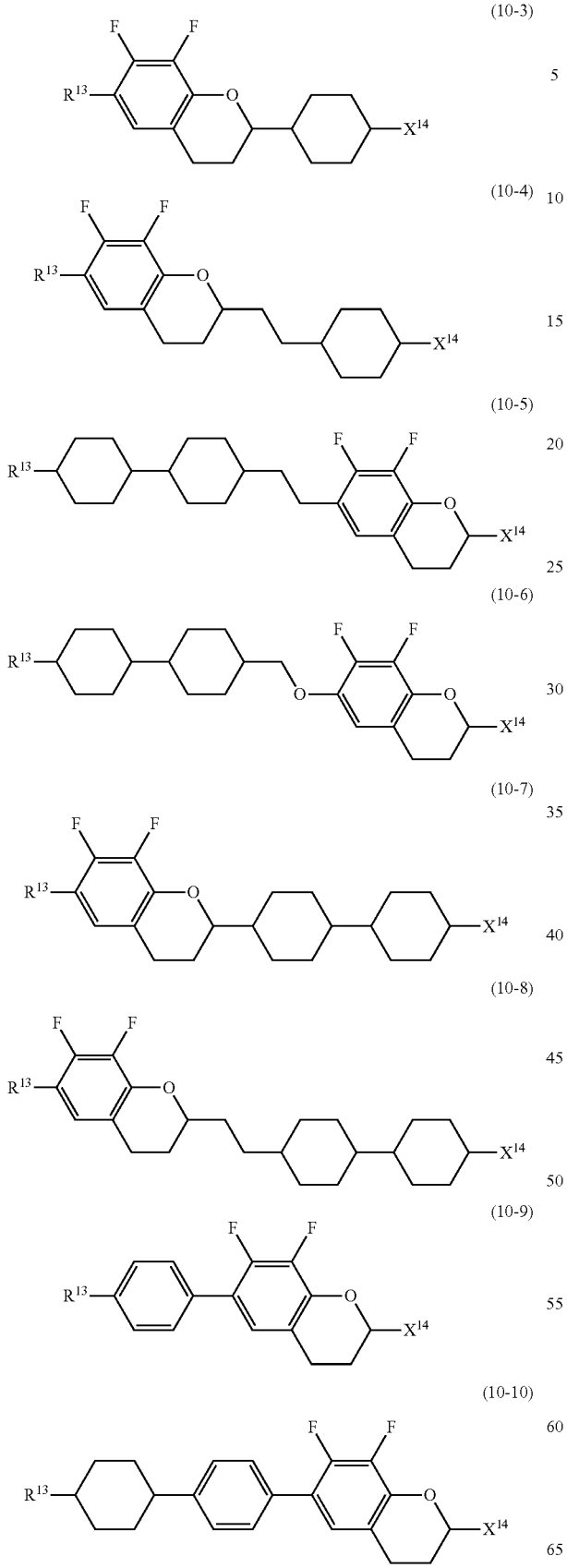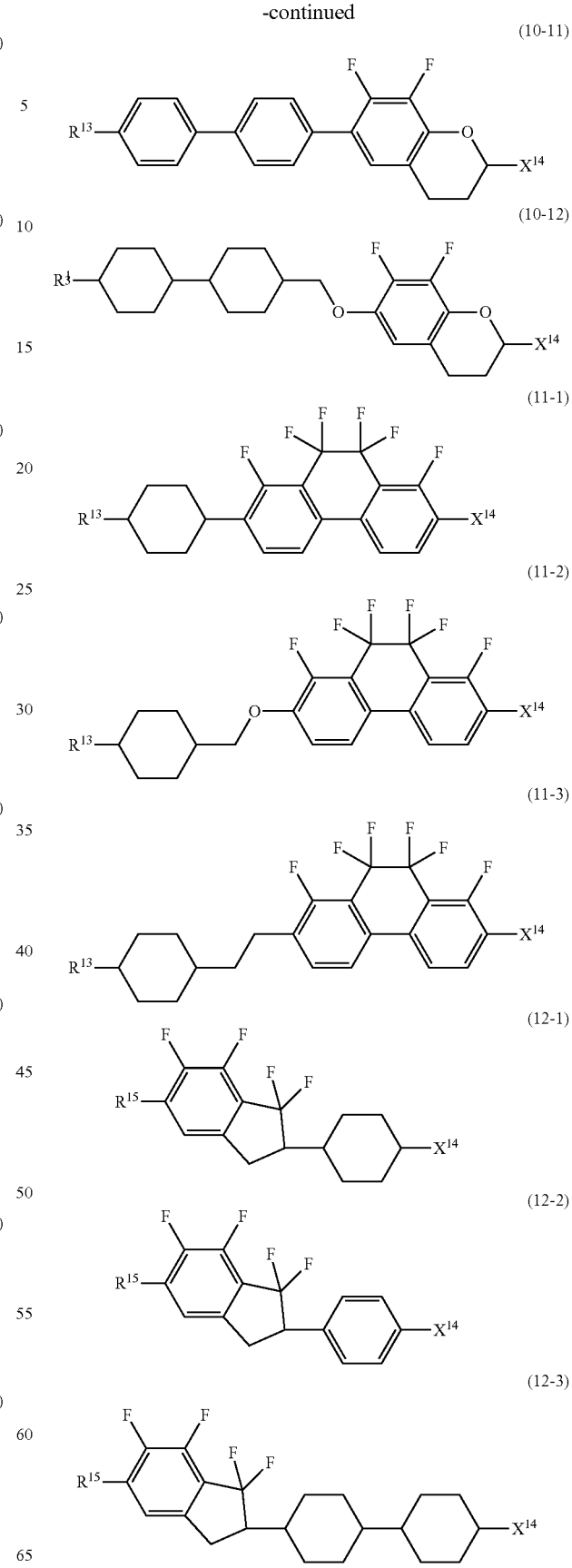

In the compounds (component D), $R^{13}$, $R^{14}$ and $R^{15}$ are defined in a manner identical with the definitions in the formulas (6) to (12).

Component D is a compound having the negative dielectric anisotropy. Component D is mainly used when a composition for the VA mode or the PSA mode is prepared. Among types of component D, compound (6) is a bicyclic compound, and therefore is effective mainly in adjusting the viscosity, the optical anisotropy or the dielectric anisotropy. Compounds (7) and (8) are a tricyclic compound, and therefore effective in increasing the maximum temperature, the optical anisotropy or the dielectric anisotropy. Compounds (9) to (12) are effective in increasing the dielectric anisotropy.

When a composition for the VA mode or the PSA mode is prepared, a content of component D is preferably approximately 40% by weight or more, and further preferably in the range of approximately 50 to approximately 95% by weight, based on the total weight of the composition. When component D is added to a composition having a positive dielectric anisotropy, the content of component D is preferably approximately 30% or less based on the total weight of the composition. When component D is added, the elastic constant of the composition and the voltage-transmittance curve of the device can be adjusted.

Component E is a compound in which two terminal groups are alkyl or the like. Preferred examples of component E include compounds (13-1) to (13-11), compounds (14-1) to (14-19) and compounds (15-1) to (15-7).

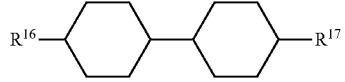

(13-1)

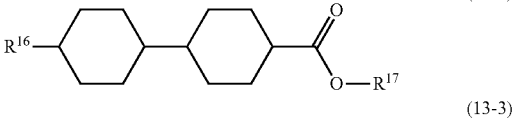

(13-2)

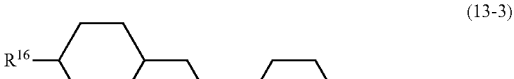

(13-3)

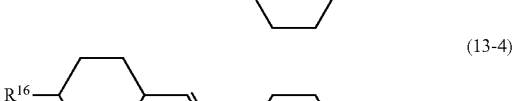

(13-4)

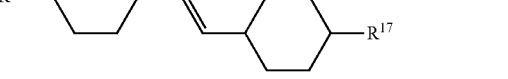

(13-5)

(13-6)

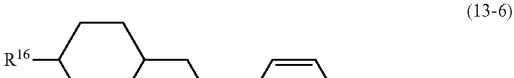

(13-7)

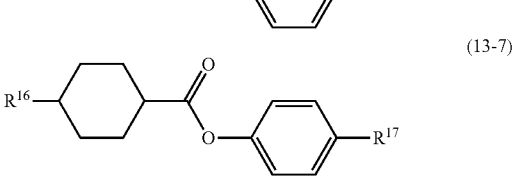

-continued

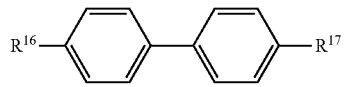

(13-8)

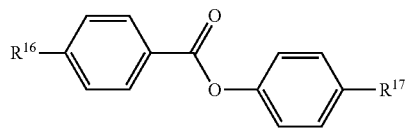

(13-9)

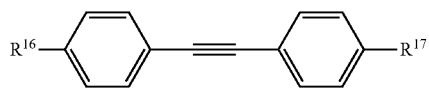

(13-10)

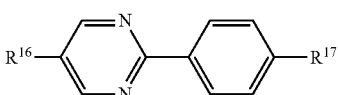

(13-11)

(14-1)

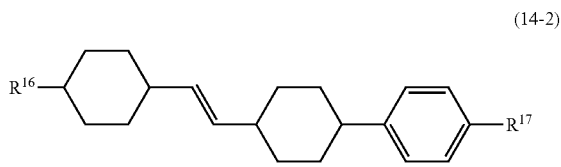

(14-2)

(14-3)

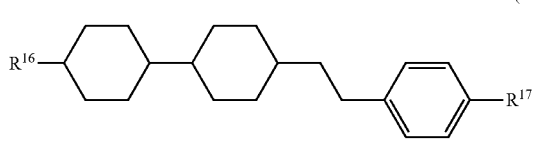

(14-4)

(14-5)

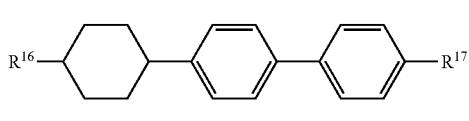

(14-6)

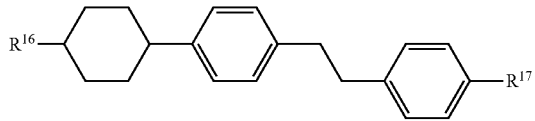

(14-7)

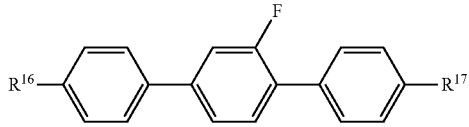

(14-8)

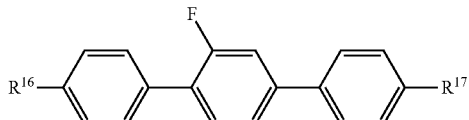

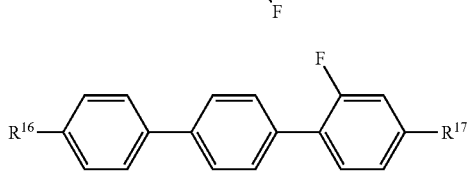

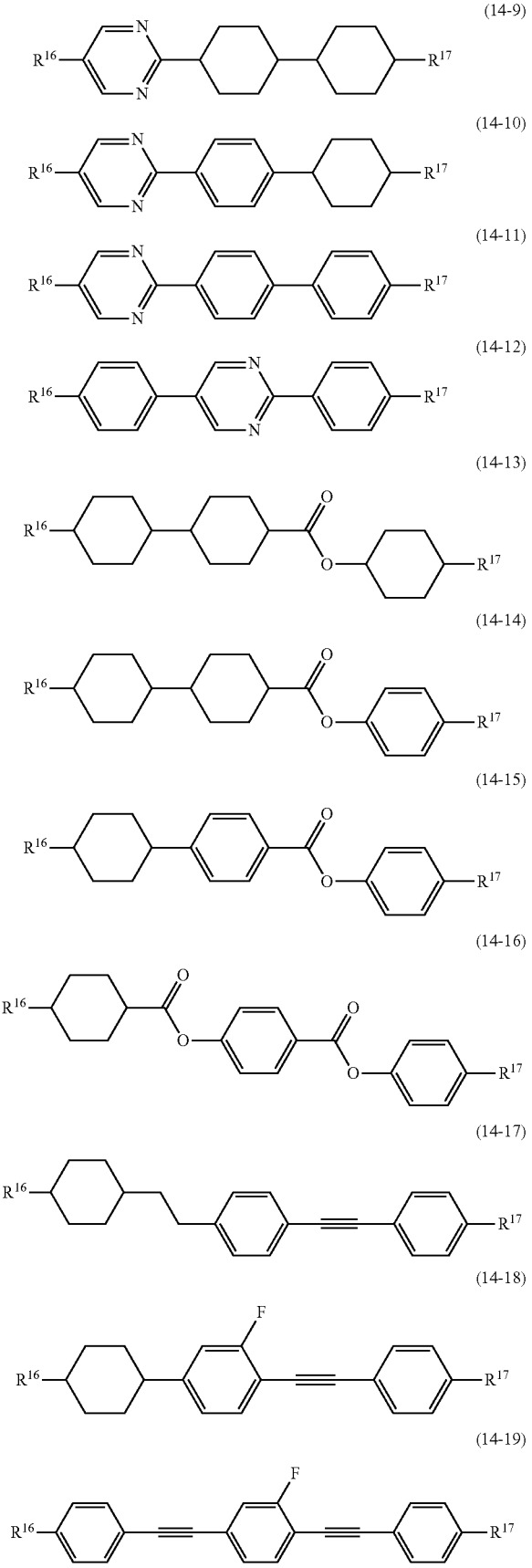
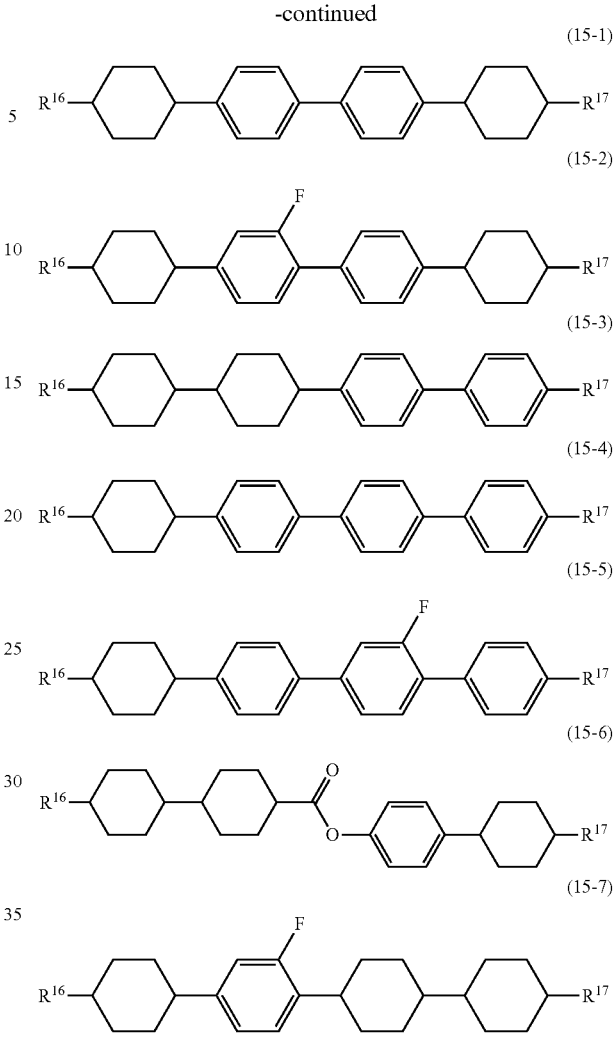

In the compounds (component E), $R^{16}$ and $R^{17}$ are defined in a manner identical with the definitions in the formulas (13) to (15).

Component E has a small absolute value of dielectric anisotropy, and therefore is a compound close to neutrality. Compound (13) is effective mainly in adjusting the viscosity or the optical anisotropy. Compound (14) and (15) are effective in extending the temperature range of the nematic phase by increasing the maximum temperature, or in adjusting the optical anisotropy.

When a content of component E is increased, the viscosity of the composition decreases, but the dielectric anisotropy also decreases. Thus, as long as a desired value of threshold voltage of the device is met, the content is preferably as large as possible. Therefore, when a composition for the VA mode or the PSA mode is prepared, the content of component E is preferably approximately 30% by weight or more, and further preferably approximately 40% by weight or more, based on the total weight of the composition.

Composition (1) is prepared by a method of dissolving necessary components at a high temperature, or the like. According to an application, an additive may be added to the composition. Specific examples of the additive include an optically active compound, a polymerizable compound, a polymerization initiator, an antioxidant, an ultraviolet light absorber, a light stabilizer, a heat stabilizer and a defoaming agent. Such additives are well known to those skilled in the art, and are described in literature.

Composition (1) may further contain at least one optically active compound. A publicly known chiral dopant can be added as the optically active compound. The chiral dopant is effective in inducing a helical structure in liquid crystal molecules to give a necessary twist angle, thereby preventing a reverse twist. Preferred examples of the chiral dopant include compounds (Op-1) to (Op-18) below. In compound (Op-18), ring J is 1,4-cyclohexylene or 1,4-phenylene, and $R^{24}$ is alkyl having 1 to 10 carbons.

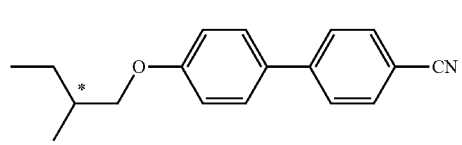

(Op-1)

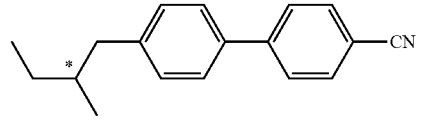

(Op-2)

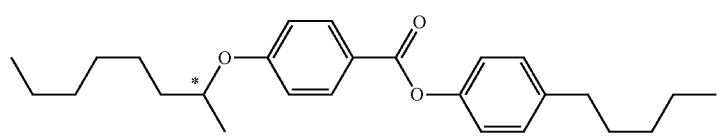

(Op-3)

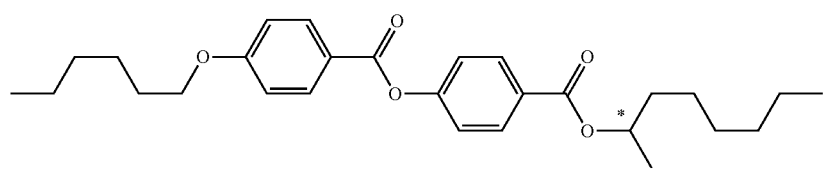

(Op-4)

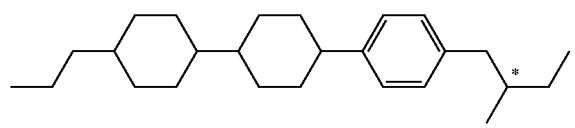

(Op-5)

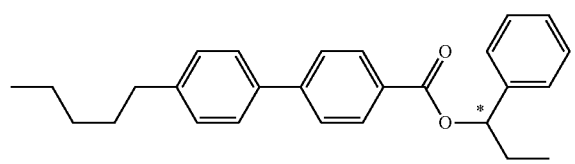

(Op-6)

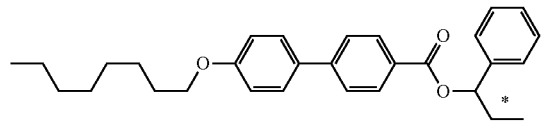

(Op-7)

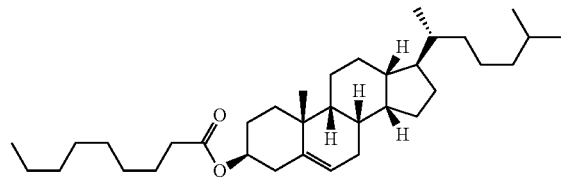

(Op-8)

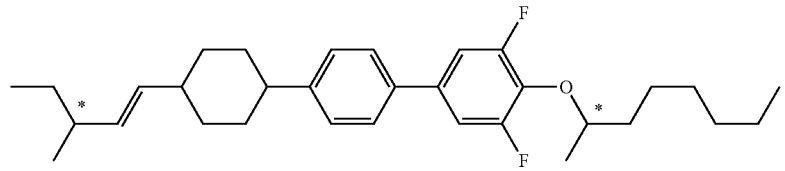

(Op-9)

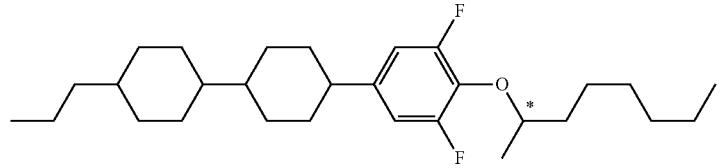

(Op-10)

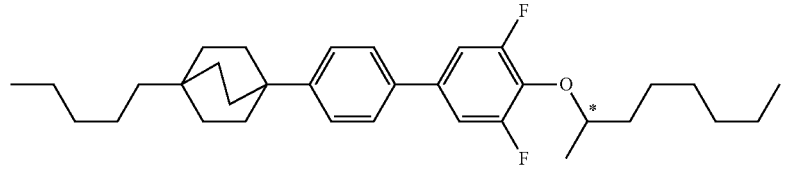

(Op-11)

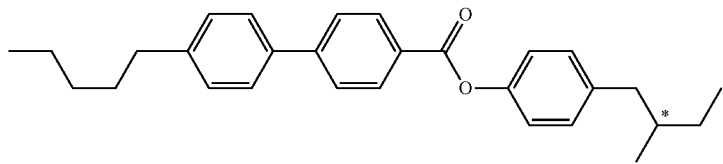
(Op-12)

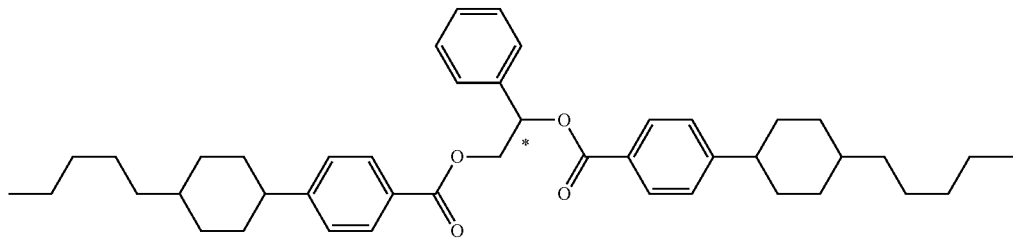
(Op-13)

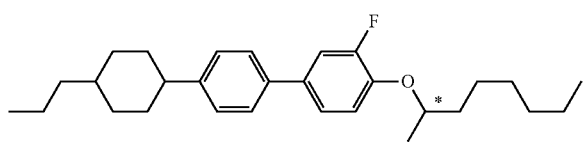
(Op-14)

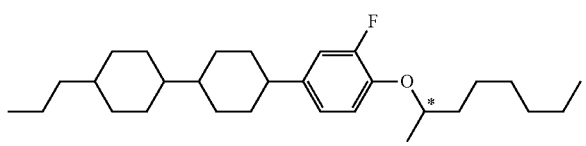
(Op-15)

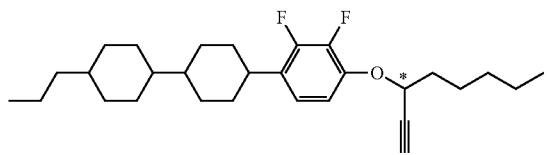
(Op-16)

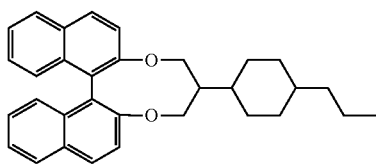
(Op-17)

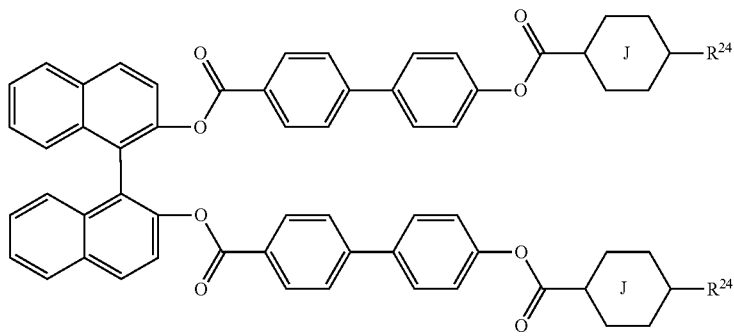
(Op-18)

In composition (1), a helical pitch is adjusted by addition of such an optically active compound. The helical pitch is preferably adjusted to the range of approximately 40 to approximately 200 micrometers in a composition for the TFT mode and the TN mode. The helical pitch is preferably adjusted to the range of approximately 6 to approximately 20 micrometers in a composition for the STN mode. In the case of a composition for a BTN mode, the helical pitch is preferably adjusted to the range of approximately 1.5 to approximately 4 micrometers. Two or more optically active compounds may be added for the purpose of adjusting temperature dependence of the helical pitch.

Composition (1) can also be used for the PSA mode by adding the polymerizable compound. Specific examples of the polymerizable compound include acrylate, methacrylate, a vinyl compound, a vinyloxy compound, propenyl ether, an epoxy compound (oxirane, oxetane) and vinyl ketone. Preferred examples include compounds (M-1) to (M-12) below. The polymerizable compound is polymerized by irradiation with ultraviolet light or the like. The compound may be polymerized in the presence of a suitable initiator such as a photopolymerization initiator. Suitable conditions for polymerization, suitable types of the initiator and suitable amounts thereof are known to those skilled in the art and are described in literature.

In compounds (M-1) to (M-12), $R^{20}$ is hydrogen or methyl; s is 0 or 1; and t and u are independently an integer from 1 to 10. A parenthesized symbol F stands for hydrogen or fluorine.

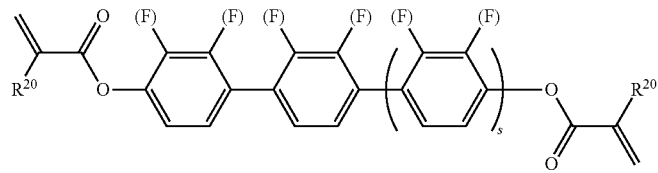
(M1)
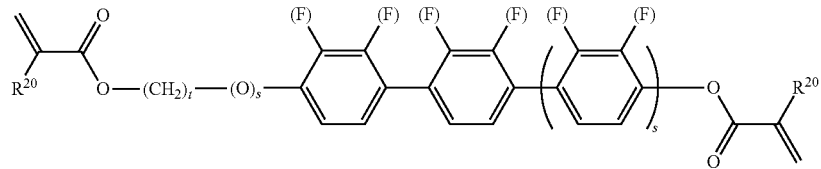
(M-2)
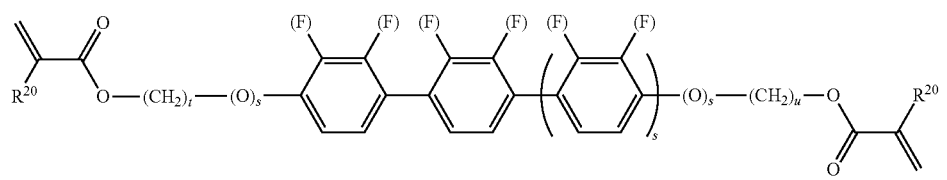
(M-3)
M-4
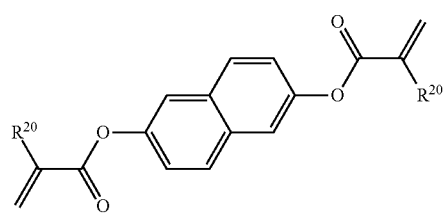
M-5
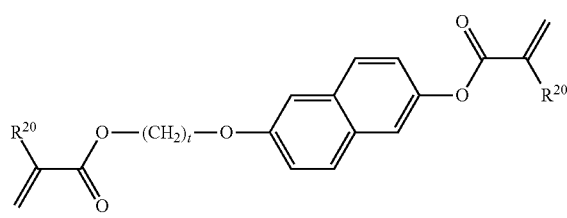
M-6
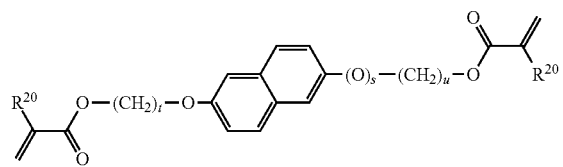
M-7
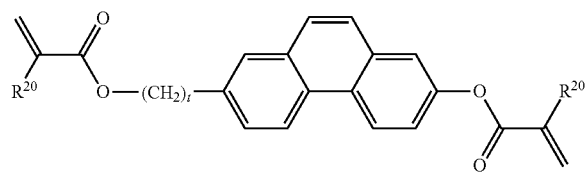
M-8
M-9
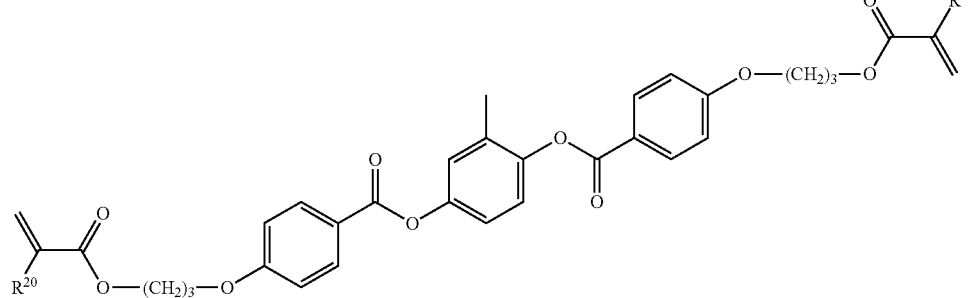

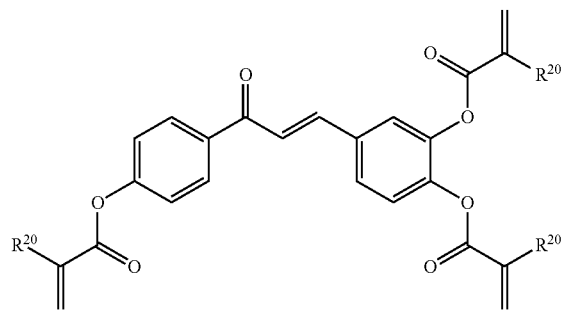

M-10

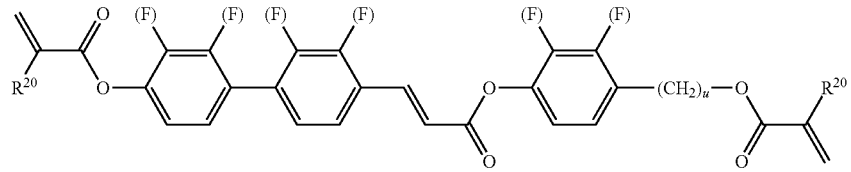

M-11

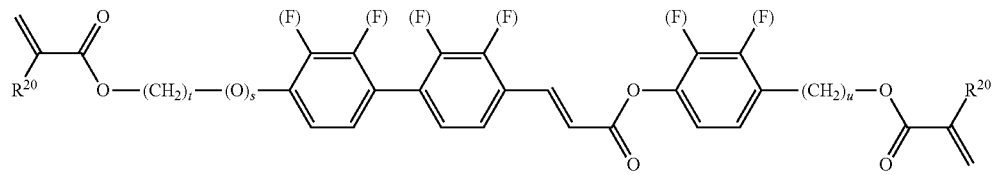

M-12

The antioxidant is effective for maintaining a large voltage holding ratio. Preferred examples of the antioxidant include compounds (AO-1) and (AO-2) below; IRGANOX 415, IRGANOX 565, IRGANOX 1010, IRGANOX 1035, IRGANOX 3114 and IRGANOX 1098 (trade names: BASF). The ultraviolet light absorber is effective for preventing a decrease of the maximum temperature. Preferred examples of the ultraviolet light absorber include a benzophenone derivative, a benzoate derivative and a triazole derivative. Specific examples include compounds (AO-3) and (AO-4) below; TINUVIN 329, TINUVIN P, TINUVIN 326, TINUVIN 234, TINUVIN 213, TINUVIN 400, TINUVIN 328 and TINUVIN 99-2 (trade names: BASF); and 1,4-diazabicyclo[2.2.2]octane (DABCO).

A light stabilizer such as amine having steric hindrance is preferred for maintaining the large voltage holding ratio. Preferred examples of the light stabilizer include compounds (AO-5) and (AO-6) below; TINUVIN 144, TINUVIN 765 and TINUVIN 770DF (trade names: BASF). The heat stabilizer is also effective for maintaining the large voltage holding ratio, and preferred examples include IRGAFOS 168 (trade name: BASF). The defoaming agent is effective for preventing foam formation. Preferred examples of the defoaming agent include dimethyl silicone oil and methylphenyl silicone oil.

(AO-1)

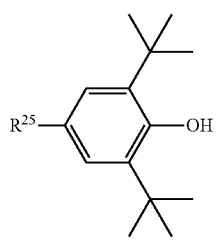

(AO-2)

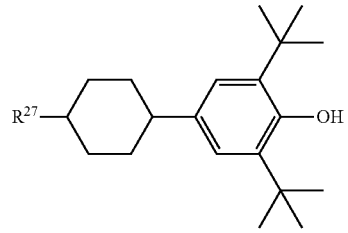

(AO-3)

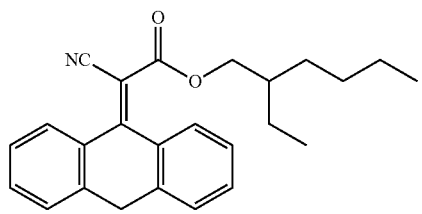

(AO-4)

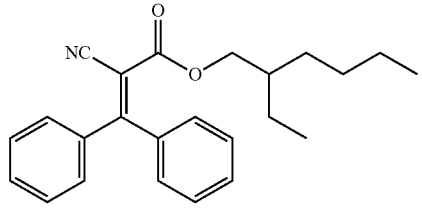

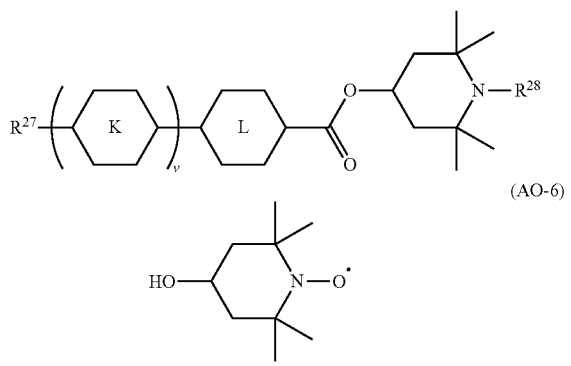

(AO-5)

(AO-6)

In compound (AO-1), $R^{25}$ is alkyl having 1 to 20 carbons, alkoxy having 1 to 20 carbons, —COOR$^{26}$ or —CH$_2$CH$_2$COOR$^{26}$; wherein, $R^{26}$ is alkyl having 1 to 20 carbons. In compounds (AO-2) and (AO-5), $R^{27}$ is alkyl having 1 to 20 carbons. In compound (AO-5), ring K and ring L are 1,4-cyclohexylene or 1,4-phenylene, v is 0, 1 or 2, and $R^{28}$ is hydrogen, methyl or O.

Composition (1) can be used for a guest host (GH) mode by addition of a dichroic dye of a merocyanine type, a stylyl type, an azo type, an azomethine type, an azoxy type, a quinophthalone type, an anthraquinone type, a tetrazine type or the like.

In composition (1), the maximum temperature can be adjusted to be approximately 70° C. or higher and the minimum temperature can be adjusted to be approximately −10° C. or lower by suitably adjusting a kind and a ratio of component compounds, and therefore the temperature range of the nematic phase is wide. Accordingly, a liquid crystal display device including the composition can be used in the wide temperature range.

In composition (1), the optical anisotropy can be adjusted to the range of approximately 0.10 to approximately 0.13 or to the range of approximately 0.05 to approximately 0.18 by suitably adjusting a kind and a ratio of component compounds. In a similar manner, the dielectric anisotropy can be adjusted to the range of approximately −5.0 to approximately −2.0. Preferred dielectric anisotropy is in the range of approximately −4.5 to approximately −2.5. Composition (1) having the dielectric anisotropy in the range can be preferably used for a liquid crystal display device that operates in the IPS mode, VA mode or PSA mode.

3. Liquid Crystal Display Device

Composition (1) can be used for an AM device. The composition can also be used for a PM device. The composition can be used for an AM device and a PM device having a mode such as PC, TN, STN, ECB, OCB, IPS, FFS, VA, PSA or FPA. Use for an AM device having the TN, OCB, IPS or FFS mode is particularly preferred. In an AM device having the IPS mode or FFS mode, alignment of liquid crystal molecules in a state in which no voltage is applied may be parallel or perpendicular to a panel substrate. The devices may be of a reflective type, a transmissive type or a transflective type. Use for a transmissive device is preferred. The composition can also be used for an amorphous silicon-TFT device or a polycrystal silicon-TFT device. The composition can also be used for a nematic curvilinear aligned phase (NCAP) device prepared by microencapsulating the composition, or a polymer dispersed (PD) device in which a three-dimensional network-polymer is formed in the composition.

Composition (1) has the negative dielectric anisotropy, and therefore can be suitably used for a liquid crystal display device that has an operating mode such as the VA mode, the IPS mode or the PSA mode, and is driven by an AM mode. The composition can be particularly preferably used for a liquid crystal display device that has the VA mode and driven by the AM mode.

In a liquid crystal display device that operates in the TN mode, VA mode or the like, a direction of an electric field is perpendicular to a direction of a liquid crystal layer. On the other hand, in a liquid crystal display device that operates in the IPS mode or the like, the direction of the electric field is parallel to the direction of the liquid crystal layer. A structure of a liquid crystal display device that operates in the VA mode is reported in K. Ohmuro, S. Kataoka, T. Sasaki and Y. Koike, SID '97 Digest of Technical Papers, 28, 845 (1997). A structure of a liquid crystal display device that operates in the IPS mode is reported in WO 91/10936 A (family: U.S. Pat. No. 5,576,867 B).

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

The invention will be described in greater detail by way of Examples. The invention is not limited by the Examples.

1-1. Example of Compound (1-1)

Compound (1) was prepared by procedures as described below. A prepared compound was identified by a method such as NMR analysis. Physical properties of the compound were measured by methods as described below.

NMR Analysis

As a measuring apparatus, DRX-500 (made by Bruker BioSpin Corporation) was used. In $^1$H-NMR measurement, a sample was dissolved in a deuterated solvent such as CDCl$_3$, and measurement was carried out under conditions of room temperature, 500 MHz and 16 times of accumulation. Tetramethylsilane was used as an internal standard. In $^{19}$F-NMR measurement, measurement was carried out under conditions of 24 times of accumulation using CFCl$_3$ as an internal standard. In the explanation of nuclear magnetic resonance spectra, s, d, t, q, quin, sex, m and br stand for a singlet, a doublet, a triplet, a quartet, a quintet, a sextet, a multiplet, and br being broad, respectively.

Sample for Measurement

Upon measuring a phase structure and a transition temperature, a liquid crystal compound itself was used as a sample. Upon measuring physical properties such as a maximum temperature of a nematic phase, viscosity, optical anisotropy and dielectric anisotropy, a composition prepared by mixing the compound with a base liquid crystal was used as a sample.

When the sample prepared by mixing the compound with the base liquid crystal was used, measurement was carried out according to the method described below. The sample was prepared by mixing 15% by weight of the compound and 85% by weight of the base liquid crystal. An extrapolated value was calculated from a measured value of the sample, according to an extrapolation method, based on an equation below, and the value was described. [Extrapolated value]=(100×[measured value of a sample]−[% of a base liquid crystal]×[measured value of the base liquid crystal])/[% of the compound].

When crystals (or a smectic phase) precipitated at 25° C. even at the ratio of the compound to the base liquid crystal, a ratio of the compound to the base liquid crystal was changed in the order of (10% by weight:90% by weight), (5% by weight:95% by weight) and (1% by weight:99% by weight). Physical properties of a sample were measured at a ratio at which no crystals (or no smectic phase) precipitated at 25° C. In addition, unless otherwise noted, the ratio of the compound to the base liquid crystal is 15% by weight:85% by weight.

As the base liquid crystal, base liquid crystal (i) below was used. Ratios of components of base liquid crystal (i) are expressed in terms of % by weight.

$C_3H_7$—⬡—COO—⌬—$OC_2H_5$   17.2 wt %

$C_3H_7$—⬡—COO—⌬—$OC_4H_9$   27.6 wt %

$C_4H_9$—⬡—COO—⌬—$OC_2H_5$   20.7 wt %

$C_5H_{11}$—⬡—COO—⌬—$OCH_3$   20.7 wt %

$C_5H_{11}$—⬡—COO—⌬—$OC_2H_5$   13.8 wt %

Measuring Method

Physical properties of a compound were measured according to the methods described below. Most of the methods are applied as described in the Standard of the Japan Electronics and Information Technology Industries Association (hereinafter, abbreviated as JEITA) (JEITA EIAJ ED-2521A) discussed and established by JEITA, or modified thereon. No TFT was attached to a TN device used for measurement.

(1) Phase Structure

For measuring a melting point, a sample was placed on a hot plate of apparatus, (FP-52 Hot Stage made by Mettler-Toledo International Inc.) which was equipped with a polarizing microscope, and a state of phase and a change thereof were observed with the polarizing microscope while the sample was heated at a rate of 3° C. per minute, and a kind of the phase was identified.

(2) Transition Temperature (° C.)

A sample was heated and cooled, at a rate of 3° C. per minute, using DSC-7 System made by PerkinElmer, Inc. or Diamond DSC System, which are differential scanning calorimeters. A starting point of an endothermic peak or an exothermic peak caused by a phase change of the sample was determined by extrapolation, and thus a transition temperature was determined Temperature at which a compound undergoes transition from a solid to a liquid crystal phase such as a smectic phase or a nematic phase is occasionally abbreviated as "minimum temperature of the liquid crystal phase." Temperature at which a compound undergoes transition from a liquid crystal phase to a liquid is occasionally abbreviated as "clearing point."

Crystals were expressed as C, and when kinds of the crystals were distinguishable, each of the crystals was expressed as $C_1$ or $C_2$. The smectic phase and the nematic phase were expressed as S and N, respectively. When smectic A phase, smectic B phase, smectic C phase and smectic F phase were distinguishable among the smectic phases, the phases were expressed as $S_A$, $S_B$, $S_C$ or $S_F$, respectively. A liquid (isotropic) was expressed as I. A transition temperature was expressed as "C 50.0 N 100.0 I," for example. The expression indicates that a transition temperature from a crystal to a nematic phase is 50.0° C., and a transition temperature from the nematic phase to a liquid is 100.0° C.

(3) Compatibility at a Low Temperature:

Samples, mixtures of the base liquid crystal and a compound measured, in which the ratios of the compound were 20% by weight, 15% by weight, 10% by weight, 5% by weight, 3% by weight and 1% by weight, respectively, were prepared, and put in vial glasses. After the glass vials were kept in freezers at −10° C. or −20° C. for a predetermined period of time, whether or not crystals (or a smectic phase) precipitated was observed.

(4) Maximum Temperature of a Nematic Phase ($T_{NI}$ or NI; ° C.)

A sample was placed on a hot plate of a melting point apparatus equipped with a polarizing microscope and was heated at a rate of 1° C. per minute. Temperature was measured when part of the sample began to change from a nematic phase to an isotropic liquid. A higher limit of a temperature range of the nematic phase may be occasionally abbreviated as "maximum temperature." When the sample was a mixture of a compound and the base liquid crystal, the maximum temperature was expressed as a symbol $T_{NI}$. When the sample was a mixture of a compound and component B and so forth, the maximum temperature was expressed as a symbol NI.

(5) Minimum Temperature of a Nematic Phase ($T_C$; ° C.)

Samples each having a nematic phase were kept in freezers at temperatures of 0° C., −10° C., −20° C., −30° C. and −40° C. for 10 days, and then liquid crystal phases were observed. For example, when a sample maintained the nematic phase at −20° C. and changed to crystals or a smectic phase at −30° C., $T_C$ was expressed as $T_C$≤−20° C. A lower limit of the temperature range of the nematic phase may be occasionally abbreviated as "minimum temperature."

(6) Viscosity (Bulk Viscosity; η; measured at 20° C.; mPa·s)

A cone-plate (E-type) rotational viscometer was used for measurement.

(7) Viscosity (Rotational Viscosity; γ1; Measured at 25° C.; mPa·s)

Measurement was carried out according to the method described in M. Imai et al., Molecular Crystals and Liquid Crystals, Vol. 259, p. 37 (1995). A sample was put in a VA device in which a distance (cell gap) between two glass substrates was 20 micrometers. A voltage was applied stepwise to the device in the range of 30 V to 50 V at an increment of 1 V. After a period of 0.2 second with no voltage, a voltage was applied repeatedly under the conditions of only one rectangular wave (rectangular pulse; 0.2 second) and no voltage (2 seconds). A peak current and a peak time of a transient current generated by the applied voltage were measured. A value of rotational viscosity was obtained from the measured values and calculation equation (8) on page 40 of the paper presented by M. Imai et al. As dielectric anisotropy required for the calculation, a value measured in a section of dielectric anisotropy described below was used.

(8) Optical Anisotropy (Refractive Index Anisotropy; Δn; Measured at 25° C.)

Measurement was carried out by an Abbe refractometer having a polarizing plate mounted on an ocular, when a wavelength of the light for measurements was set at 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of refractive index anisotropy was calculated from an equation: Δn=n∥−n⊥.

(9) Dielectric Anisotropy (Δε; Measured at 25° C.)

A value of dielectric anisotropy was calculated from an equation: Δε=ε∥−ε⊥. A dielectric constant (ε∥ and ε⊥) was measured as described below.

(1) Measurement of dielectric constant (ε∥): An ethanol (20 mL) solution of octadecyl triethoxysilane (0.16 mL) was applied to a well-cleaned glass substrate. The glass substrate was rotated with a spinner, and then heated at 150° C. for 1 hour. A sample was put in a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant (ε∥) in the major axis direction of liquid crystal molecules was measured.

(2) Measurement of dielectric constant (ε⊥): A polyimide solution was applied to a well-cleaned glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant (ε⊥) in the minor axis direction of the liquid crystal molecules was measured.

(10) Elastic Constant ($K_{11}$ and $K_{33}$; Measured at 25° C.; pN)

Elastic Constant Measurement System Model EC-1 made by TOYO Corporation was used for measurement. A sample was put in a vertical alignment device in which a distance (cell gap) between two glass substrates was 20 micrometers. An electric charge of 20 V to 0 V was applied to the device, and electrostatic capacity and applied voltage were measured. Values of electrostatic capacity (C) and applied voltage (V) were fitted to equation (2.98) and equation (2.101) on page 75 of the "Liquid Crystal Device Handbook (Ekisho Debaisu Handobukku, in Japanese)" (The Nikkan Kogyo Shimbun, Ltd.), and a value of elastic constant was obtained from equation (2.100).

(11) Threshold Voltage (Vth; Measured at 25° C.; V)

An LCD-5100 luminance meter made by Otsuka Electronics Co., Ltd. was used for measurement. A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. A voltage (60 Hz, rectangular waves) applied to the device was increased stepwise from 0 V to 20 V at an increment of 0.02 V. On the occasion, the device was irradiated with light from a direction perpendicular to the device, and an amount of light transmitted through the device was measured. A voltage-transmittance curve was prepared, in which 100% of transmittance was regarded as a maximum amount of light and 0% of transmittance was regarded as a minimum amount of light. A threshold voltage was defined as a voltage at 90% of transmittance.

(12) Voltage Holding Ratio (VHR-1; Measured at 25° C.; %)

A TN device used for measurement had a polyimide alignment film when a distance (cell gap) between two glass substrates was 5 micrometers. A sample was put in the device, and then the device was sealed with an ultraviolet-curable adhesive. The TN device was charged by applying pulse voltage (60 microseconds at 5 V). A decaying voltage was measured for 16.7 milliseconds with a high-speed voltmeter, and area A between a voltage curve and a horizontal axis in a unit cycle was determined Area B was an area without decay. A voltage holding ratio is a percentage of area A to area B.

(13) Voltage Holding Ratio (VHR-2; Measured at 80° C.; %)

A TN device used for measurement had a polyimide alignment film when a distance (cell gap) between two glass plates was 5 micrometers. A sample was put in the device, and then the device was sealed with an ultraviolet-curable adhesive. The TN device was charged by applying pulse voltage (60 microseconds at 5 V). A decaying voltage was measured for 16.7 milliseconds with a high-speed voltmeter, and area A between a voltage curve and a horizontal axis in a unit cycle was determined Area B was an area without decay. A voltage holding ratio is a percentage of area A to area B.

Raw Material

Solmix A-11 (registered trade name) is a mixture of ethanol (85.5% by weight), methanol (13.4% by weight) and isopropanol (1.1% by weight), and was purchased from Japan Alcohol Trading Company Ltd.

Example 1

Synthesis of Compound (No. 2)

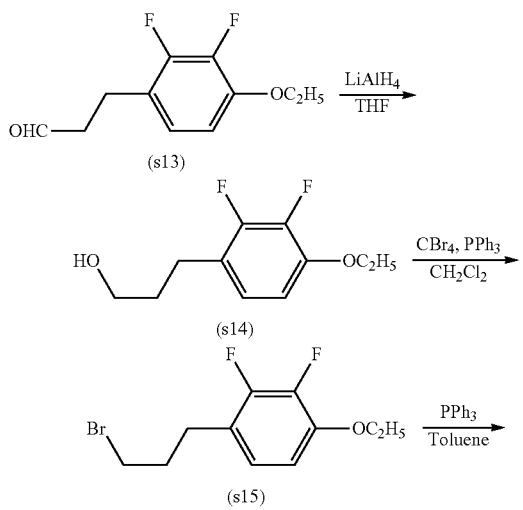

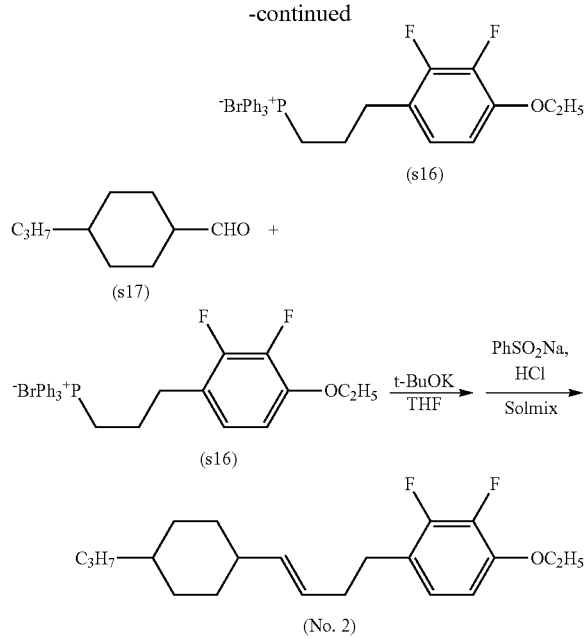

First Step

Into 100 mL of THF, 1.7 g of lithium aluminum hydride was suspended. To the suspension, 9.6 g of compound (s13) was added dropwise in the temperature range of −20° C. to −10° C., and the resulting mixture was further stirred in the temperature range for 2 hours. After confirming reaction completion by GC analysis, ethyl acetate and a saturated ammonia aqueous solution were added sequentially to the reaction liquid under ice cooling, and a precipitate was removed by Celite filtration. The resulting filtrate was extracted by ethyl acetate. The resulting organic layer was sequentially washed with water and saturated brine, and dried over anhydrous magnesium sulfate. The resulting residue was further purified by recrystallization from heptane and 9.4 g of compound (s14) was obtained. A yield of compound (s14) based on compound (s13) was 97.0%.

Second Step

Into 100 mL of methylene chloride, 9.4 g of compound (s14) and 17.1 g of triphenylphosphine were dissolved. To the solution, a solution prepared by dissolving 17.3 g of carbon tetrabromide into 100 mL of methylene chloride was slowly added dropwise at room temperature, and the resulting solution was further stirred at room temperature for 3 hours. To the reaction liquid obtained, saturated sodium bicarbonate water and ethyl acetate were added and mixed, and then the resulting solution was left to stand to be separated into an organic layer and an aqueous layer, and extraction operation was performed to the organic layer. The resulting organic layer was sequentially washed with water and saturated brine, dried over anhydrous magnesium sulfate and concentrated under reduced pressure to obtain a residue. The residue was a pale yellow solid, and was purified by column chromatography using n-heptane as an eluent and silica gel as a packing medium to give 11.5 g of compound (s15). A yield based on compound (s14) was 94.8%.

Third Step

Under a nitrogen atmosphere, 11.5 g of compound (s15), 100 mL of toluene and 21.6 g of triphenylphosphine were put in a reaction vessel, and the resulting liquid was refluxed on heating for 5 hours. The resulting reaction liquid was cooled to 25° C., a precipitate was filtered off and then an unreacted raw material was washed away three times with toluene. The resulting colorless solid was dried and 17.6 g of compound (s16) was obtained. A yield based on compound (s15) was 78.9%.

Fourth Step

Under a nitrogen atmosphere, 13.6 g of well-dried compound (s16) and 100 mL of THF were mixed, and the resulting mixture was cooled to −10° C. Then, 1.4 g of potassium t-butoxide (t-BuOk) was charged thereinto in two portions, keeping the temperature range of −10° C. to −5° C. After the resulting mixture was stirred at −10° C. for 60 minutes, 3.3 g of compound (s17) dissolved into 30 mL of THF was added dropwise thereto in the temperature range of −10 to −5° C. After the resulting mixture was stirred at 0° C. for 30 minutes, the resulting reaction liquid was poured into a mixed solution of 100 mL of water and 200 mL of toluene, and mixed, and then left to stand to be separated into two layers of an organic layer and an aqueous layer, and extraction operation was performed to the organic layer. The resulting organic layer was separated, washed with water and dried over anhydrous magnesium sulfate. The solution was concentrated under reduced pressure, and the resulting residue was purified by column chromatography using toluene as an eluent and silica gel as a packing medium. Then, to the purified substance 6.1 g of sodium benzenesulfonate dihydrate and 100 mL of Solmix A-11 were mixed. Then, after 20 mL of 6 N HCl solution was added thereto, the resulting mixture was refluxed on heating for 2 hours. After 100 mL of water and 100 mL of toluene were added to the resulting reaction liquid, and mixed, the resulting liquid was left to stand to be separated into two layers of an organic layer and an aqueous layer, and extraction operation was performed to the organic layer. The resulting organic layer was separated, washed with water, saturated sodium bicarbonate water and water, one by one, and dried over anhydrous magnesium sulfate. Then, the solvent was distilled off under reduced pressure and the resulting residue was purified by column chromatography using toluene as an eluent and silica gel as a packing medium. Further, the residue was purified by recrystallization from a mixed solvent of ethyl acetate and Solmix A-11 (ethyl acetate:Solmix=1:4 (volume ratio)) and 4.0 g of compound (No. 2) was obtained. A yield based on compound (s16) was 55.3%.

$^1$H-NMR (δ ppm; CDCl$_3$): 6.88 (t, 1H), 6.74 (t, 1H), 5.45 (m, 2H), 4.18 (q, 2H), 2.73 (t, 2H), 2.33 (q, 2H), 1.90 (m, 1H), 1.79 (dd, 4H), 1.53 (t, 3H), 1.40 (m, 2H), 1.24 (m, 3H), 1.10 (q, 2H), 0.97 (m, 5H).

Physical properties of compound (No. 2) were as described below.

Transition temperature: C 40.9 I.

$T_{NI}$=−4.1° C.; Δn=0.087; Δε=−4.60; η=21.1 mPa·s.

Example 2

Various compounds were prepared using corresponding starting materials according to the techniques described in Example 1, and confirmed they are target compounds.

Compound (No. 52)

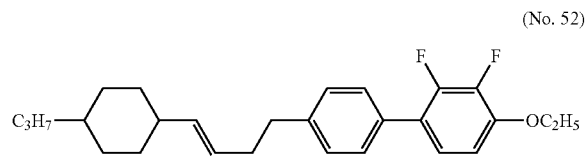

(No. 52)

$^1$H-NMR (δ ppm; CDCl$_3$): 7.41 (dd, 2H), 7.24 (d, 2H), 7.08 (td, 1H), 6.78 (td, 1H), 5.41 (m, 2H), 4.15 (q, 2H), 2.70 (t, 2H), 2.32 (m, 2H), 1.85 (m, 1H), 1.75 (m, 4H), 1.48 (t, 3H), 1.29 (m, 2H), 1.11 (m, 7H), 0.90 (t, 3H).

Physical properties of compound (No. 52) were as described below.

Transition temperature: C 84.0 N 136.3 I.

$T_{NI}$=135.9° C.; Δn=0.186; Δε=−4.58; η=45.6 mPa·s.

Compound (No. 63)

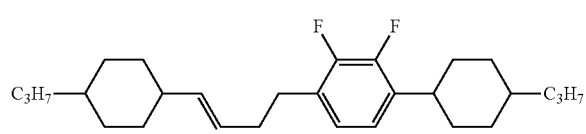

(No. 63)

$^1$H-NMR (δ ppm; CDCl$_3$): 6.84 (m, 2H), 5.35 (m, 2H), 2.80 (t, 1H), 2.67 (t, 2H), 2.25 (q, 2H), 1.85 (d, 5H), 1.72 (d, 4H), 1.66 (d, 2H), 1.45 (q, 2H), 1.40-1.25 (m, 4H), 1.24-0.96 (m, 8H), 0.87 (m, 8H).

Physical properties of compound (No. 63) were as described below.

Transition temperature: C 41.6 N 92.6 I.

$T_{NI}$=92.6° C.; Δn=0.101; Δε=−2.32; η=26.3 mPa·s.

Compound (No. 72)

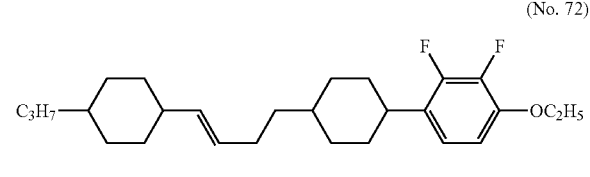

(No. 72)

$^1$H-NMR (δ ppm; CDCl$_3$): 6.83 (td, 1H), 6.66 (td, 1H), 5.35 (m, 2H), 4.08 (q, 2H), 2.74 (tt, 1H), 2.00 (m, 2H), 1.85 (m, 5H), 1.72 (m, 4H), 1.43 (m, 5H), 1.30 (m, 5H), 1.15 (m, 3H), 1.12-1.00 (m, 4H), 0.90 (m, 2H), 0.86 (t, 3H).

Physical properties of compound (No. 72) were as described below.

Transition temperature: C 97.4 N 132.6 I.

$T_{NI}$=124.6° C.; Δn=0.117; Δε=−5.11; η=40.7 mPa·s.

Example 3

Compounds (No. 1) to (No. 260) shown below can be prepared in a manner similar to the synthesis methods as described in Examples 1 to 2. Attached data were determined according to the methods described above. When a transition temperature was measured, the compound itself was used as the sample. When maximum temperature ($T_{NI}$), optical anisotropy (Δn) and dielectric anisotropy (Δε) were measured, a mixture of the compound (15% by weight) and base liquid crystal (i) (85% by weight) was used as the sample. From the measured values, extrapolated values were calculated according to the extrapolation method described above, and the calculated values were described.

| No. | |
|---|---|
| 1 | 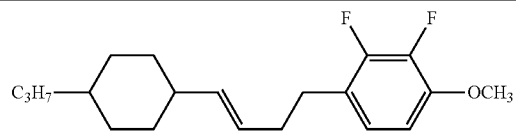 |
| 2 | 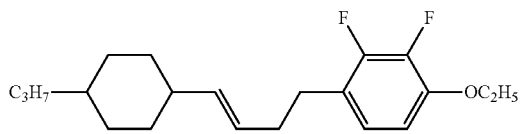 |
| | C 40.91<br>$T_{NI}$; −9.4° C., Δ ε; −4.95, Δ n; 0.059, η; 22.8 |
| 3 | 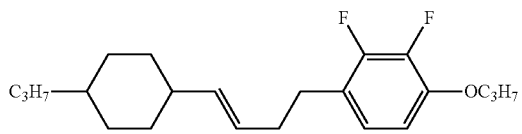 |
| 4 | 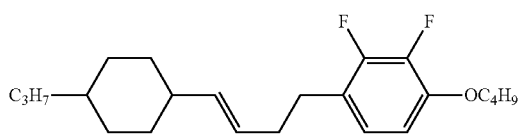 |
| 5 | 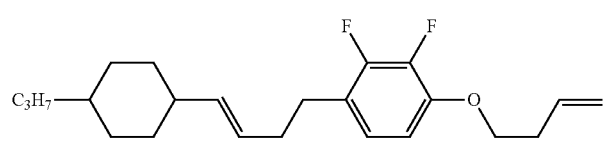 |

| No. | |
|---|---|
| 6 |  |
| 7 | 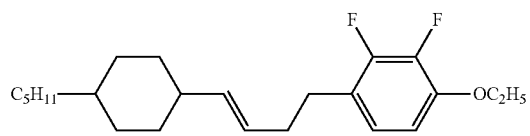 |
| 8 | 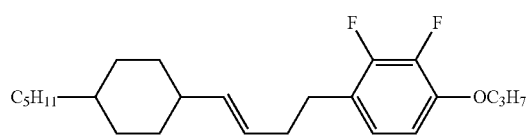 |
| 9 | 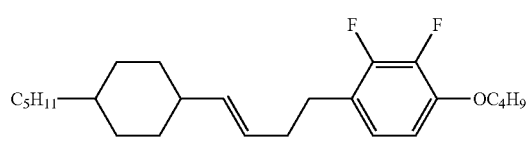 |
| 10 | 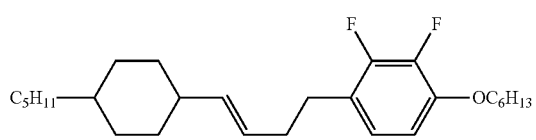 |
| 11 | 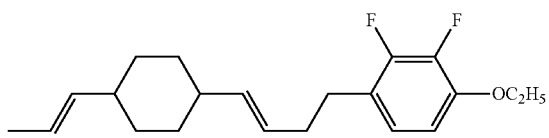 [SMILES: C/C=C/C1CCC(/C=C/CCc2ccc(OCC)c(F)c2F)CC1] |
| 12 | 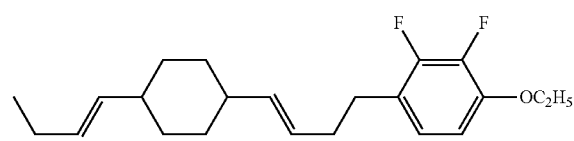 [SMILES: CC/C=C/C1CCC(/C=C/CCc2ccc(OCC)c(F)c2F)CC1] |
| 13 | 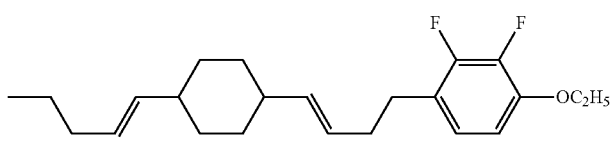 [SMILES: CCC/C=C/C1CCC(/C=C/CCc2ccc(OCC)c(F)c2F)CC1] |
| 14 | 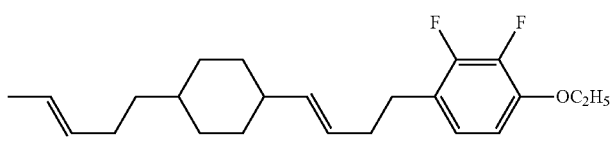 |
| 15 | 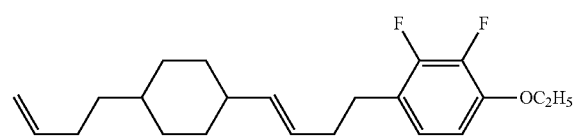 |
| 16 | 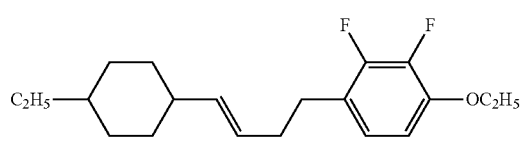 |

-continued
| No. | |
|---|---|
| 17 |  |
| 18 | 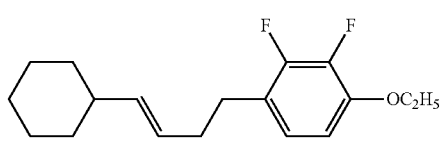 [SMILES: CCOc1ccc(CC/C=C/C2CCCCC2)c(F)c1F] |
| 19 | 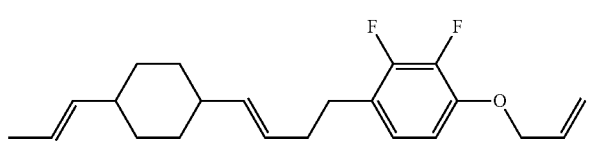 [SMILES: C=CCOc1ccc(CC/C=C/C2CCC(/C=C/C)CC2)c(F)c1F] |
| 20 | 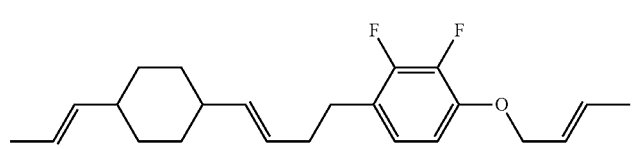 [SMILES: C/C=C/COc1ccc(CC/C=C/C2CCC(/C=C/C)CC2)c(F)c1F] |
| 21 | 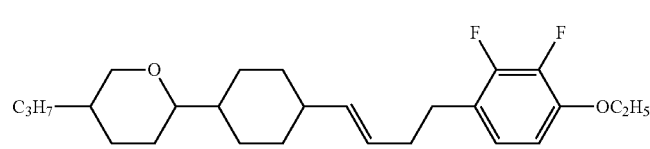 |
| 22 | 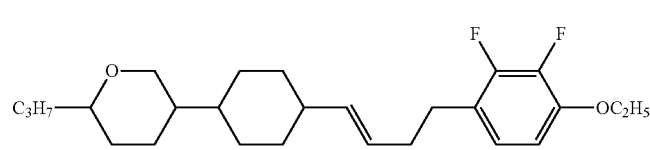 |
| 23 | 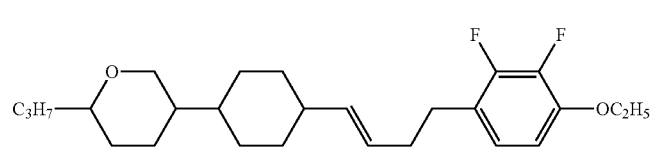 |
| 24 | 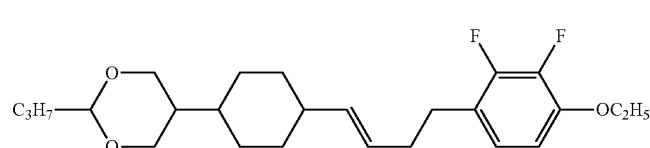 |
| 25 | 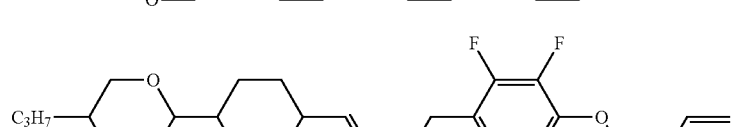 |
| 26 | 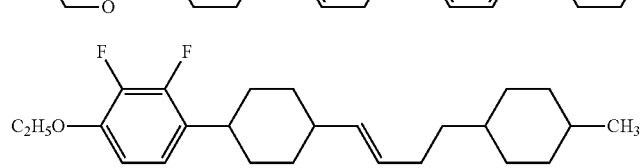 |
| 27 | 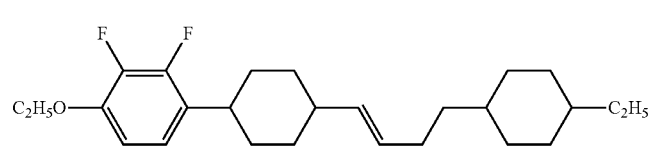 |

-continued
| No. | |
|---|---|
| 28 | 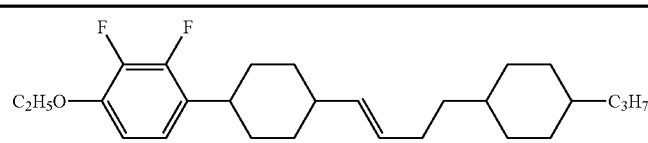 |
| 29 | 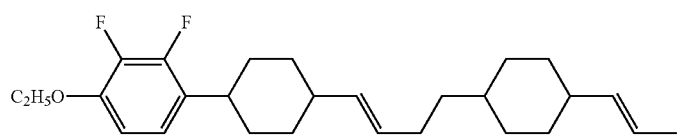 |
| 30 | 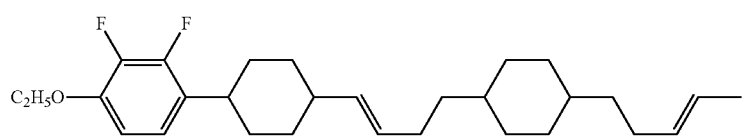 |
| 31 | 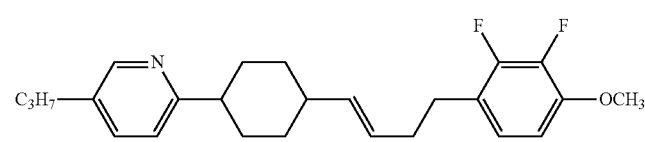 |
| 32 | 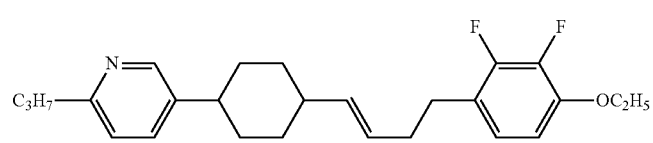 |
| 33 | 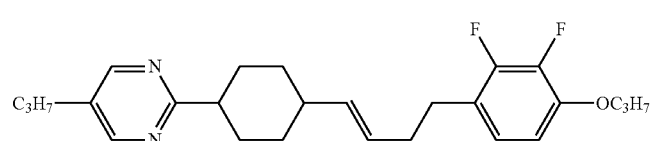 |
| 34 | 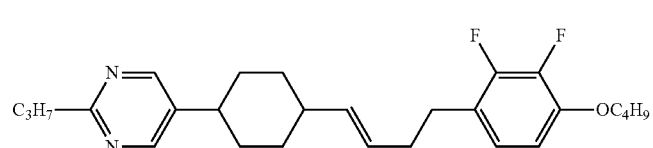 |
| 35 | 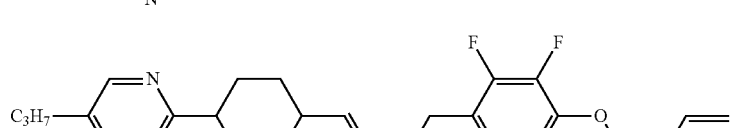 |
| 36 | 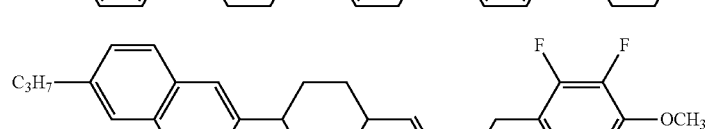 |
| 37 | 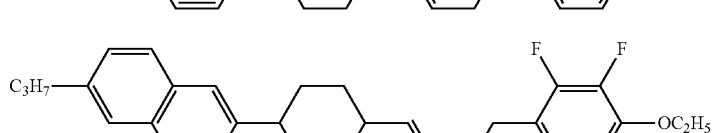 |
| 38 | 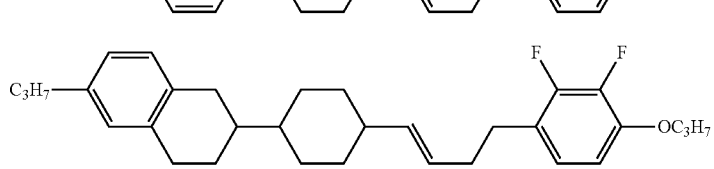 |

-continued
| No. | |
|---|---|
| 39 | 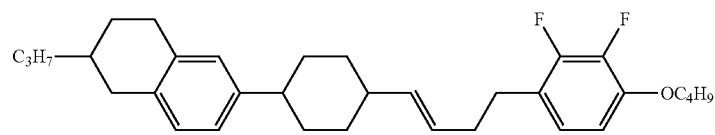 |
| 40 | 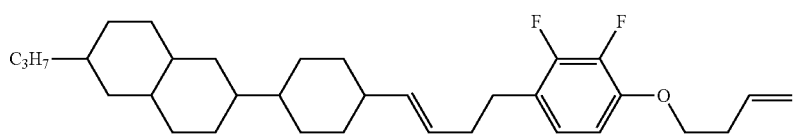 |
| 41 | 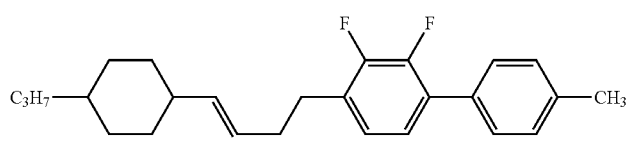 |
| 42 | 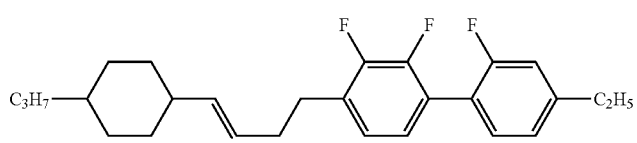 |
| 43 | 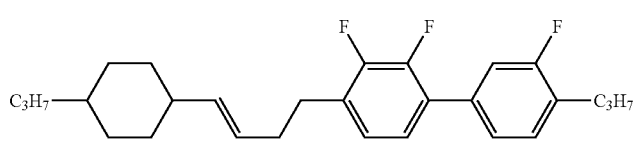 |
| 44 | 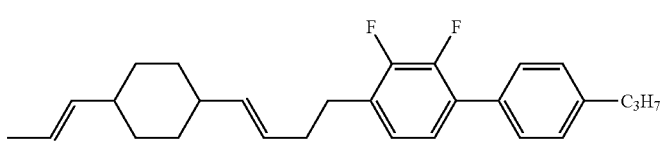 |
| 45 | 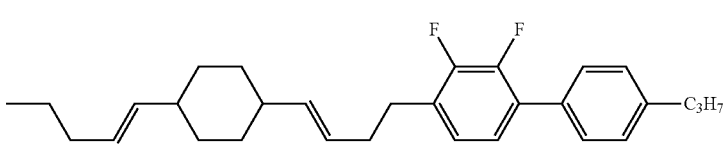 |
| 46 | 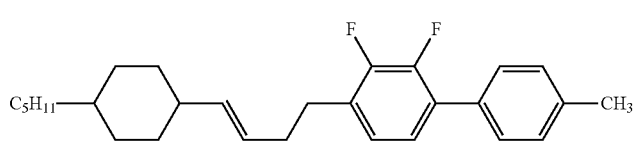 |
| 47 | 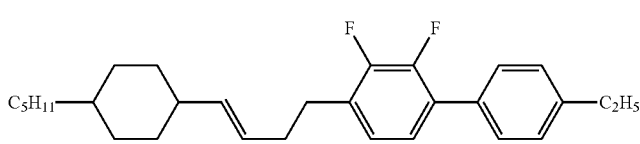 |
| 48 | 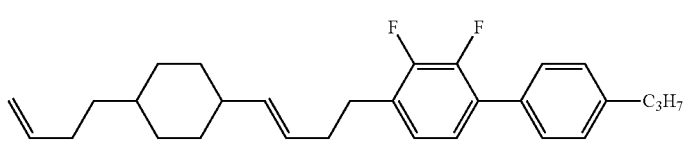 |
| 49 | 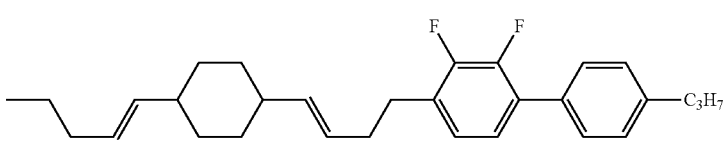 |

| No. | |
|---|---|
| 50 | 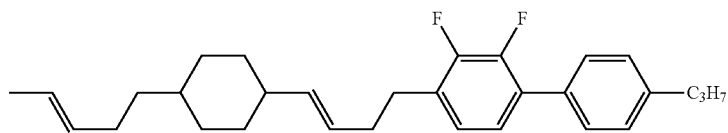 |
| 51 | 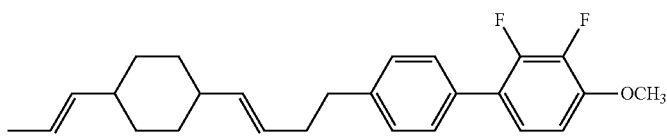 [SMILES: C/C=C/C1CCC(/C=C/CCc2ccc(-c3ccc(OC)c(F)c3F)cc2)CC1] |
| 52 | 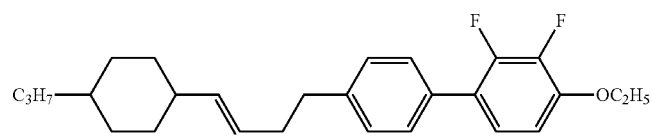<br>C 84.0 N 136.3 I<br>$T_{NI}$; 135.9° C., Δ ε; −4.58, Δ n; 0.186, η; 45.6 |
| 53 | 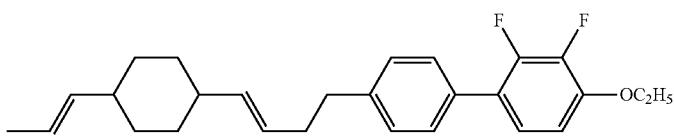 |
| 54 | 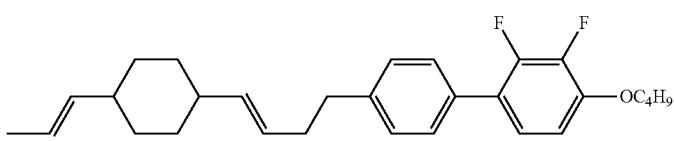 |
| 55 | 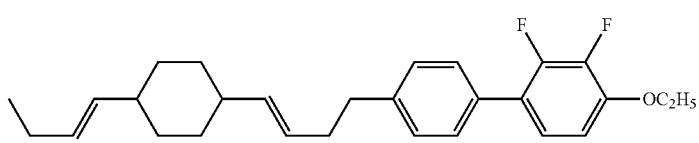 [SMILES: CC/C=C/C1CCC(/C=C/CCc2ccc(-c3ccc(OCC)c(F)c3F)cc2)CC1] |
| 56 | 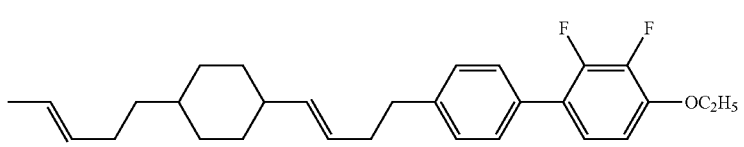 [SMILES: C/C=C/CCC1CCC(/C=C/CCc2ccc(-c3ccc(OCC)c(F)c3F)cc2)CC1] |
| 57 | 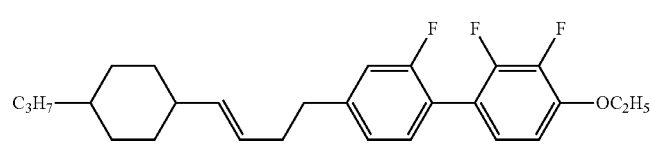 |
| 58 | 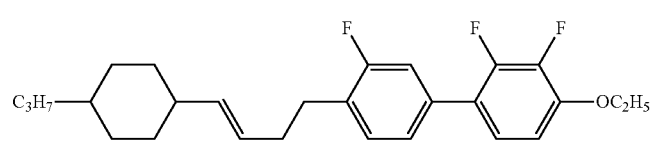 |
| 59 | 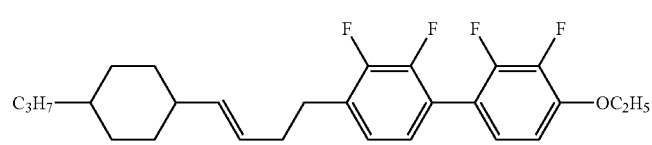 |

| No. | |
|---|---|
| 60 | 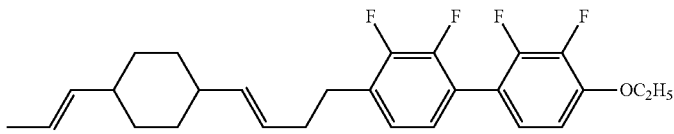 [SMILES: C/C=C/C1CCC(/C=C/CCc2ccc(-c3ccc(OCC)c(F)c3F)c(F)c2F)CC1] |
| 61 | 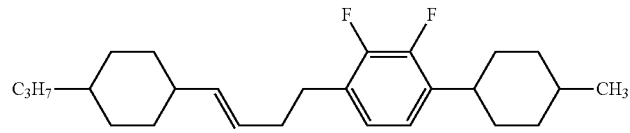 |
| 62 | 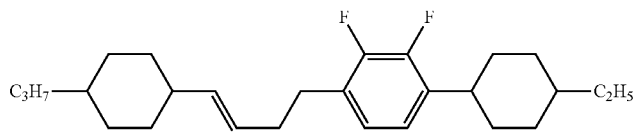 |
| 63 | 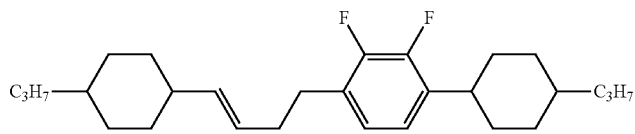 C 41.6 N 92.6 I<br>$T_{NI}$; 92.6° C., Δ ϵ; −2.32, Δ n; 0.101, η; 26.3 |
| 64 | 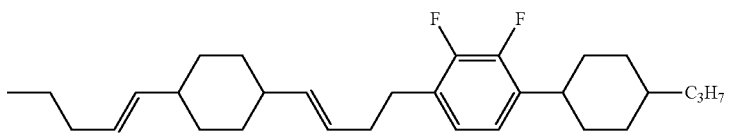 |
| 65 | 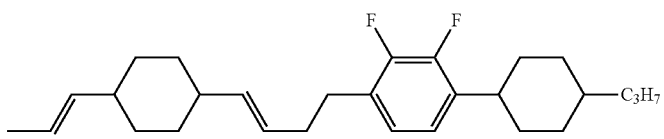 |
| 66 | 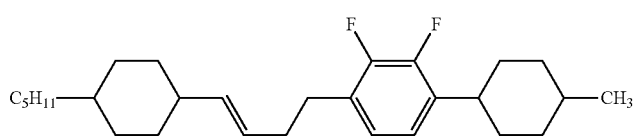 |
| 67 | 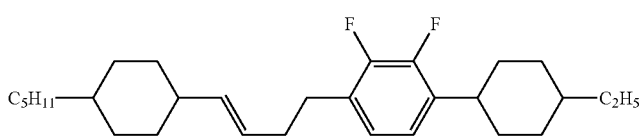 |
| 68 | 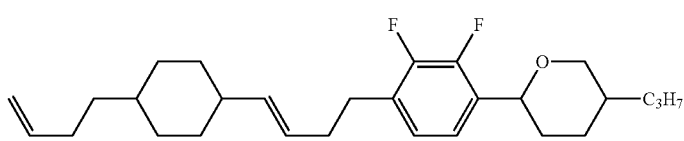 |
| 69 | 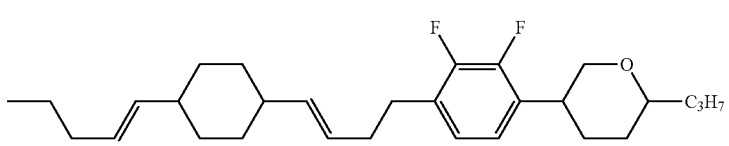 |

-continued
| No. | |
|---|---|
| 70 | 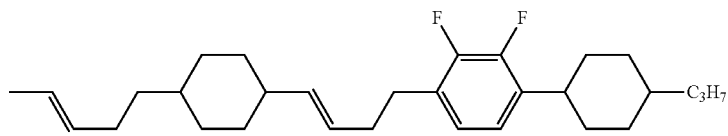 |
| 71 | 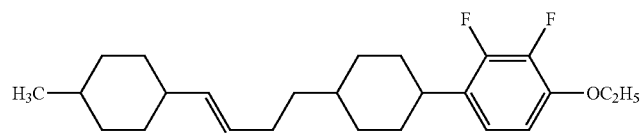 [SMILES: CCOc1ccc(C2CCC(CC/C=C/C3CCC(C)CC3)CC2)c(F)c1F] |
| 72 | 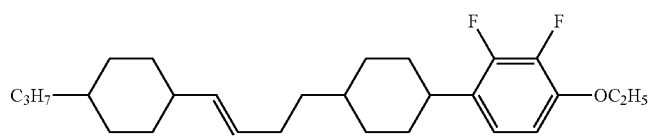 |
C 97.4 N 132.9 I
$T_{NI}$; 124.6° C., Δ ε; −5.11, Δ n; 0.117, η; 40.7
| | |
|---|---|
| 73 | 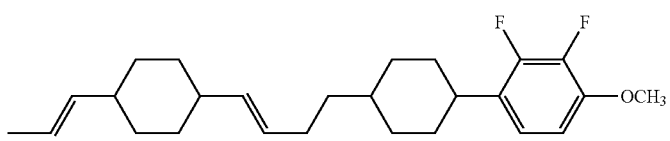 [SMILES: C/C=C/C1CCC(/C=C/CCC2CCC(c3ccc(OC)c(F)c3F)CC2)CC1] |
| 74 | 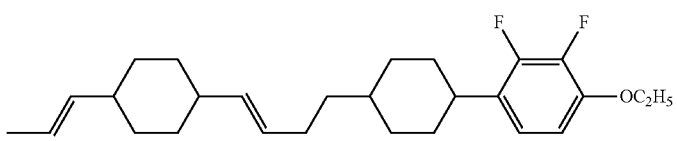 |
| 75 | 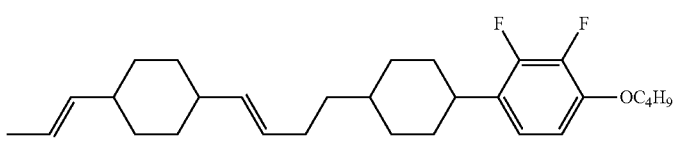 |
| 76 | 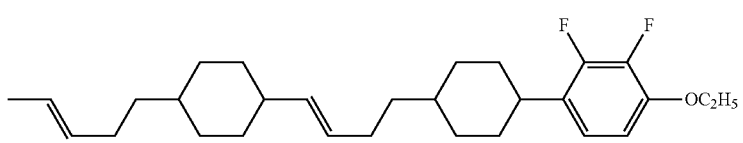 [SMILES: C/C=C/CCC1CCC(/C=C/CCC2CCC(c3ccc(OCC)c(F)c3F)CC2)CC1] |
| 77 | 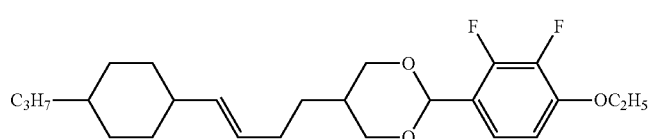 |
| 78 | 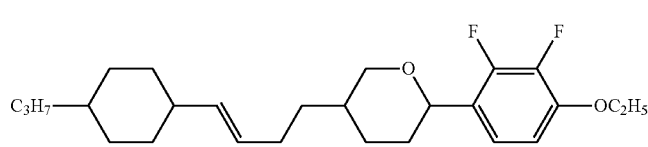 |
| 79 | 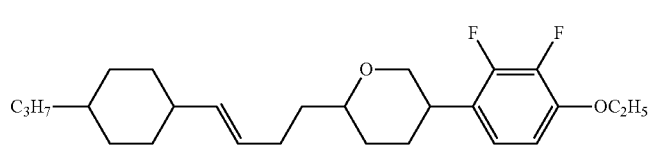 |

-continued
| No. | |
|---|---|
| 80 | 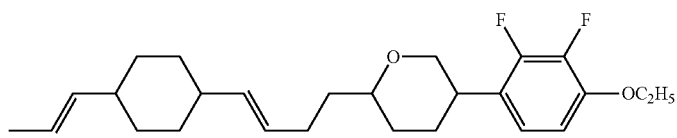 [SMILES: C/C=C/C1CCC(/C=C/CCC2CCC(c3ccc(OCC)c(F)c3F)CO2)CC1] |
| 81 | 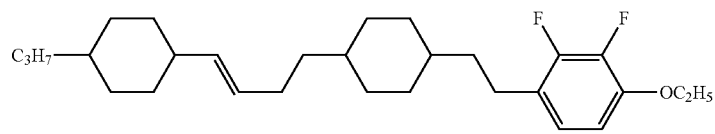 |
| 82 | 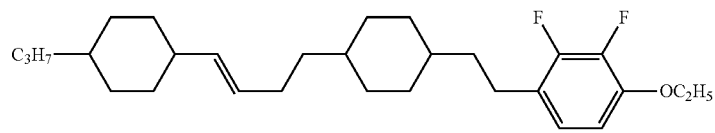 |
| 83 | 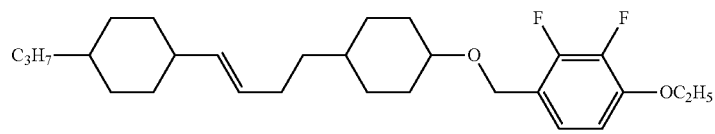 |
| 84 | 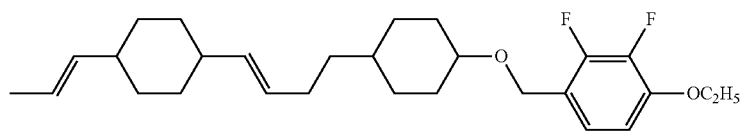 |
| 85 | 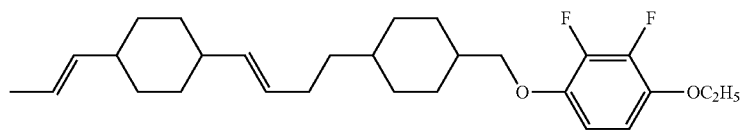 |
| 86 | 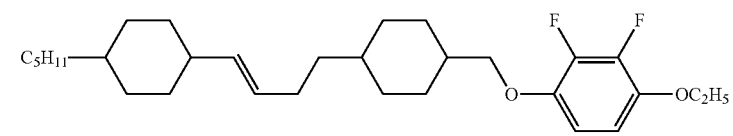 |
| 87 | 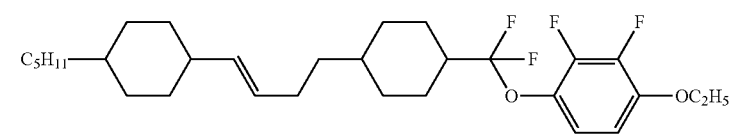 |
| 88 | 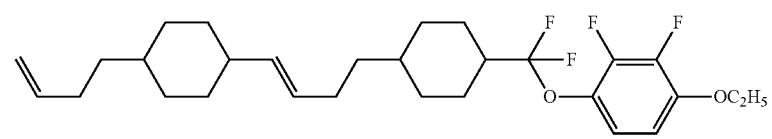 [SMILES: C=CCCC1CCC(/C=C/CCC2CCC(C(F)(F)Oc3ccc(OCC)c(F)c3F)CC2)CC1] |
| 89 | 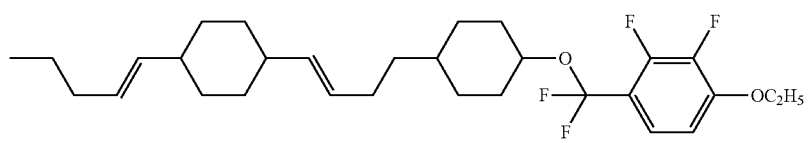 [SMILES: CCC/C=C/C1CCC(/C=C/CCC2CCC(OC(F)(F)c3ccc(OCC)c(F)c3F)CC2)CC1] |
| 90 | 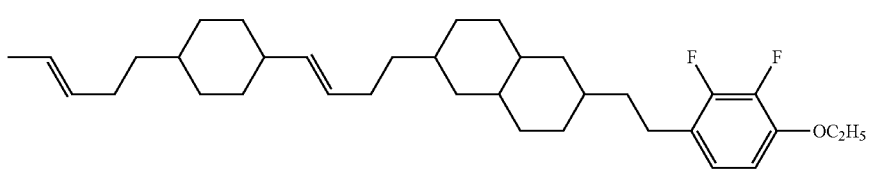 [SMILES: C/C=C/CCC1CCC(/C=C/CCC2CCC3CC(CCc4ccc(OCC)c(F)c4F)CCC3C2)CC1] |

-continued
| No. | |
|---|---|
| 91 | 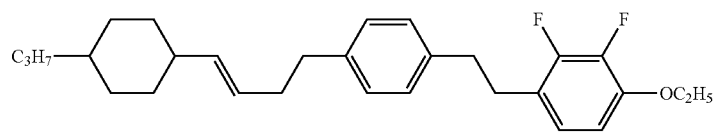 |
| 92 | 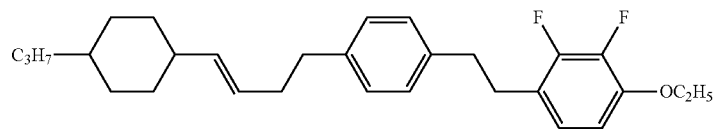 |
| 93 | 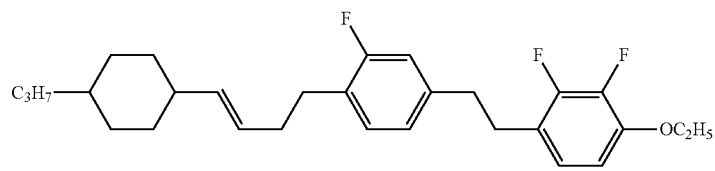 |
| 94 | 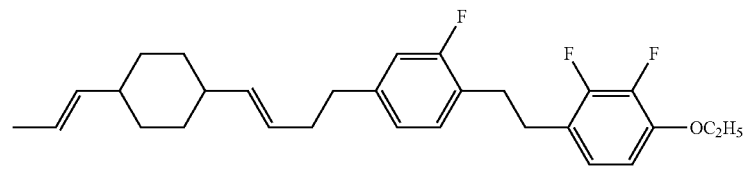 |
| 95 | 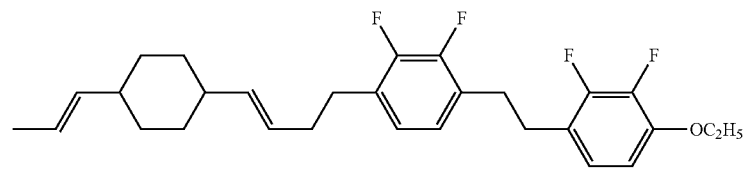 [SMILES: C/C=C/C1CCC(/C=C/CCc2ccc(CCc3ccc(OCC)c(F)c3F)c(F)c2F)CC1] |
| 96 | 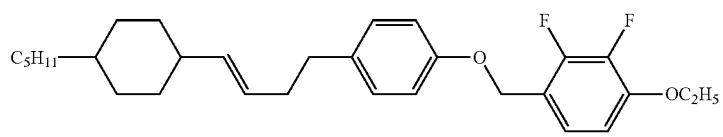 |
| 97 | 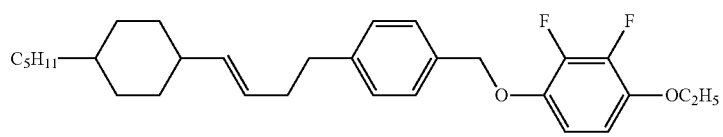 |
| 98 | 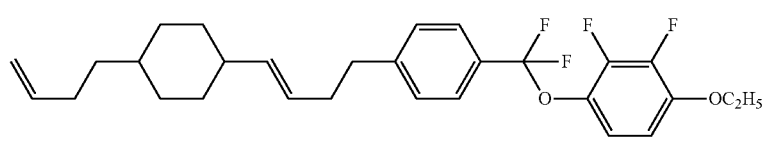 [SMILES: C=CCCC1CCC(/C=C/CCc2ccc(C(F)(F)Oc3ccc(OCC)c(F)c3F)cc2)CC1] |
| 99 | 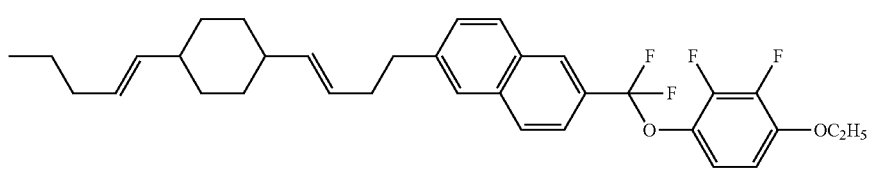 [SMILES: CCC/C=C/C1CCC(/C=C/CCc2ccc3cc(C(F)(F)Oc4ccc(OCC)c(F)c4F)ccc3c2)CC1] |
| 100 | 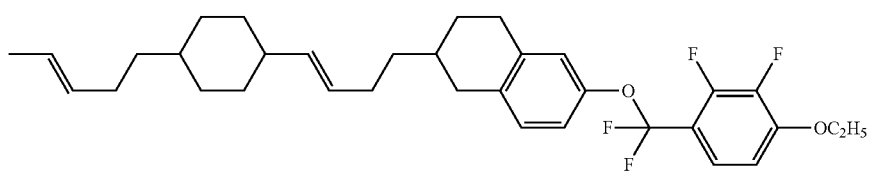 [SMILES: C/C=C/CCC1CCC(/C=C/CCC2CCc3cc(OC(F)(F)c4ccc(OCC)c(F)c4F)ccc3C2)CC1] |

| No. | |
|---|---|
| 101 |  |
| 102 | 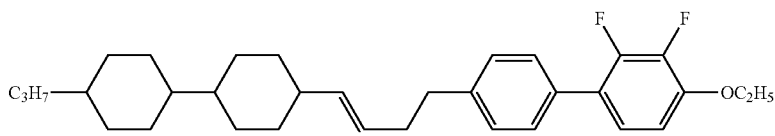 |
| 103 | 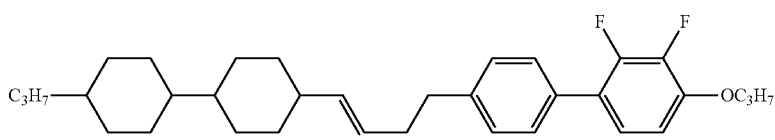 |
| 104 | 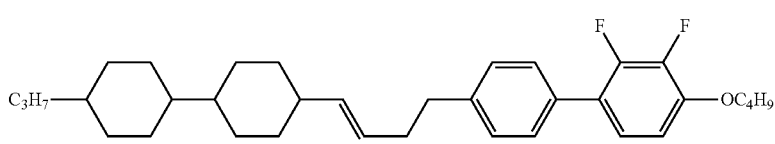 |
| 105 | 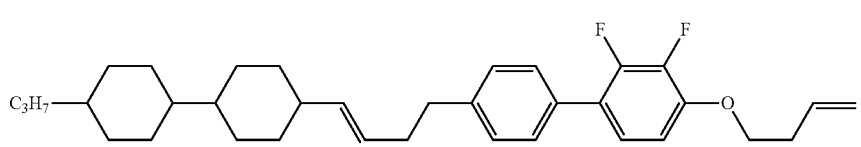 |
| 106 | 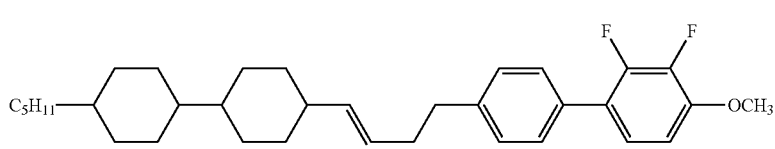 |
| 107 | 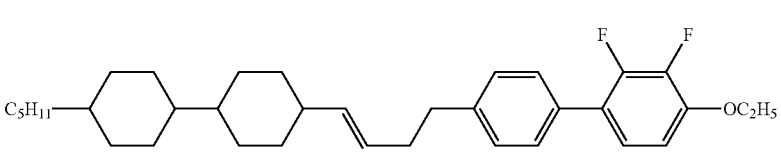 |
| 108 | 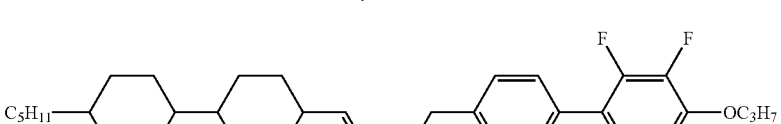 |
| 109 | 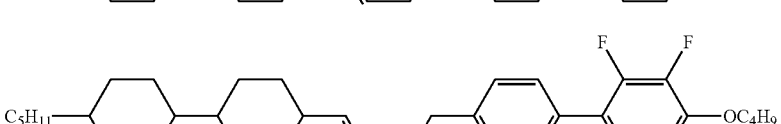 |
| 110 | 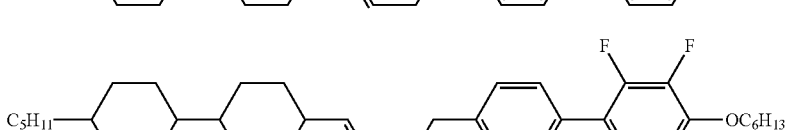 |
| 111 | 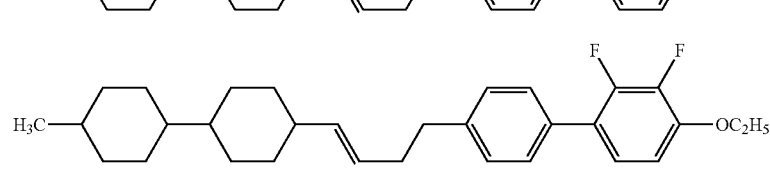 |

| No. | |
|---|---|
| 112 |  |
| 113 | 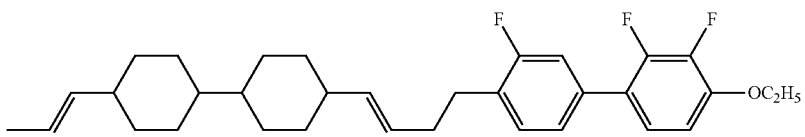 [SMILES: C/C=C/C1CCC(C2CCC(/C=C/CCc3ccc(-c4ccc(OCC)c(F)c4F)cc3F)CC2)CC1] |
| 114 | 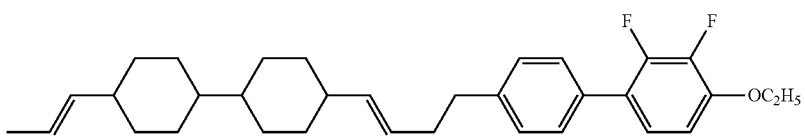 [SMILES: C/C=C/C1CCC(C2CCC(/C=C/CCc3ccc(-c4ccc(OCC)c(F)c4F)cc3)CC2)CC1] |
| 115 | 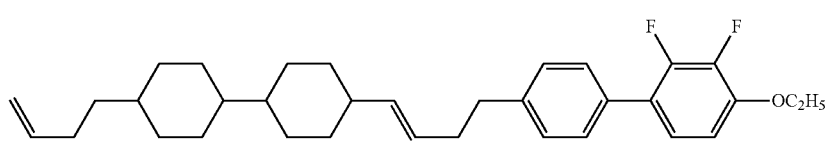 |
| 116 | 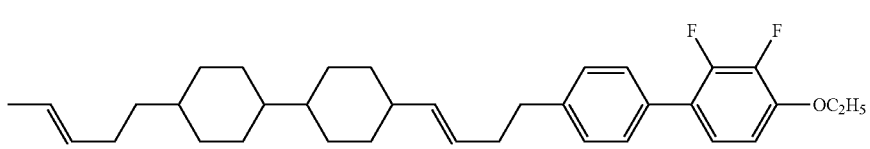 [SMILES: C/C=C/CCC1CCC(C2CCC(/C=C/CCc3ccc(-c4ccc(OCC)c(F)c4F)cc3)CC2)CC1] |
| 117 | 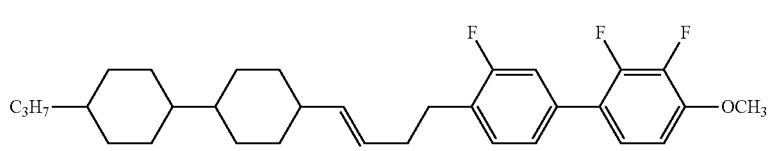 |
| 118 | 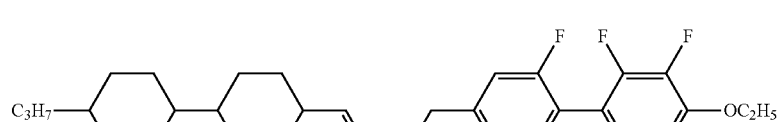 |
| 119 | 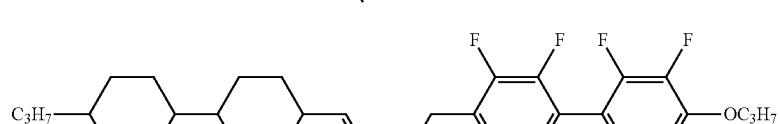 |
| 120 |  |
| 121 | 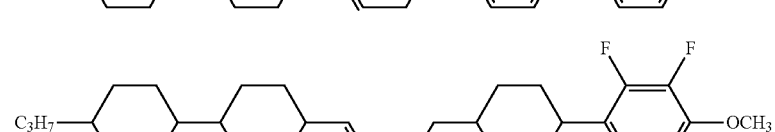 |
| 122 | 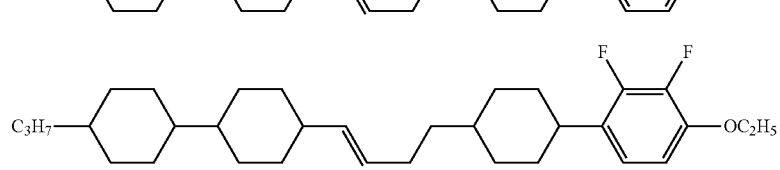 |

| No. | |
|---|---|
| 123 | 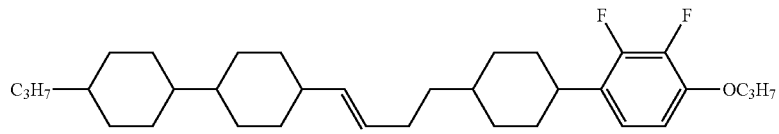 |
| 124 | 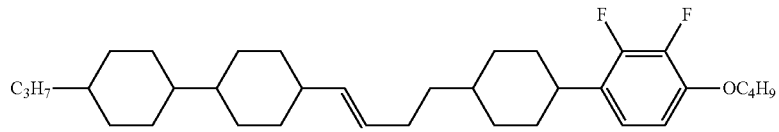 |
| 125 | 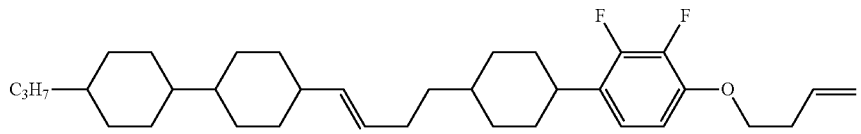 |
| 126 | 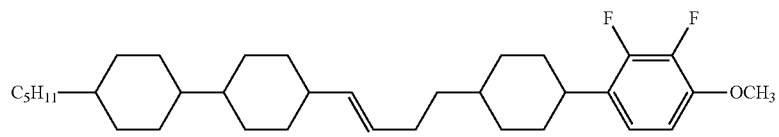 |
| 127 | 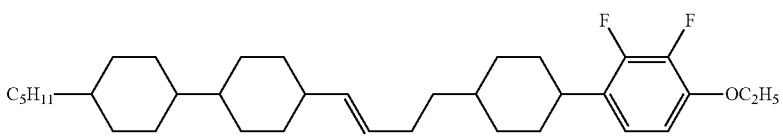 |
| 128 | 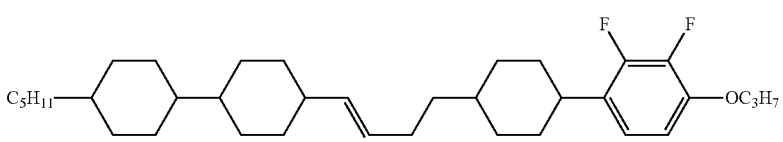 |
| 129 | 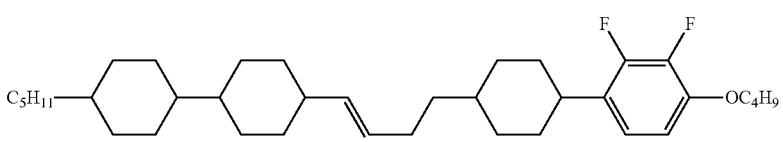 |
| 130 | 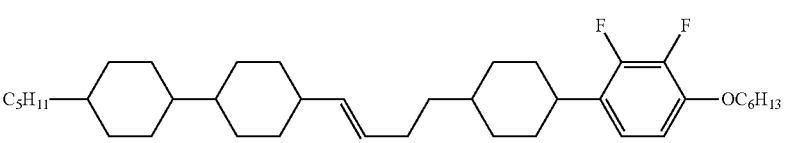 |
| 131 | 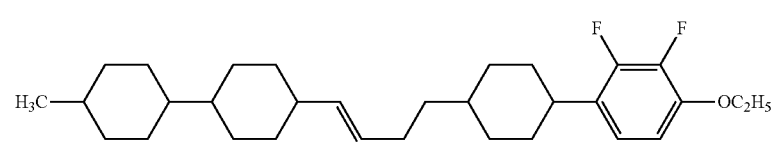 [SMILES: CCOc1ccc(C2CCC(CC/C=C/C3CCC(C4CCC(C)CC4)CC3)CC2)c(F)c1F] |
| 132 | 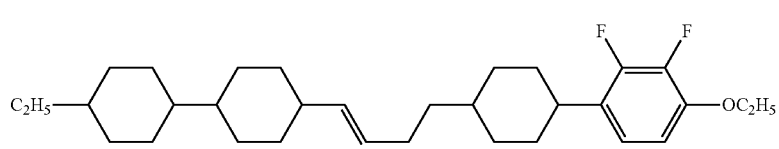 |
| 133 | 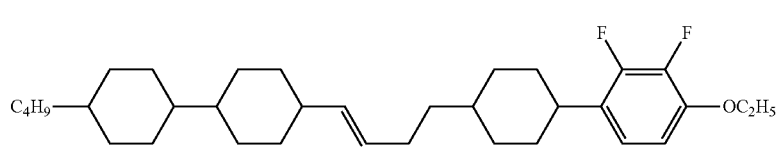 [SMILES: CCOc1ccc(C2CCC(CC/C=C/C3CCC(C4CCC(CC)CC4)CC3)CC2)c(F)c1F] |

-continued
| No. | |
|---|---|
| 134 |  |
| 135 | 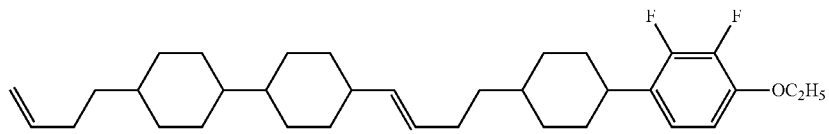 [SMILES: C=CCCC1CCC(C2CCC(/C=C/CCC3CCC(c4ccc(OCC)c(F)c4F)CC3)CC2)CC1] |
| 136 | 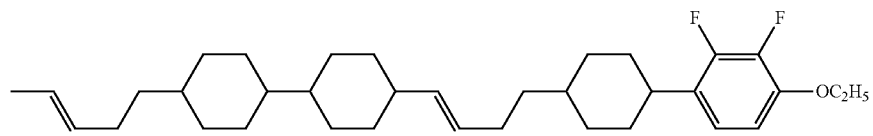 [SMILES: C/C=C/CCC1CCC(C2CCC(/C=C/CCC3CCC(c4ccc(OCC)c(F)c4F)CC3)CC2)CC1] |
| 137 | 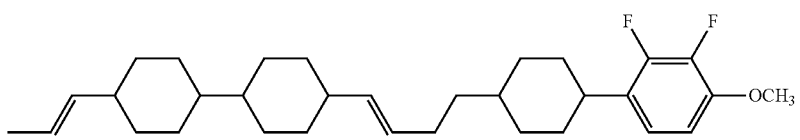 [SMILES: C/C=C/C1CCC(C2CCC(/C=C/CCC3CCC(c4ccc(OC)c(F)c4F)CC3)CC2)CC1] |
| 138 | 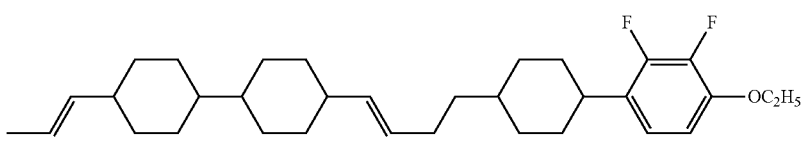 |
| 139 | 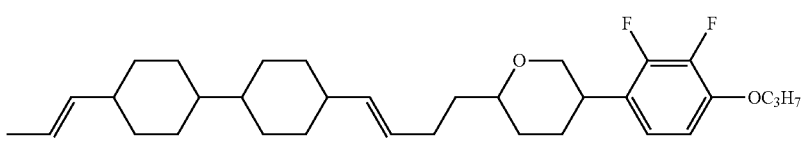 |
| 140 | 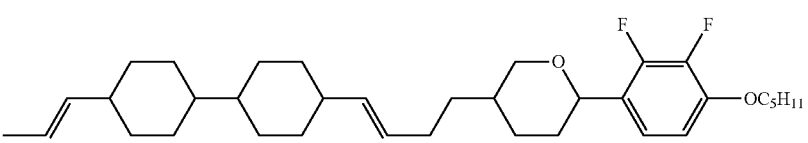 |
| 141 | 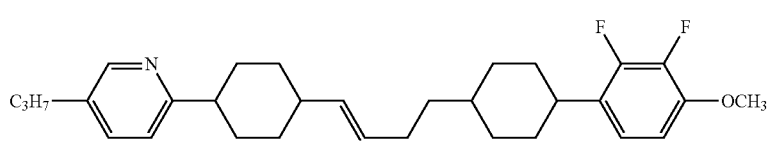 |
| 142 | 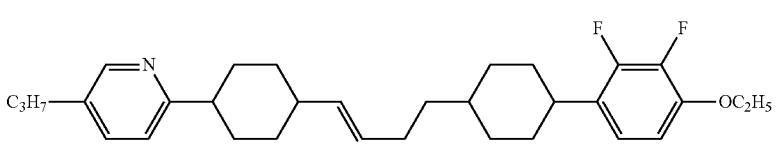 |
| 143 | 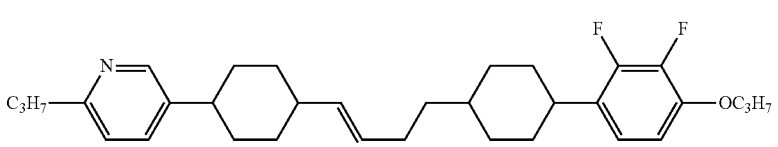 |
| 144 | 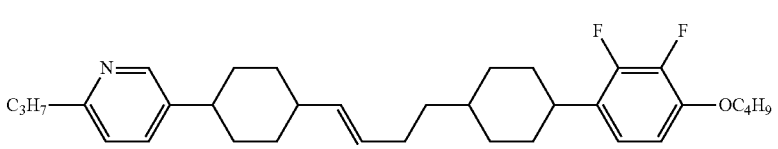 |

| No. | |
|---|---|
| 145 | 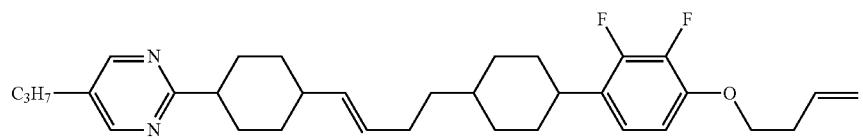 |
| 146 | 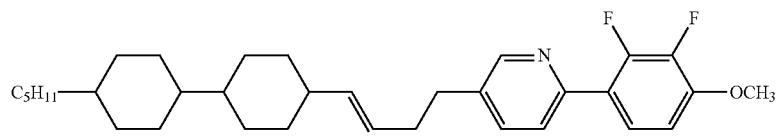 |
| 147 | 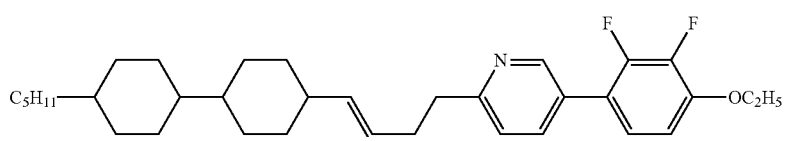 |
| 148 | 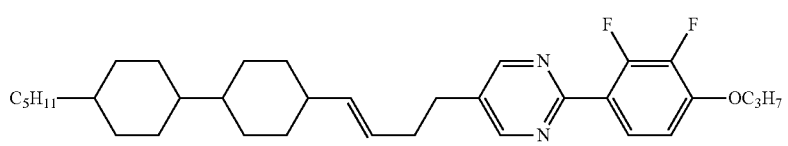 |
| 149 | 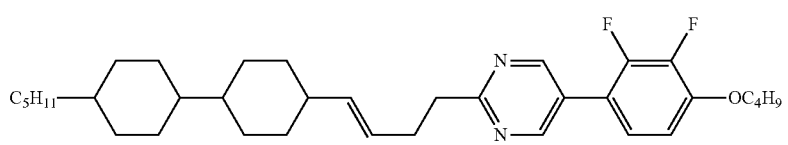 |
| 150 | 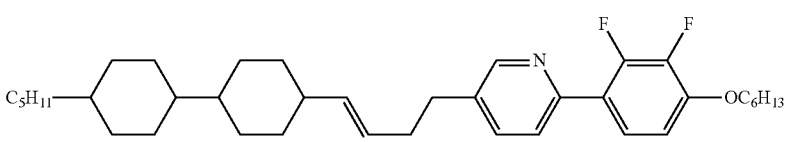 |
| 151 | 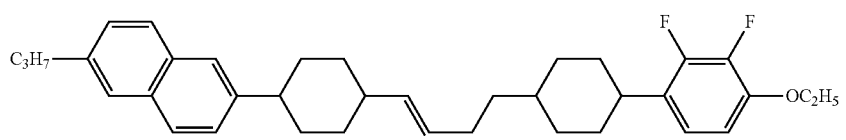 |
| 152 | 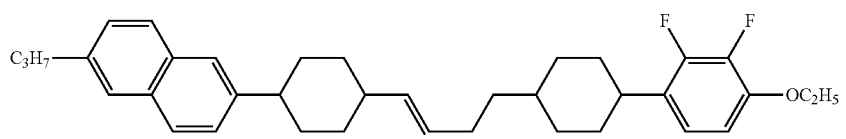 |
| 153 | 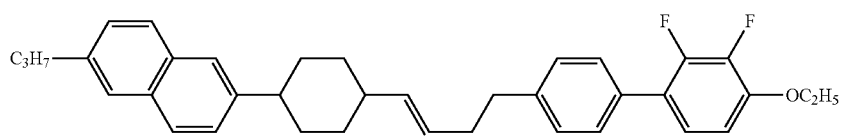 |
| 154 | 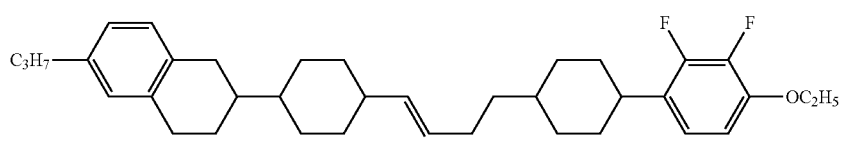 |
| 155 | 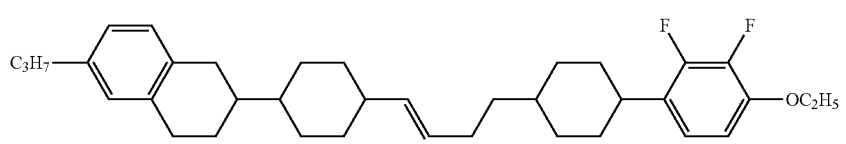 |

-continued
| No. | |
|---|---|
| 156 | 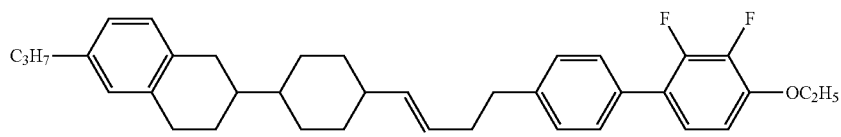 |
| 157 | 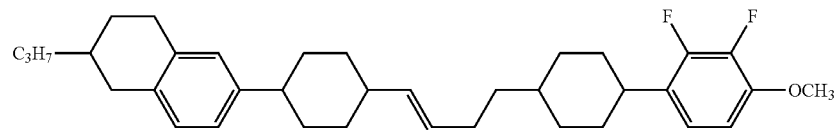 |
| 158 | 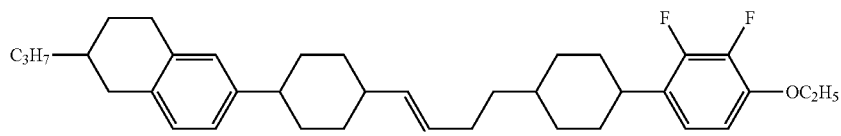 |
| 159 | 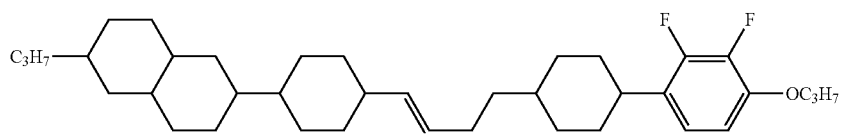 |
| 160 | 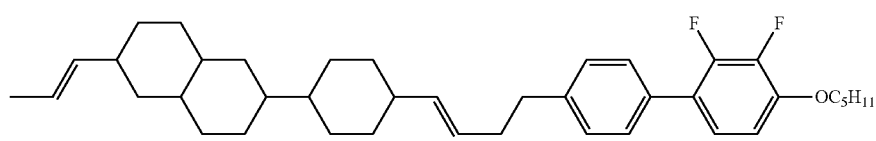 |
| 161 | 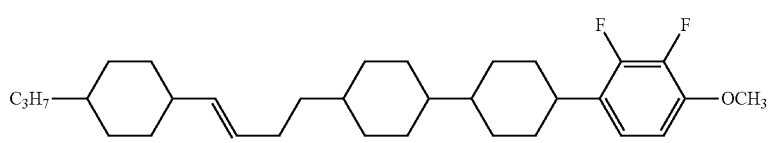 |
| 162 | 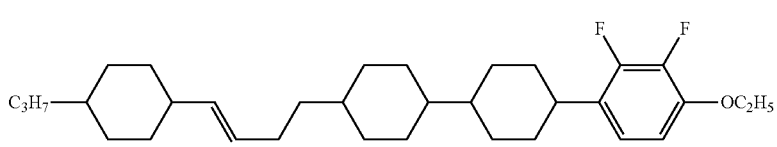 |
| 163 | 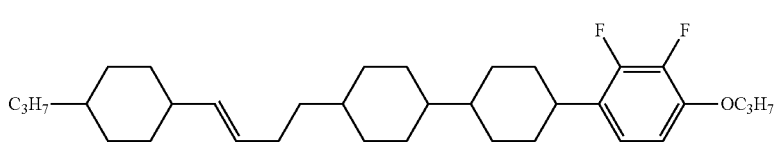 |
| 164 | 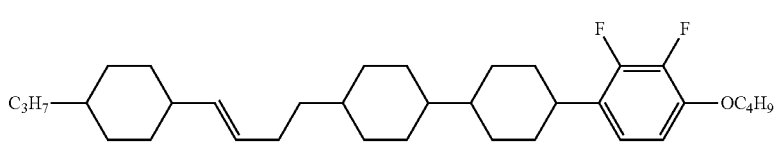 |
| 165 | 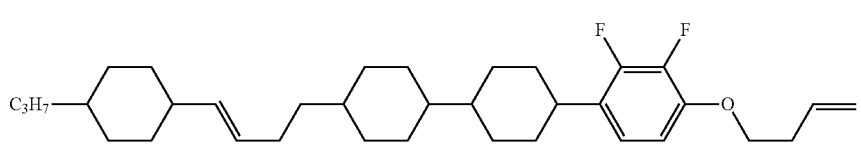 |
| 166 | 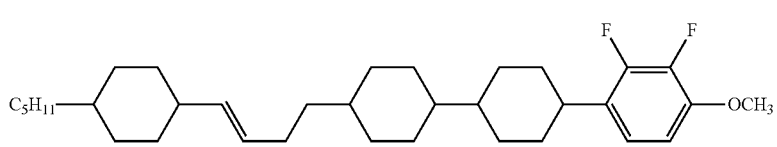 |

-continued
| No. | |
|---|---|
| 167 | 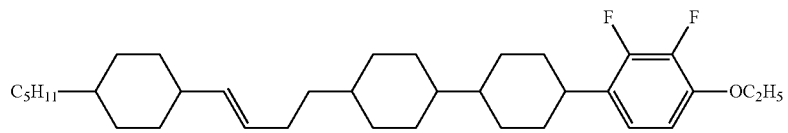 |
| 168 | 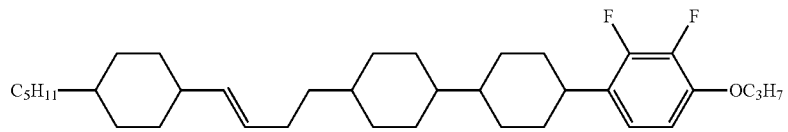 |
| 169 | 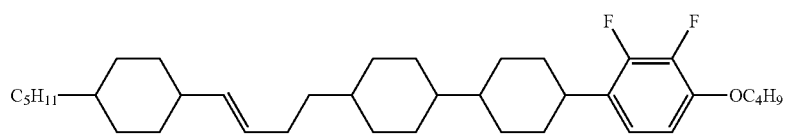 |
| 170 | 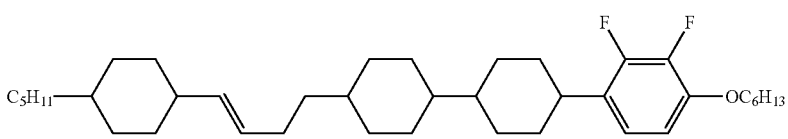 |
| 171 | 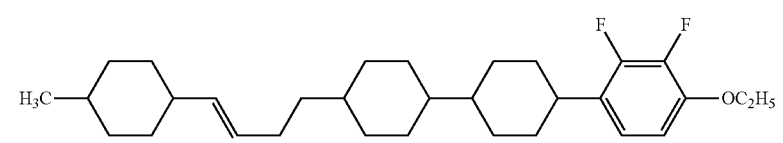 |
| 172 | 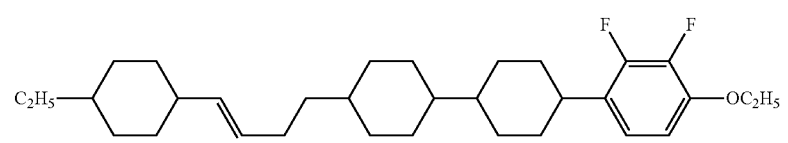 [SMILES: CCOc1ccc(C2CCC(C3CCC(CC/C=C/C4CCC(CC)CC4)CC3)CC2)c(F)c1F] |
| 173 | 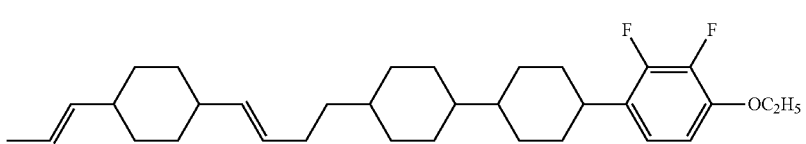 [SMILES: C/C=C/C1CCC(/C=C/CCC2CCC(C3CCC(c4ccc(OCC)c(F)c4F)CC3)CC2)CC1] |
| 174 | 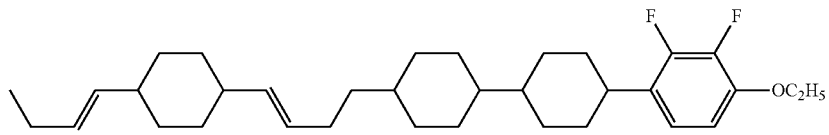 [SMILES: CC/C=C/C1CCC(/C=C/CCC2CCC(C3CCC(c4ccc(OCC)c(F)c4F)CC3)CC2)CC1] |
| 175 | 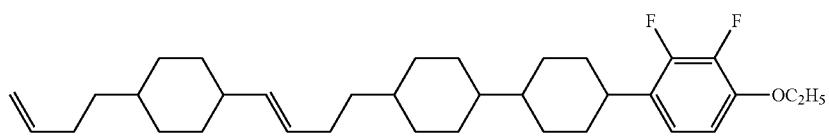 [SMILES: C=CCCC1CCC(/C=C/CCC2CCC(C3CCC(c4ccc(OCC)c(F)c4F)CC3)CC2)CC1] |
| 176 | 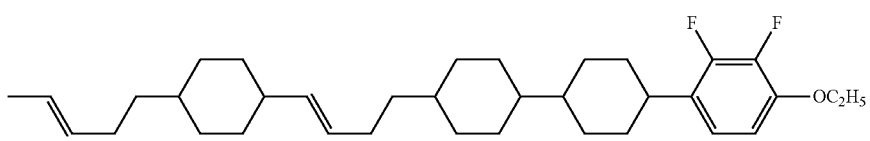 [SMILES: C/C=C/CCC1CCC(/C=C/CCC2CCC(C3CCC(c4ccc(OCC)c(F)c4F)CC3)CC2)CC1] |
| 177 | 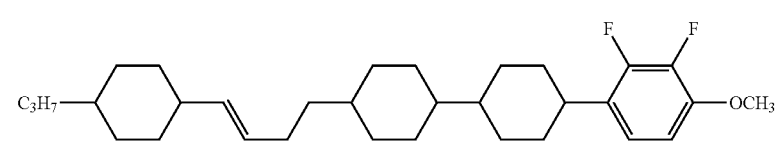 |

-continued
| No. | |
|---|---|
| 178 | 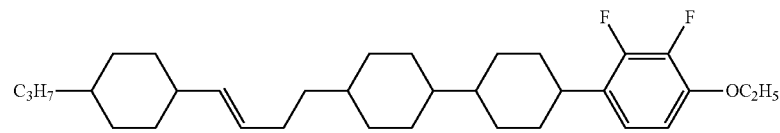 |
| 179 | 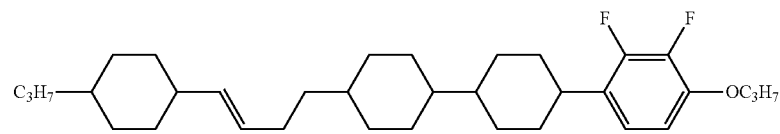 |
| 180 | 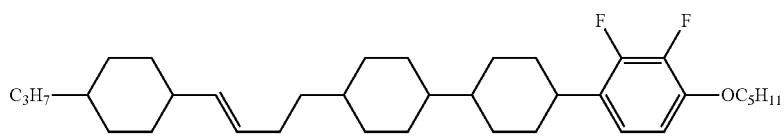 |
| 181 | 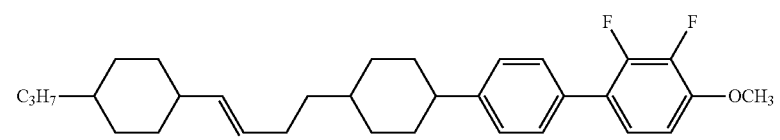 |
| 182 | 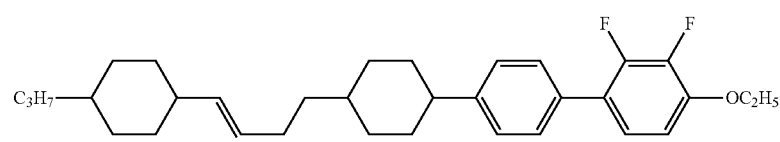 |
| 183 | 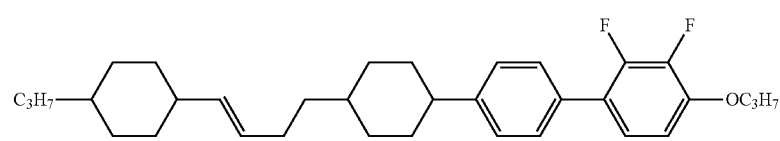 |
| 184 | 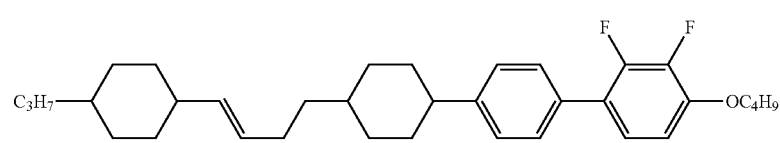 |
| 185 | 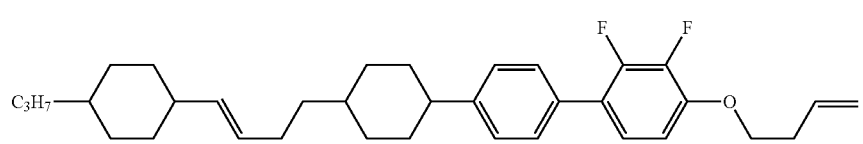 |
| 186 | 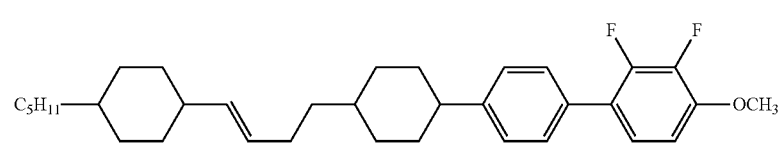 |
| 187 | 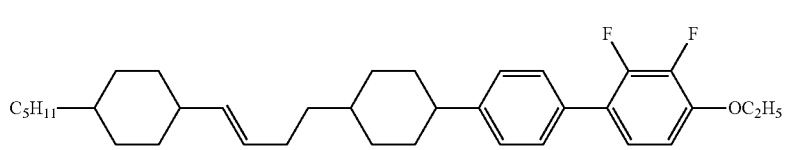 |
| 188 | 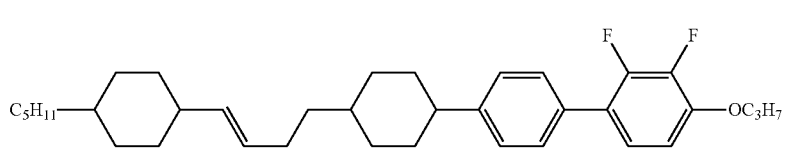 |

| No. | |
|---|---|
| 189 | 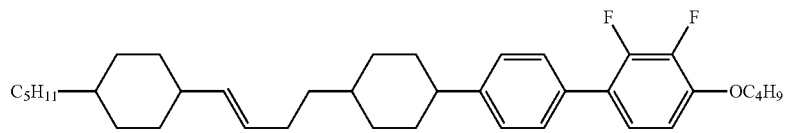 |
| 190 | 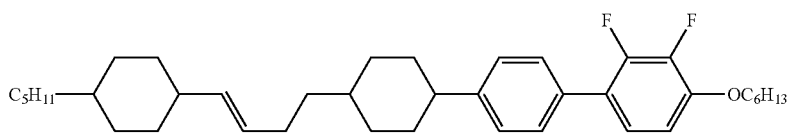 |
| 191 | 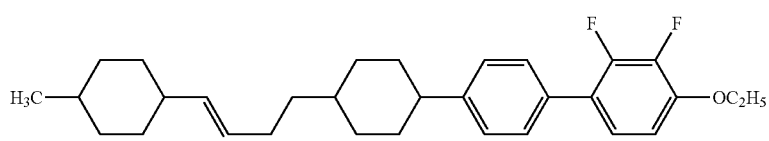 [SMILES: CCOc1ccc(-c2ccc(C3CCC(CC/C=C/C4CCC(C)CC4)CC3)cc2)c(F)c1F] |
| 192 | 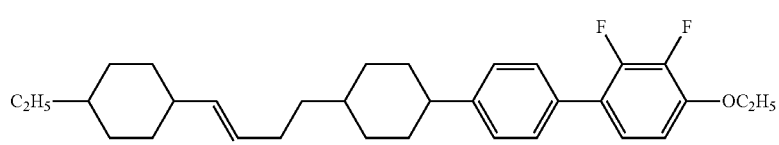 [SMILES: CCOc1ccc(-c2ccc(C3CCC(CC/C=C/C4CCC(CC)CC4)CC3)cc2)c(F)c1F] |
| 193 | 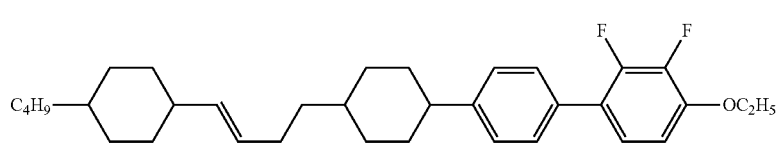 |
| 194 | 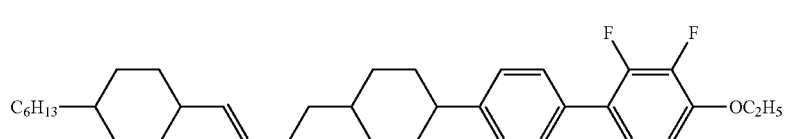 |
| 195 | 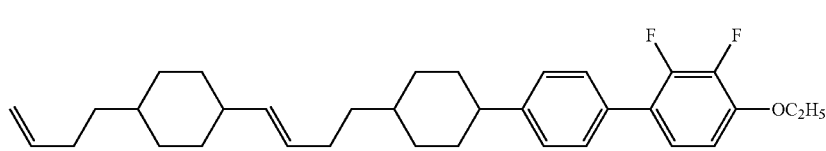 [SMILES: C=CCCC1CCC(/C=C/CCC2CCC(c3ccc(-c4ccc(OCC)c(F)c4F)cc3)CC2)CC1] |
| 196 | 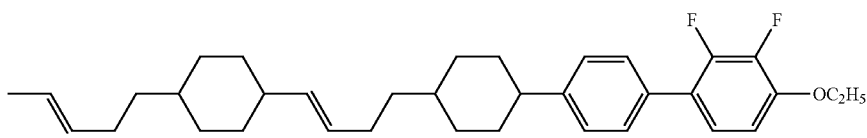 [SMILES: C/C=C/CCC1CCC(/C=C/CCC2CCC(c3ccc(-c4ccc(OCC)c(F)c4F)cc3)CC2)CC1] |
| 197 | 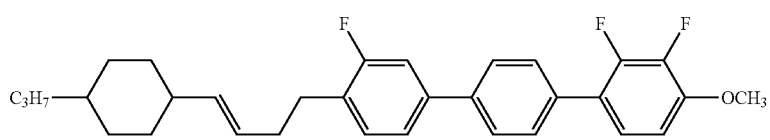 |
| 198 | 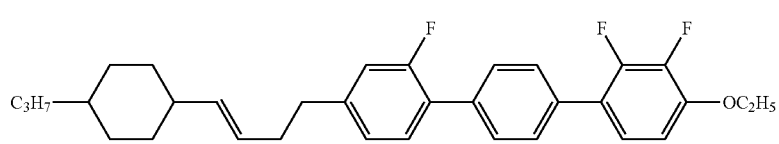 |
| 199 | 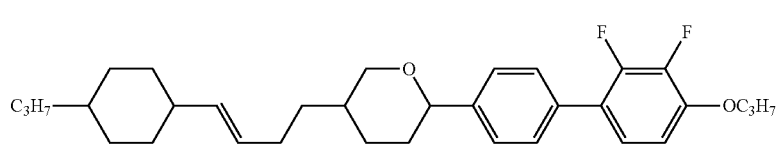 |

| No. | |
|---|---|
| 200 | 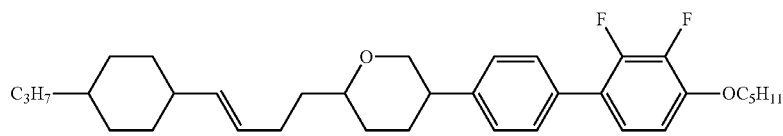 |
| 201 | 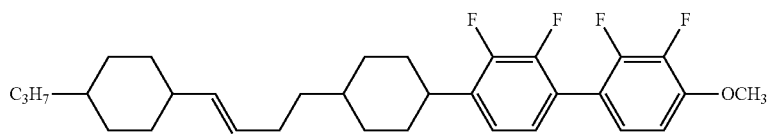 |
| 202 | 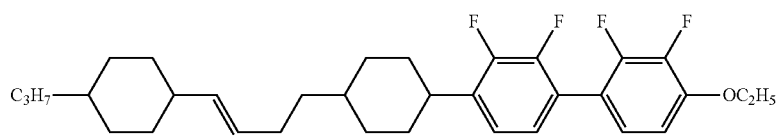 |
| 203 | 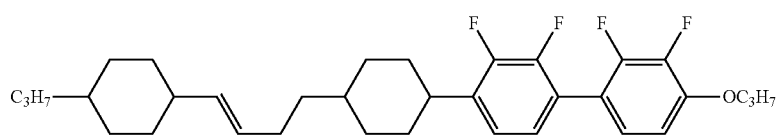 |
| 204 | 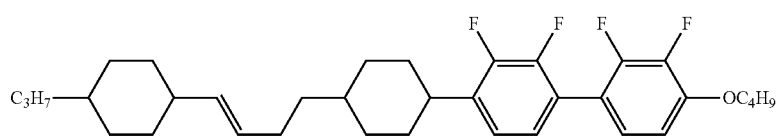 |
| 205 | 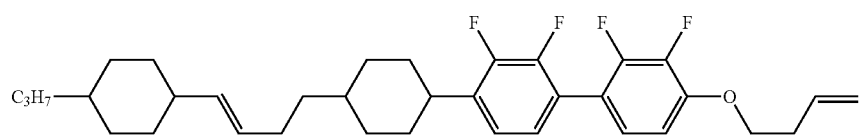 |
| 206 | 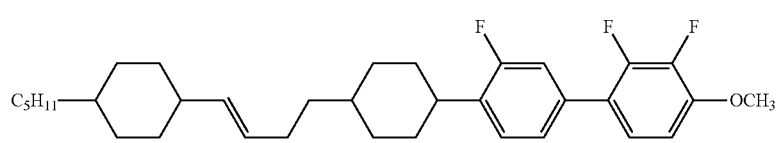 |
| 207 | 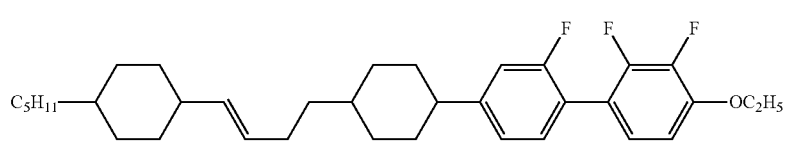 |
| 208 | 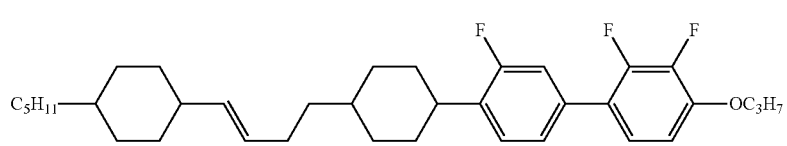 |
| 209 | 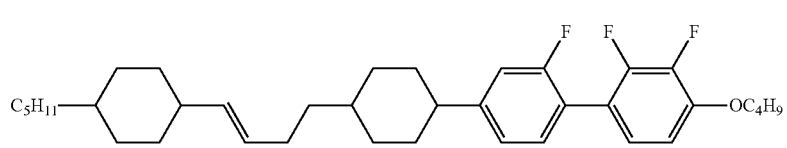 |
| 210 | 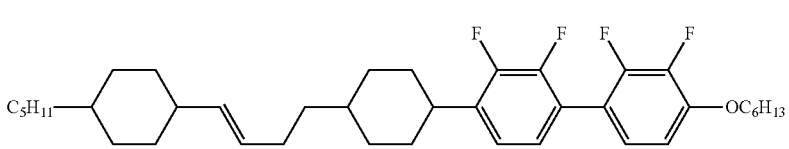 |

| No. | |
|---|---|
| 211 | 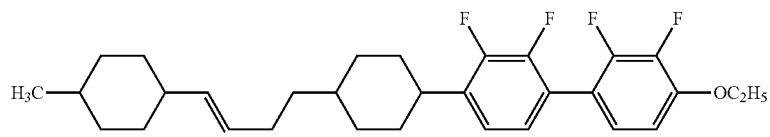 |
| 212 | 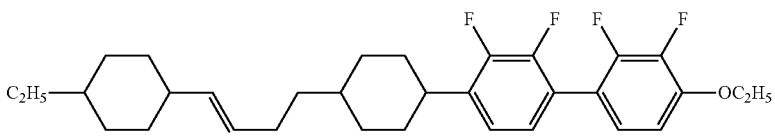 |
| 213 | 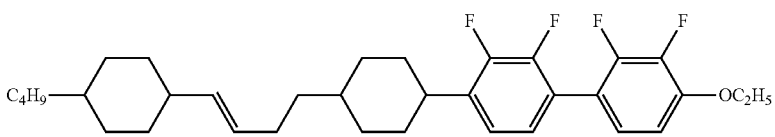 |
| 214 | 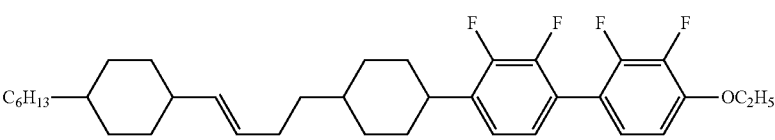 |
| 215 | 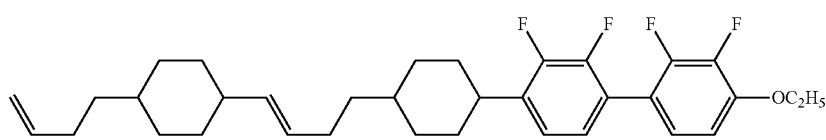 |
| 216 | 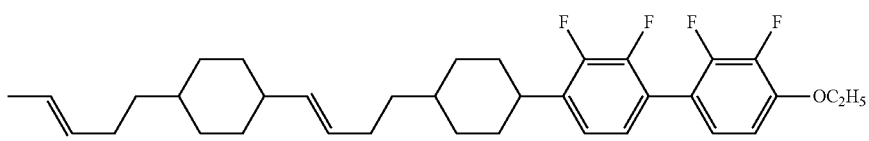 [SMILES: C/C=C/CCC1CCC(/C=C/CCC2CCC(c3ccc(-c4ccc(OCC)c(F)c4F)c(F)c3F)CC2)CC1] |
| 217 | 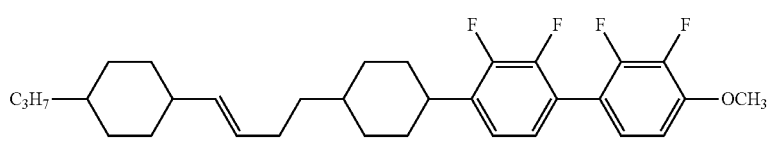 |
| 218 | 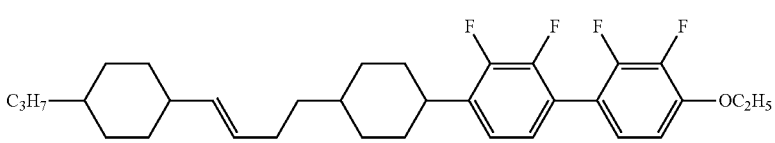 |
| 219 | 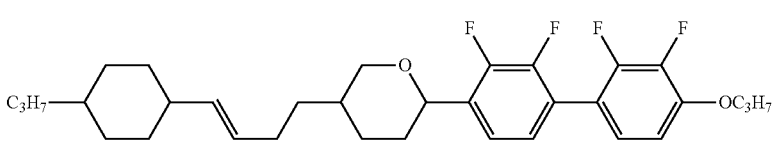 |
| 220 | 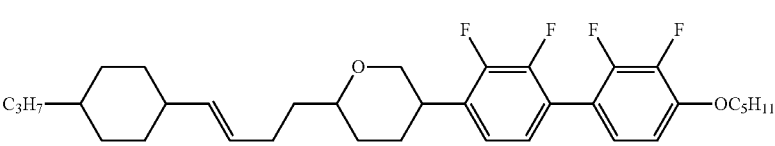 |
| 221 | 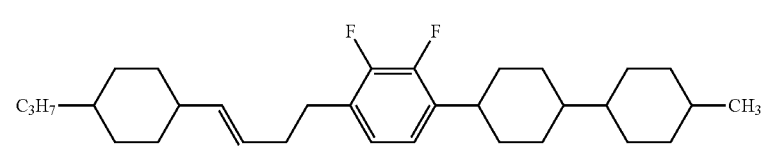 |

| No. | |
|---|---|
| 222 | 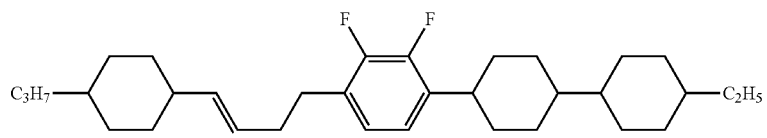 |
| 223 | 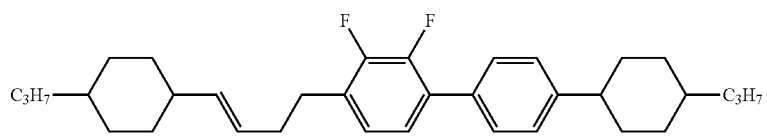 |
| 224 | 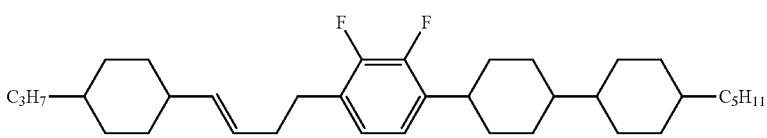 |
| 225 | 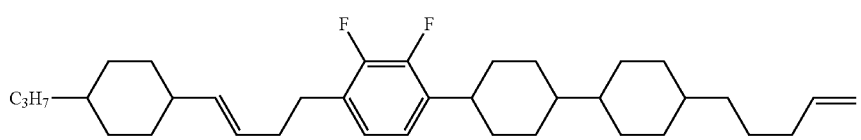 |
| 226 | 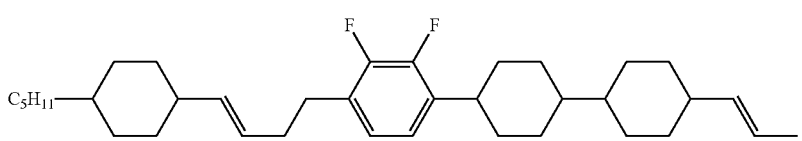 |
| 227 | 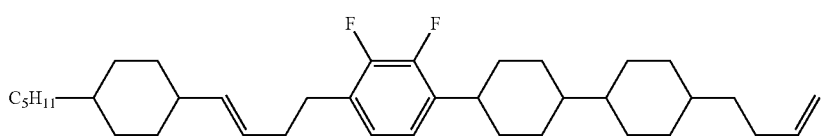 |
| 228 | 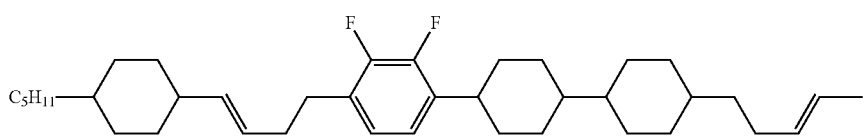 |
| 229 | 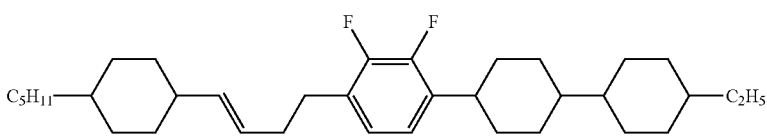 |
| 230 | 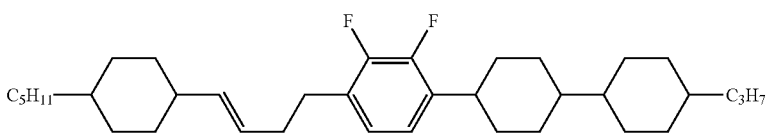 |
| 231 | 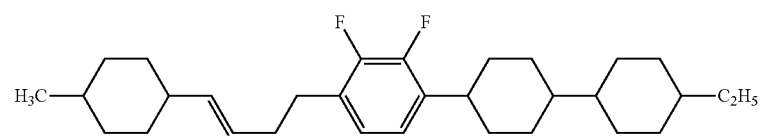 [SMILES: CCC1CCC(C2CCC(c3ccc(CC/C=C/C4CCC(C)CC4)c(F)c3F)CC2)CC1] |
| 232 | 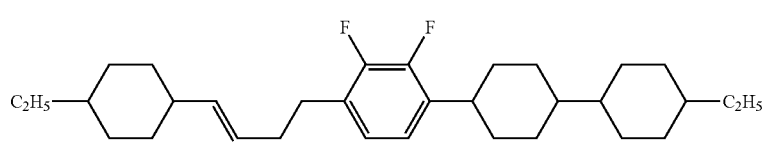 |

-continued
| No. | |
|---|---|
| 233 | 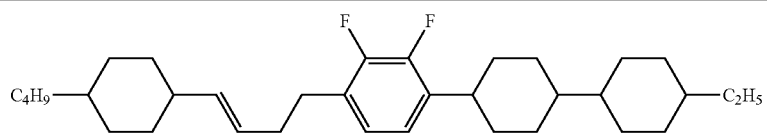 |
| 234 | 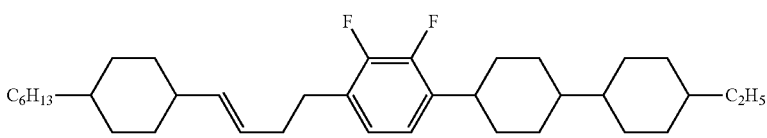 |
| 235 | 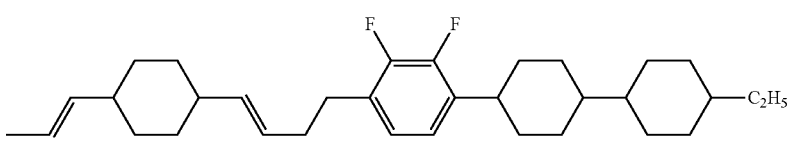 [SMILES: C/C=C/C1CCC(/C=C/CCc2ccc(C3CCC(C4CCC(CC)CC4)CC3)c(F)c2F)CC1] |
| 236 | 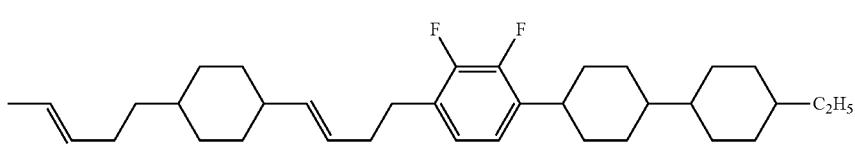 [SMILES: C/C=C/CCC1CCC(/C=C/CCc2ccc(C3CCC(C4CCC(CC)CC4)CC3)c(F)c2F)CC1] |
| 237 | 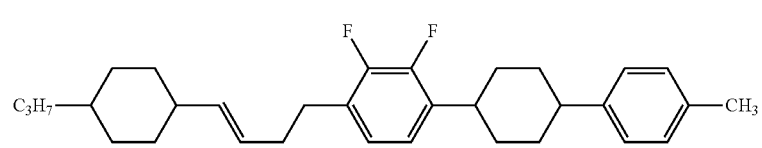 |
| 238 | 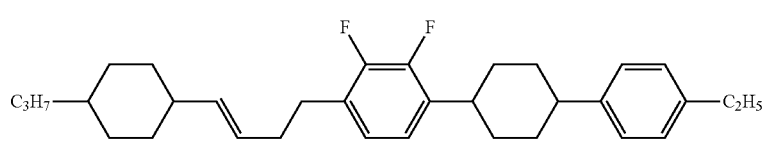 |
| 239 | 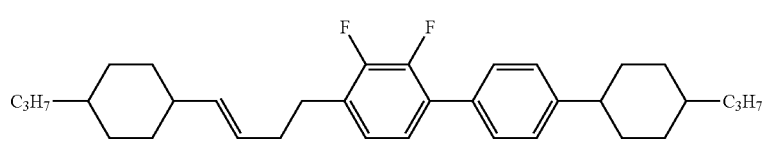 |
| 240 | 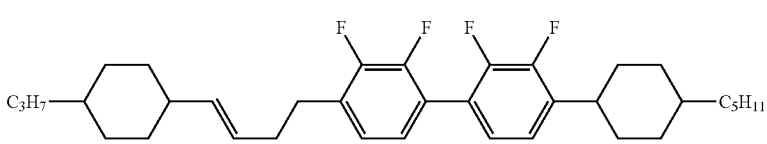 |
| 241 | 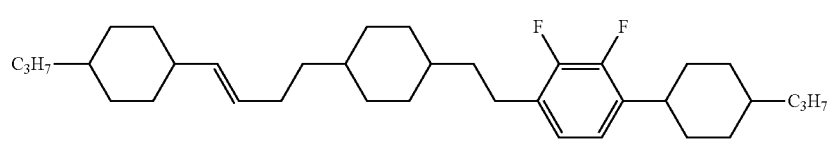 |
| 242 | 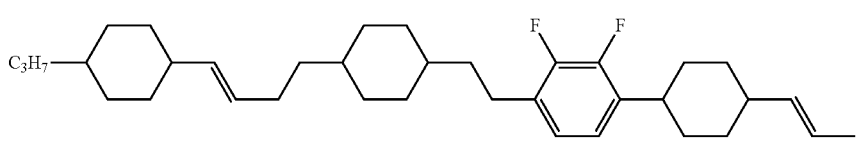 |
| 243 | 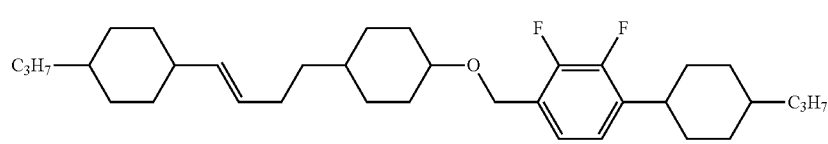 |

| No. | |
|---|---|
| 244 | 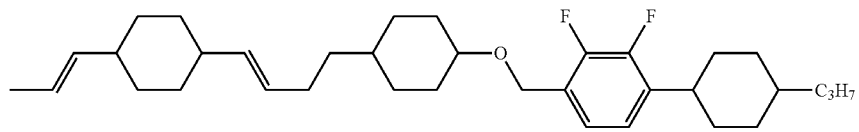 |
| 245 | 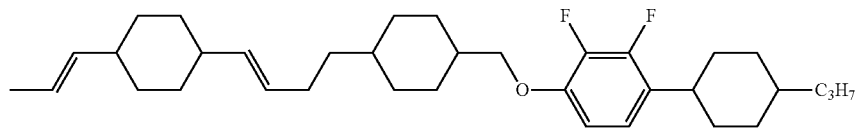 |
| 246 | 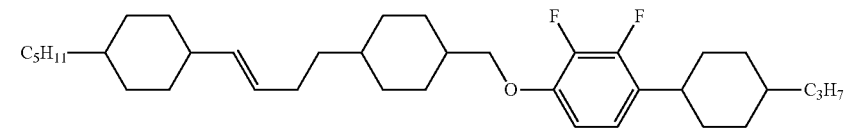 |
| 247 | 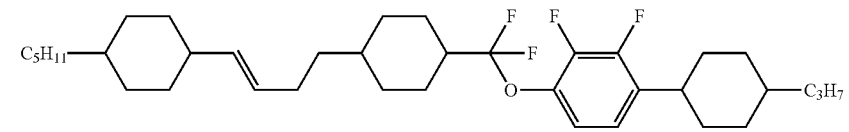 |
| 248 | 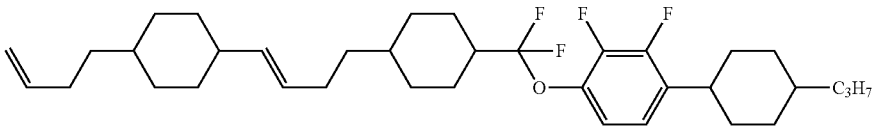 |
| 249 | 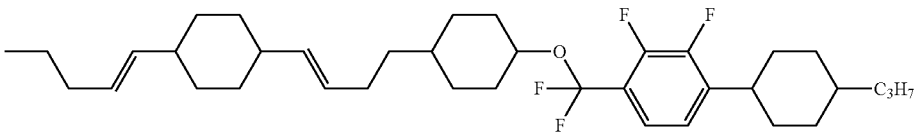 |
| 250 | 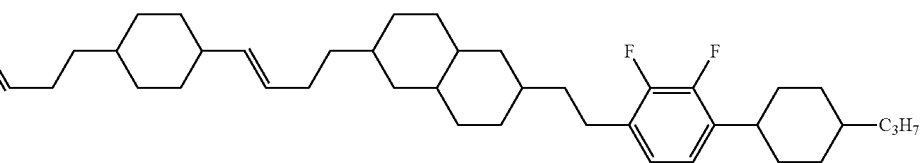 |
| 251 | 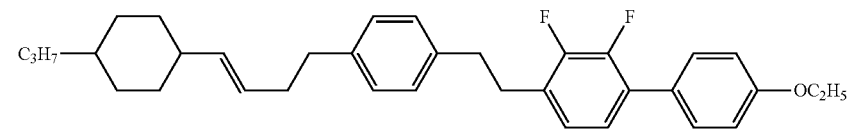 |
| 252 | 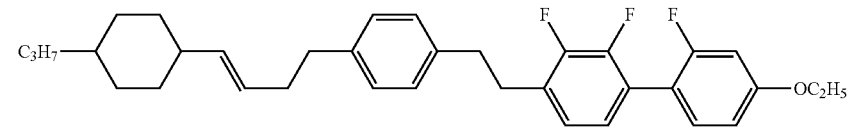 |
| 253 | 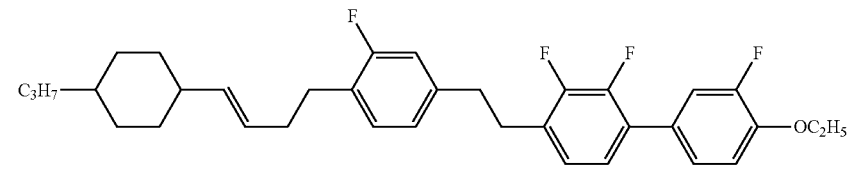 |

-continued
| No. | |
|---|---|
| 254 | 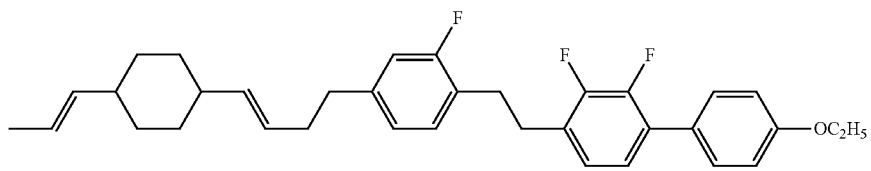 [SMILES: C/C=C/C1CCC(/C=C/CCc2ccc(CCc3ccc(-c4ccc(OCC)cc4)c(F)c3F)c(F)c2)CC1] |
| 255 | 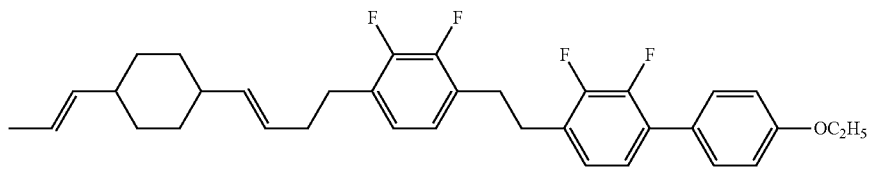 |
| 256 | 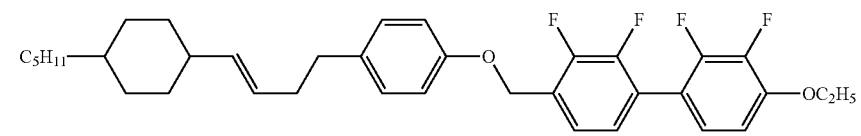 |
| 257 | 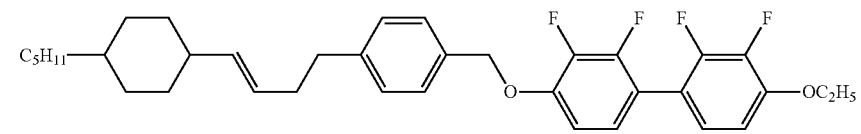 |
| 258 | 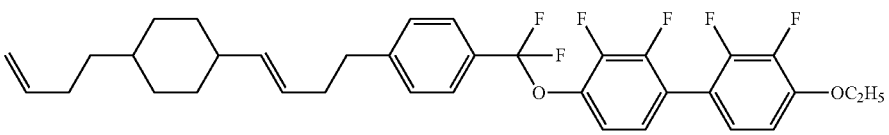 |
| 259 | 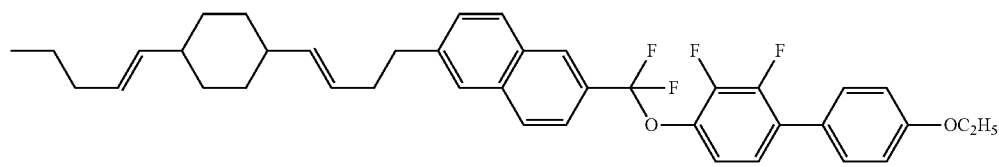 [SMILES: CCC/C=C/C1CCC(/C=C/CCc2ccc3cc(C(F)(F)Oc4ccc(-c5ccc(OCC)cc5)c(F)c4F)ccc3c2)CC1] |
| 260 | 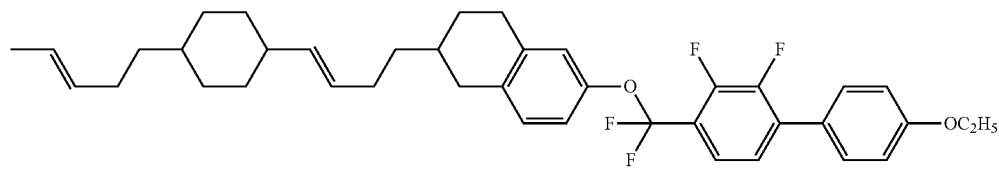 [SMILES: C/C=C/CCC1CCC(/C=C/CCC2CCc3cc(OC(F)(F)c4ccc(-c5ccc(OCC)cc5)c(F)c4F)ccc3C2)CC1] |
Comparative Example 1
Compound (F') was prepared as Comparative Example. The reason is that comparative compound (F') is similar to compound (F) described in JP H04-330019 A. Both compounds are different only in left terminal groups.
Compound (F) Described in JP H04-330019 A:
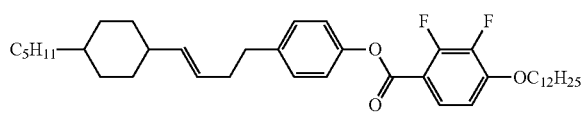
(F)
Comparative Compound (F')
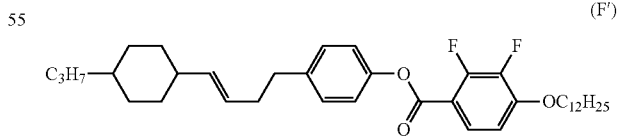
(F')
Chemical shift δ (ppm; CDCl$_3$): 7.83 (td, 1H), 7.21 (d, 2H), 7.10 (d, 2H), 6.81 (t, 1H), 5.38 (m, 2H), 4.12 (q, 2H), 2.61 (t, 2H), 1.88 (quin, 2H), 1.71 (m, 4H), 1.59 (quin, 2H), 1.48 (quin, 2H), 1.40-1.23 (m, 16H), 1.23-1.11 (m, 6H), 0.91-0.82 (m, 10H).

Transition temperature of comparison compound (F') was described below.

Transition temperature: C 57.7 $S_A$ 95.2 N 114.9 I.

Composition iv composed of 85% by weight of base liquid crystal (i) and 15% by weight of comparative compound (F') was prepared. Physical properties of composition iv obtained were measured, and extrapolated values of physical properties of comparative compound (F') were estimated by extrapolation. The values were described below.

Dielectric anisotropy ($\Delta\varepsilon$)=−3.04.

Viscosity ($\eta$)=100.5 mPa·s.

Physical Properties of Compound (No. 52)

Composition v composed of 85% by weight of base liquid crystal (i) and 15% by weight of compound (No. 52) obtained in Example 1 was prepared. Physical properties of composition v were measured and extrapolated values of physical properties of compound (No. 52) were estimated by extrapolation. The values were as described below.

Dielectric anisotropy ($\Delta\varepsilon$)=−4.58.

Viscosity ($\eta$)=45.6 mPa·s.

Therefore, large negative dielectric anisotropy ($\Delta\varepsilon$) and low viscosity ($\eta$) of compound (No. 52) were found. It is found that compound (No. 52) has larger negative dielectric anisotropy ($\Delta\varepsilon$) and lower viscosity compared with comparative compound (F').

1-2. Example of Composition (1)

Liquid crystal composition (1) of the invention will be described in detail by way of Examples. Compounds described in Examples were expressed using symbols according to definitions in the Table below. In the Table, a configuration of 1,4-cyclohexylene is trans. A parenthesized number next to a symbolized compound in Examples corresponds to the number of the compound. A symbol (-) means any other liquid crystal compound. A ratio (percentage) of a liquid crystal compound is expressed in terms of weight percentage (% by weight) based on the total weight of the liquid crystal composition. Values of physical properties of the composition were summarized in a last part. The physical properties were measured in accordance with the methods described above, and were directly described without extrapolating the measured values.

TABLE 1

Method for Description of Compounds using Symbols
R—(A$_1$)—Z$_1$— . . . —Z$_n$—(A$_n$)—R'

| 1) Left-terminal Group R— | Symbol |
|---|---|
| $C_nH_{2n+1}$— | n- |
| $C_nH_{2n+1}O$— | nO— |
| $C_mH_{2m+1}OC_nH_{2n}$— | mOn- |
| $CH_2$=CH— | V— |
| $C_nH_{2n+1}$—CH=CH— | nV— |
| $CH_2$=CH—$C_nH_{2n}$— | Vn- |
| $C_mH_{2m+1}$—CH=CH—$C_nH_{2n}$— | mVn- |
| $CF_2$=CH— | VFF— |
| $CF_2$=CH—$C_nH_{2n}$— | VFFn- |
| 2) Right-terminal Group —R' | Symbol |
| —$C_nH_{2n+1}$ | -n |
| —$OC_nH_{2n+1}$ | —On |
| —COOCH$_3$ | -EMe |
| —CH=CH$_2$ | —V |
| —CH=CH—$C_nH_{2n+1}$ | —Vn |
| —$C_nH_{2n}$—CH=CH$_2$ | -nV |
| —$C_mH_{2m}$—CH=CH—$C_nH_{2n+1}$ | -mVn |
| —CH=CF$_2$ | —VFF |
| —F | —F |
| —Cl | —CL |

TABLE 1-continued

Method for Description of Compounds using Symbols
R—(A$_1$)—Z$_1$— . . . —Z$_n$—(A$_n$)—R'

| | |
|---|---|
| —OCF$_3$ | —OCF$_3$ |
| —OCF$_2$H | —OCF2H |
| —CF$_3$ | —CF3 |
| —CF=CH—CF$_3$ | —FVCF3 |
| —C≡N | —C |
| 3) Bonding Group —Z$_n$— | Symbol |
| —$C_nH_{2n}$— | n |
| —COO— | E |
| —CH=CH—$C_nH_{2n}$— | Vn |
| —CH$_2$O— | 1O |
| —OCH$_2$— | O1 |
| —CF$_2$O— | X |
| —C≡C— | T |
| 4) Ring Structure —A$_n$— | Symbol |

H

B

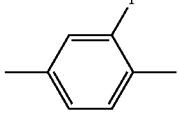

B(F)

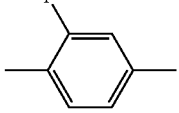

B(2F)

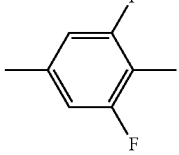

B(F,F)

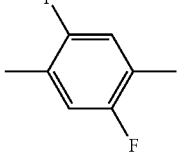

B(2F,5F)

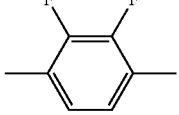

B(2F,3F)

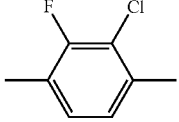

B(2F,3CL)

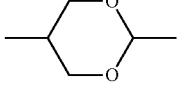

G

TABLE 1-continued

Method for Description of Compounds using Symbols
R—(A₁)—Z₁—...—Zₙ—(Aₙ)—R'

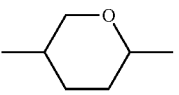 dh

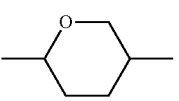 Dh

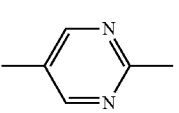 Py

5) Examples of Description

Example 1 3-BB(F,F)XB(F,F)—F

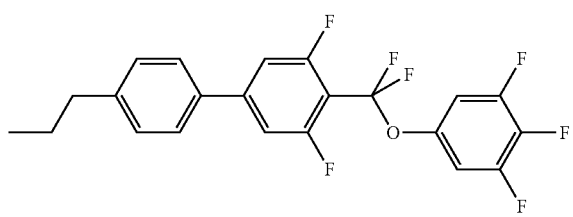 [SMILES: CCCc1ccc(-c2cc(F)c(C(F)(F)Oc3cc(F)c(F)c(F)c3)c(F)c2)cc1]

Example 2 3-HHB(F,F)—F

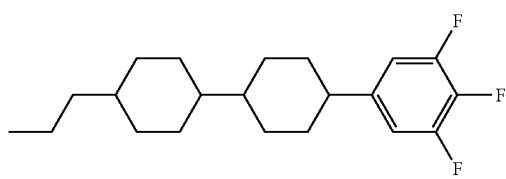 [SMILES: CCCC1CCC(C2CCC(c3cc(F)c(F)c(F)c3)CC2)CC1]

Example 3 3-HH-4

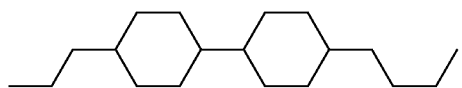 [SMILES: CCCCC1CCC(C2CCC(CCC)CC2)CC1]

Example 4 3-HV2B(2F,3F)—O2

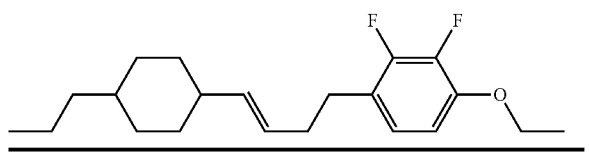

Example 4

| 3-HV2B(2F,3F)-O2 | (No. 2) | 5% |
| 3-HB-O2 | (13-5) | 10% |
| 5-HB-CL | (2-2) | 13% |
| 3-HBB(F,F)-F | (3-24) | 7% |
| 3-PyB(F)-F | (3-80) | 10% |
| 5-PyB(F)-F | (3-80) | 10% |
| 3-PyBB-F | (3-81) | 10% |
| 4-PyBB-F | (3-81) | 9% |
| 5-PyBB-F | (3-81) | 7% |
| 5-HBB(F)B-2 | (15-5) | 10% |
| 5-HBB(F)B-3 | (15-5) | 9% |

Example 5

| 3-HV2BB(2F,3F)-O2 | (No. 52) | 6% |
| 2-HB-C | (5-1) | 5% |
| 3-HB-C | (5-1) | 12% |
| 3-HB-O2 | (13-5) | 12% |
| 2-BTB-1 | (13-10) | 4% |
| 3-HHB-F | (3-1) | 3% |
| 3-HHB-1 | (14-1) | 8% |
| 3-HHB-O1 | (14-1) | 5% |
| 3-HHB-3 | (14-1) | 12% |
| 3-HHEB-F | (3-10) | 4% |
| 5-HHEB-F | (3-10) | 4% |
| 2-HHB(F)-F | (3-2) | 7% |
| 3-HHB(F)-F | (3-2) | 6% |
| 5-HHB(F)-F | (3-2) | 7% |
| 3-HHB(F,F)-F | (3-3) | 5% |

NI = 102.8° C.; η = 19.9 mPa · s; Δn = 0.107; Δε = 4.2.

Example 6

| 3-HV2B(2F,3F)-O2 | (No. 2) | 4% |
| 7-HB(F,F)-F | (2-4) | 4% |
| 3-HB-O2 | (13-5) | 7% |
| 2-HHB(F)-F | (3-2) | 10% |
| 3-HHB(F)-F | (3-2) | 10% |
| 5-HHB(F)-F | (3-2) | 10% |
| 2-HBB(F)-F | (3-23) | 8% |
| 3-HBB(F)-F | (3-23) | 8% |
| 5-HBB(F)-F | (3-23) | 13% |
| 2-HBB-F | (3-22) | 4% |
| 3-HBB-F | (3-22) | 4% |
| 5-HBB-F | (3-22) | 3% |
| 3-HBB(F,F)-F | (3-24) | 5% |
| 5-HBB(F,F)-F | (3-24) | 10% |

Example 7

| 3-HV2BB(2F,3F)-O2 | (No. 52) | 5% |
| 5-HB-CL | (2-2) | 16% |
| 3-HH-4 | (13-1) | 12% |
| 3-HH-5 | (13-1) | 4% |
| 3-HHB-F | (3-1) | 4% |
| 3-HHB-CL | (3-1) | 3% |
| 4-HHB-CL | (3-1) | 4% |
| 3-HHB(F)-F | (3-2) | 10% |
| 4-HHB(F)-F | (3-2) | 9% |
| 5-HHB(F)-F | (3-2) | 9% |
| 7-HHB(F)-F | (3-2) | 8% |
| 5-HBB(F)-F | (3-23) | 4% |
| 1O1-HBBH-5 | (15-1) | 3% |
| 4-HHBB(F,F)-F | (4-6) | 3% |
| 3-HH2BB(F,F)-F | (4-15) | 3% |
| 4-HH2BB(F,F)-F | (4-15) | 3% |

NI = 112.3° C.; η = 17.8 mPa · s; Δn = 0.093; Δε = 3.0.

Example 8

| 3-HV2B(2F,3F)-O2 | (No. 2) | 5% |
| 5-HB-F | (2-2) | 12% |
| 6-HB-F | (2-2) | 9% |
| 7-HB-F | (2-2) | 7% |
| 2-HHB-OCF3 | (3-1) | 7% |
| 3-HHB-OCF3 | (3-1) | 7% |
| 4-HHB-OCF3 | (3-1) | 7% |

-continued

| | | |
|---|---|---|
| 5-HHB-OCF3 | (3-1) | 5% |
| 3-HH2B-OCF3 | (3-4) | 4% |
| 5-HH2B-OCF3 | (3-4) | 4% |
| 3-HHB(F,F)-OCF2H | (3-3) | 3% |
| 3-HHB(F,F)-OCF3 | (3-3) | 3% |
| 3-HH2B(F)-F | (3-5) | 3% |
| 3-HBB(F)-F | (3-23) | 9% |
| 5-HBB(F)-F | (3-23) | 9% |
| 5-HBBH-3 | (15-1) | 3% |
| 3-HB(F)BH-3 | (15-2) | 3% |

Example 9

| | | |
|---|---|---|
| 3-HV2BB(2F,3F)-O2 | (No. 52) | 5% |
| 3-HHB(F,F)-F | (3-3) | 9% |
| 3-H2HB(F,F)-F | (3-15) | 8% |
| 4-H2HB(F,F)-F | (3-15) | 8% |
| 5-H2HB(F,F)-F | (3-15) | 8% |
| 3-HBB(F,F)-F | (3-24) | 18% |
| 5-HBB(F,F)-F | (3-24) | 17% |
| 3-H2BB(F,F)-F | (3-27) | 11% |
| 5-HHBB(F,F)-F | (4-6) | 3% |
| 5-HHEBB-F | (4-17) | 2% |
| 3-HH2BB(F,F)-F | (4-15) | 3% |
| 1O1-HBBH-4 | (15-1) | 4% |
| 1O1-HBBH-5 | (15-1) | 4% |

NI = 102.0° C.; η = 35.3 mPa · s; Δn = 0.119; Δε = 8.2.

A pitch when 0.25 part of Op-05 was added to 100 parts of the composition described above was 63.4 micrometers.

Example 10

| | | |
|---|---|---|
| 3-HV2B(2F,3F)-O2 | (No. 2) | 4% |
| 5-HB-CL | (2-2) | 11% |
| 3-HH-4 | (13-1) | 8% |
| 3-HHB-1 | (14-1) | 5% |
| 3-HHB(F,F)-F | (3-3) | 8% |
| 3-HBB(F,F)-F | (3-24) | 19% |
| 5-HBB(F,F)-F | (3-24) | 15% |
| 3-HHEB(F,F)-F | (3-12) | 8% |
| 4-HHEB(F,F)-F | (3-12) | 3% |
| 5-HHEB(F,F)-F | (3-12) | 3% |
| 2-HBEB(F,F)-F | (3-39) | 3% |
| 3-HBEB(F,F)-F | (3-39) | 5% |
| 5-HBEB(F,F)-F | (3-39) | 3% |
| 3-HHBB(F,F)-F | (4-6) | 5% |

Example 11

| | | |
|---|---|---|
| 3-HV2BB(2F,3F)-O2 | (No. 52) | 6% |
| 5-HB-CL | (2-2) | 13% |
| 7-HB(F,F)-F | (2-4) | 3% |
| 3-HH-4 | (13-1) | 9% |
| 3-HH-5 | (13-1) | 5% |
| 3-HB-O2 | (13-5) | 14% |
| 3-HHB-1 | (14-1) | 8% |
| 3-HHB-O1 | (14-1) | 5% |
| 2-HHB(F)-F | (3-2) | 7% |
| 3-HHB(F)-F | (3-2) | 7% |
| 5-HHB(F)-F | (3-2) | 7% |
| 3-HHB(F,F)-F | (3-3) | 6% |
| 3-H2HB(F,F)-F | (3-15) | 5% |
| 4-H2HB(F,F)-F | (3-15) | 5% |

NI = 78.3° C.; η = 16.7 mPa · s; Δn = 0.081; Δn = 2.3.

Example 12

| | | |
|---|---|---|
| 3-HV2B(2F,3F)-O2 | (No. 2) | 5% |
| 5-HB-CL | (2-2) | 3% |
| 7-HB(F)-F | (2-3) | 7% |
| 3-HH-4 | (13-1) | 9% |
| 3-HH-EMe | (13-2) | 20% |
| 3-HHEB-F | (3-10) | 8% |
| 5-HHEB-F | (3-10) | 8% |
| 3-HHEB(F,F)-F | (3-12) | 8% |
| 4-HHEB(F,F)-F | (3-12) | 5% |
| 4-HGB(F,F)-F | (3-103) | 5% |
| 5-HGB(F,F)-F | (3-103) | 6% |
| 2-H2GB(F,F)-F | (3-106) | 4% |
| 3-H2GB(F,F)-F | (3-106) | 5% |
| 5-GHB(F,F)-F | (3-109) | 7% |

Example 13

| | | |
|---|---|---|
| 3-HV2BB(2F,3F)-O2 | (No. 52) | 6% |
| 1V2-BEB(F,F)-C | (5-15) | 6% |
| 3-HB-C | (5-1) | 17% |
| 2-BTB-1 | (13-10) | 10% |
| 5-HH-VFF | (13-1) | 27% |
| 3-HHB-1 | (14-1) | 4% |
| VFF-HHB-1 | (14-1) | 7% |
| VFF2-HHB-1 | (14-1) | 11% |
| 3-H2BTB-2 | (14-17) | 4% |
| 3-H2BTB-3 | (14-17) | 4% |
| 3-H2BTB-4 | (14-17) | 4% |

NI = 84.5° C.; η = 14.3 mPa · s; Δn = 0.135; Δε = 6.0.

Example 14

| | | |
|---|---|---|
| 3-HV2B(2F,3F)-O2 | (No. 2) | 5% |
| 5-HB(F)B(F,F)XB(F,F)-F | (4-41) | 5% |
| 3-BB(F)B(F,F)XB(F,F)-F | (4-47) | 3% |
| 4-BB(F)B(F,F)XB(F,F)-F | (4-47) | 7% |
| 5-BB(F)B(F,F)XB(F,F)-F | (4-47) | 3% |
| 3-HH-V | (13-1) | 41% |
| 3-HH-V1 | (13-1) | 5% |
| 3-HHEH-5 | (14-13) | 3% |
| 3-HHB-1 | (14-1) | 4% |
| V-HHB-1 | (14-1) | 5% |
| V2-BB(F)B-1 | (14-6) | 5% |
| 1V2-BB-F | (2-1) | 3% |
| 3-BB(F,F)XB(F,F)-F | (3-97) | 8% |
| 3-HHBB(F,F)-F | (4-6) | 3% |

Example 15

| | | |
|---|---|---|
| 3-HV2BB(2F,3F)-O2 | (No. 52) | 6% |
| 3-GB(F)B(F,F)XB(F,F)-F | (4-57) | 4% |
| 3-BB(F)B(F,F)XB(F,F)-F | (4-47) | 3% |
| 4-BB(F)B(F,F)XB(F,F)-F | (4-47) | 6% |
| 5-BB(F)B(F,F)XB(F,F)-F | (4-47) | 3% |
| 3-HH-V | (13-1) | 39% |
| 3-HH-V1 | (13-1) | 6% |
| 3-HHEH-5 | (14-13) | 3% |
| 3-HHB-1 | (14-1) | 4% |
| V-HHB-1 | (14-1) | 5% |
| V2-BB(F)B-1 | (14-6) | 5% |

-continued

| | | |
|---|---|---|
| 1V2-BB-F | (2-1) | 3% |
| 3-BB(F,F)XB(F,F)-F | (3-97) | 5% |
| 3-GB(F,F)XB(F,F)-F | (3-113) | 5% |
| 3-HHBB(F,F)-F | (4-6) | 3% |

NI = 85.9° C.; η = 14.2 mPa · s; Δn = 0.108; Δε = 6.1.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

INDUSTRIAL APPLICABILITY

A liquid crystal compound of the invention has a high stability to heat, light and so forth, a high clearing point, a low minimum temperature of a liquid crystal phase, a small viscosity, a suitable optical anisotropy, a large negative dielectric anisotropy, a suitable elastic constant and an excellent compatibility with other liquid crystal compounds. A liquid crystal composition of the invention contains the compound, and has a high maximum temperature of a nematic phase, a low minimum temperature of the nematic phase, a small viscosity, a suitable optical anisotropy, a large negative dielectric anisotropy, and a suitable elastic constant. The composition has a suitable balance regarding at least two of physical properties. A liquid crystal display device of the invention includes the composition, and has a wide temperature range in which the device can be used, a short response time, a large voltage holding ratio, a low threshold voltage, a large contrast ratio and a long service life. Therefore, the device can be widely applied to a display of a personal computer, a television and so forth.

What is claimed is:
1. A compound represented by any one of formulas (1-4-4) to (1-4-6):

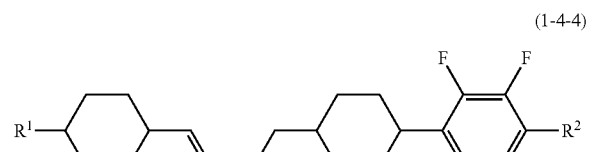
(1-4-4)

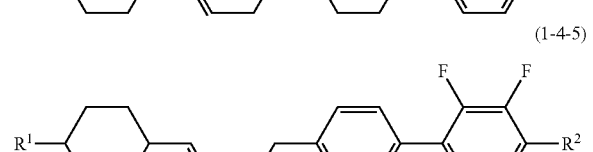
(1-4-5)

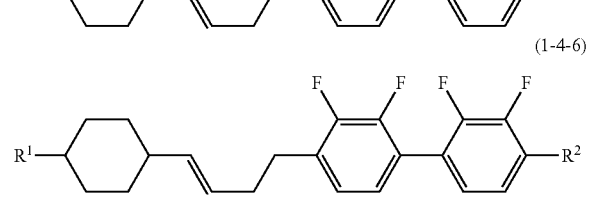
(1-4-6)

wherein, in formulas (1-4-4) to (1-4-6), $R^1$ is alkyl having 1 to 10 carbons, $R^2$ is alkyl having 1 to 10 carbons or alkoxy having 1 to 9 carbons.

2. A liquid crystal composition, containing at least one of the compounds according to claim 1.

3. The liquid crystal composition according to claim 2, further containing at least one compound selected from the group of compounds represented by each of formulas (2), (3) and (4):

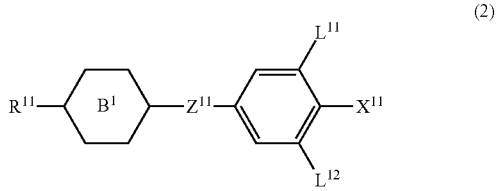
(2)

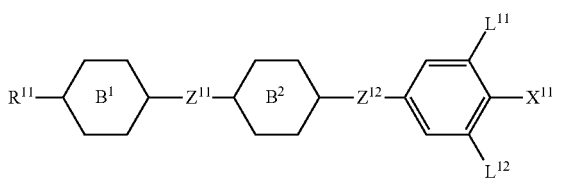
(3)

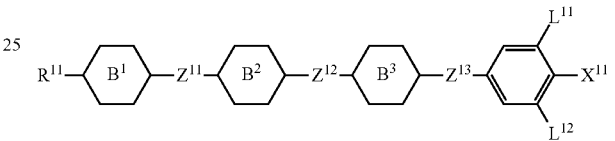
(4)

wherein, in formulas (2) to (4),
$R^{11}$ is alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—;
$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;
ring $B^1$, ring $B^2$ and ring $B^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;
$Z^{11}$, $Z^{12}$, and $Z^{13}$ are independently a single bond, —$CH_2CH_2$—, —CH=CH—, —C≡C—, —COO—, —$CF_2O$—, —$OCF_2$—, —$CH_2O$— or —$(CH_2)_4$—; and
$L^{11}$ and $L^{12}$ are independently hydrogen or fluorine.

4. The liquid crystal composition according to claim 2, further containing at least one compound selected from the group of compounds represented by formula (5):

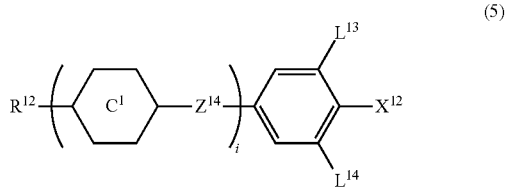
(5)

wherein, in formula (5),
$R^{12}$ is alkyl having 1 to 10 carbons or alkenyl having 2 to 10 carbons, and in the alkyl and the alkenyl, at least one of hydrogen may be replaced by fluorine and at least one of —$CH_2$— may be replaced by —O—;
$X^{12}$ is —C≡N or —C≡C—C≡N;

ring $C^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{14}$ is a single bond, —CH$_2$CH$_2$—, —C≡C—, —COO—, —CF$_2$O—, —OCF$_2$— or —CH$_2$O—;

$L^{13}$ and $L^{14}$ are independently hydrogen or fluorine; and i is 1, 2, 3 or 4.

5. The liquid crystal composition according to claim 2, further containing at least one compound selected from the group of compounds represented by formulas (6) to (12):

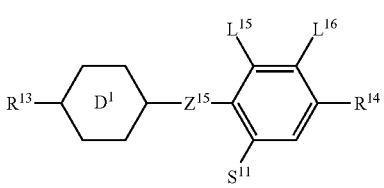
(6)

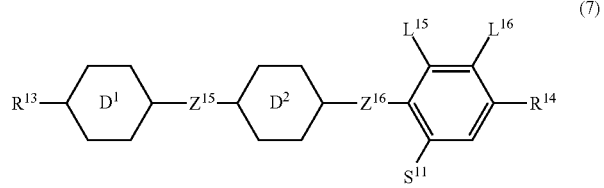
(7)

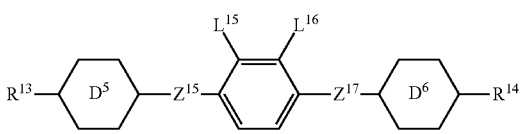
(8)

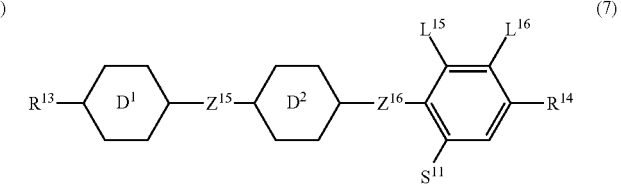
(9)

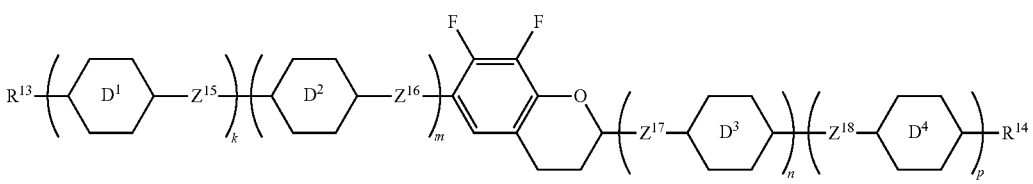
(10)

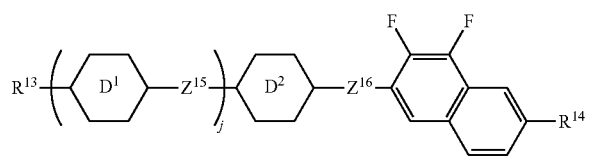
(11)

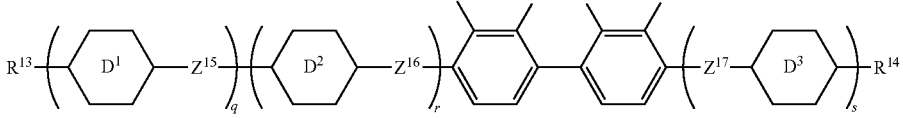

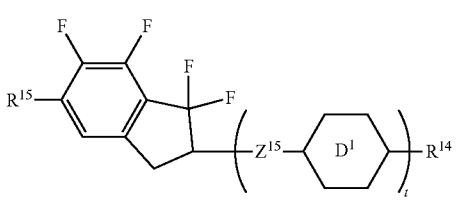
(12)

wherein, in formulas (6) to (12), $R^{13}$ and $R^{14}$ are independently alkyl having 1 to 10 carbons or alkenyl having 2 to 10 carbons, and in the alkyl or the alkenyl, at least one of —CH$_2$— may be replaced by —O— and at least one of hydrogen may be replaced by fluorine;

$R^{15}$ is hydrogen, fluorine, alkyl having 1 to 10 carbons or alkenyl having 2 to 10 carbons, and in the alkyl and the alkenyl, at least one of —CH$_2$— may be replaced by —O— and at least one of hydrogen may be replaced by fluorine;

$S^{11}$ is hydrogen or methyl;

X is —CF$_2$—, —O— or —CHF—;

ring $D^1$, ring $D^2$, ring $D^3$ and ring $D^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;

$Z^{15}$, $Z^{16}$, $Z^{17}$ and $Z^{18}$ are independently a single bond, —CH$_2$CH$_2$—, —COO—, —CH$_2$O—, —OCF$_2$— or —OCF$_2$CH$_2$CH$_2$—;

$L^{15}$ and $L^{16}$ are independently fluorine or chlorine; and j, k, m, n, p, q, r and s are independently 0 or 1, a sum of k, m, n and p is 1 or 2, a sum of q, r and s is 0, 1, 2 or 3, and t is 1, 2 or 3.

6. The liquid crystal composition according to claim 2, further containing at least one compound selected from the group of compounds represented by formulas (13) to (15):

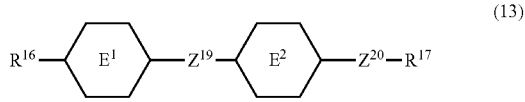
(13)

(13)
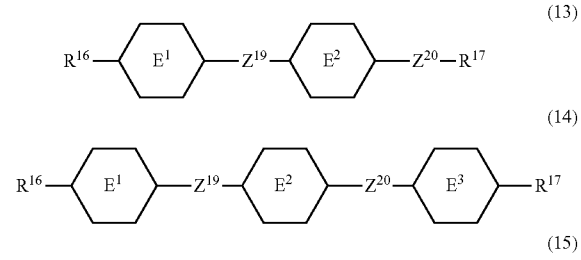

(14)
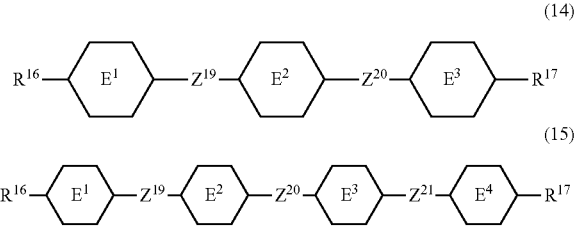

(15)
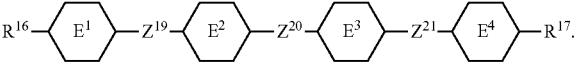

wherein, in formulas (13) to (15),

R$^{16}$ and R$^{17}$ are independently alkyl having 1 to 10 carbons or alkenyl having 2 to 10 carbons, and in the alkyl and the alkenyl, at least one of —CH$_2$— may be replaced by —O— and at least one of hydrogen may be replaced by fluorine;

ring E$^1$, ring E$^2$, ring E$^3$ and ring E$^4$ are independently 1,4-cyclohexylene, 1,4-phenylene, 2-fluoro-1,4-phenylene, 2,5-difluoro-1,4-phenylene or pyrimidine-2,5-diyl; and Z$^{19}$, Z$^{20}$ and Z$^{21}$ are independently a single bond, —CH$_2$CH$_2$—, —CH=CH—, —C≡C— or —COO—:

7. The liquid crystal composition according to claim 2, further containing at least one optically active compound and/or at least one polymerizable compound.

8. The liquid crystal composition according to claim 2, further containing at least one antioxidant and/or at least one ultraviolet light absorbent.

9. A liquid crystal display device, including the liquid crystal composition according to claim 2.

* * * * *